US011740247B2

(12) United States Patent
Acosta et al.

(10) Patent No.: US 11,740,247 B2
(45) Date of Patent: Aug. 29, 2023

(54) METHODS AND MATERIALS FOR ASSESSING AND TREATING OBESITY

(71) Applicant: Mayo Foundation for Medical Education and Research, Rochester, MN (US)

(72) Inventors: Andres J. Acosta, Rochester, MN (US); Michael L. Camilleri, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 384 days.

(21) Appl. No.: 16/765,273

(22) PCT Filed: Nov. 21, 2018

(86) PCT No.: PCT/US2018/062217
§ 371 (c)(1),
(2) Date: May 19, 2020

(87) PCT Pub. No.: WO2019/104146
PCT Pub. Date: May 31, 2019

(65) Prior Publication Data
US 2021/0072259 A1    Mar. 11, 2021

Related U.S. Application Data

(60) Provisional application No. 62/589,915, filed on Nov. 22, 2017.

(51) Int. Cl.
*G01N 33/68* (2006.01)
*A61P 3/04* (2006.01)
*A61K 31/137* (2006.01)
*A61K 31/138* (2006.01)
*A61K 31/485* (2006.01)
*A61K 38/26* (2006.01)
*C12Q 1/6883* (2018.01)

(52) U.S. Cl.
CPC ....... *G01N 33/6893* (2013.01); *A61K 31/137* (2013.01); *A61K 31/138* (2013.01); *A61K 31/485* (2013.01); *A61K 38/26* (2013.01); *A61P 3/04* (2018.01); *C12Q 1/6883* (2013.01); *C12Q 2600/106* (2013.01); *C12Q 2600/156* (2013.01); *G01N 2800/044* (2013.01)

(58) Field of Classification Search
CPC . G01N 33/6893; G01N 2800/044; A61P 3/04; A61K 31/137; A61K 31/138; A61K 31/485; A61K 38/26; C12Q 1/6883; C12Q 2600/106; C12Q 2600/156
USPC ........................................................ 436/63
See application file for complete search history.

(56) References Cited

U.S. PATENT DOCUMENTS

| 7,005,255 | B2 | 2/2006 | Kaddurah-Daouk et al. |
| 2003/0092028 | A1 | 5/2003 | Ma et al. |
| 2009/0104615 | A1 | 4/2009 | Godfrey et al. |
| 2009/0155826 | A1* | 6/2009 | Hu ..................... G01N 33/5308 435/14 |
| 2011/0124121 | A1 | 5/2011 | Dixon et al. |
| 2014/0093478 | A1* | 4/2014 | Turnbaugh ............... C12Q 1/04 424/93.4 |
| 2014/0093487 | A1 | 4/2014 | Hornbaek et al. |
| 2016/0178620 | A1 | 6/2016 | Hu et al. |
| 2016/0331272 | A1 | 11/2016 | Ahmad et al. |
| 2017/0007598 | A1 | 1/2017 | Weber et al. |

FOREIGN PATENT DOCUMENTS

EP    2979097    12/2016

OTHER PUBLICATIONS

Germain et al. Specific appetite, energetic and metabolomics responses to fat overfeeding in resistant-to-bodyweight-gain constitutional thinness. Nutrition & Diabetes (2014) 4, e126. (Year: 2014).*
Zhou et al. Obesity and diabetes related plasma amino acid alterations. Clinical Biochemistry 46 (2013) 1447-1452. (Year: 2013).*
Acosta et al., "Exenatide in obesity with accelerated gastric emptying: a randomized, pharmacodynamics study," Physiol. Reports, Nov. 2015, 3(11):e12610, 10 pages.
Acosta et al., "Quantitative Gastrointestinal and Psychological Traits Associated With Obesity and Response to Weight-Loss Therapy," Gastroenterology, Mar. 1, 2015, 148(3):537-546.e4.
Acosta et al., "Recent advances in clinical practice challenges and opportunities in the management of obesity," Gut, Apr. 2014, 63(4):687-695.
Acosta et al., "Relamorelin Relieves Constipation and Accelerates Colonic Transit in a Phase 2, Placebo-Controlled, Randomized Trial," Clin. Gastroenterol. Hepatology, Dec. 2015, 13(12):2312-2319.e1.
Acosta et al., "White Paper AGA: Power—Practice Guide on Obesity and Weight Management, Education and Resources," Clin. Gastmenterol. Hepatology, May 2017, 15(5):631-649.10.
Adams et al., "Long-Term Mortality after Gastric Bypass Surgery," N. Engl. J. Medicine, Aug. 23, 2007, 357(8):753-761.
Allison et al., "Controlled-Release Phentermines Topiramate in Severely Obese Adults: A Randomized Controlled Trial (EQUIP)." Obesity, Feb. 2012, 20(2):330-342.

(Continued)

*Primary Examiner* — Yih-Horng Shiao
(74) *Attorney, Agent, or Firm* — Cooley LLP

(57) ABSTRACT

This document relates to methods and materials for assessing and/or treating obese mammals (e.g., obese humans). For example, methods and materials for using one or more interventions (e.g., one or more pharmacological interventions) to treat obesity and/or obesity-related comorbidities in a mammal (e.g., a human) identified as being likely to respond to a particular intervention (e.g., a pharmacological intervention) are provided.

16 Claims, 22 Drawing Sheets

(56) References Cited

OTHER PUBLICATIONS

Alvarez-Castro et al., "Ghrelin in obesity, physiological mid pharmacological considerations," Mini Rev. Med. Chem., Apr. 2013, 13(4):541-552.
Apovian et al., "A Randomized, Phase 3 Trial of Naltrexone SR/Bupropion SR on Weight and Obesity-related Risk Factors (COR-II)," Obesity, May 2013, 21(5):935-943.
Apovian et al., "Pharmacological Management of Obesity: An Endocrine Society Clinical Practice Guideline," J. Clin. Endocrinol. Metabolism, Feb. 2015, 100(2):342-362.
Begriche et al., "β-Aminoisobutyric Acid Prevents Diet-induced Obesity in Mice With Partial Leptin Deficiency," Obesity, Sep. 2008, 16(9):2053-2067.
Buchwald et al., "Weight and Type 2 Diabetes after Bariatric Surgery: Systematic Review and Meta-analysis," Am. J. Medicine, Mar. 2009, 122(3):248-256.e5.
Cabanac, "Regulation and the ponderostat," Int. J. Obes. Relat. Metab. Disorders, Dec. 2001, 25(Suppl 5):S7-12.
Camilleri et al., "Gastrointestinal traits: individualizing therapy for obesity with drugs and devices," Gastrointest. Endoscopy, Jan. 1, 2016, 83(1):48-56.
Camilleri et al., "Performance characteristics of scintigraphic measurement of gastric emptying of solids in healthy participants," Neurogastroenterol. Motility, Dec. 2012, 24(12):1076-e562.
ClinicalTrials.gov [online], "Peripheral Pharmacodynamics of Phentermine-Topiramate in Obese Patients," NCT01834404, last updated Feb. 23, 2015, retrieved on Feb. 2, 2021, retrieved from URL<https://clinicaltrials.gov/ct2/show/study/NCT01834404>, 38 pages.
Connolly et al., "Valvular Heart Disease Associated with Fenfluramine-Phentermine," N. Engl. J. Medicine, Aug. 28, 1997, 337(9):581-588.
Dansinger et al., "Comparison of the Atkins, Ornish, Weight Watchers, and Zone Diets for Weight Loss and Heart Disease Risk Reduction: A Randomized Trial," JAMA, Jan. 5, 2005, 293(1):43-53.
Davidson et al., "Weight Control and Risk Factor Reduction in Obese Subjects Treated for 2 Years With Orlistat: A Randomized Controlled Trial," JAMA, Jan. 20, 1999, 281(3):235-242.
Farias et al., "Set-Point Theory and Obesity," Metab. Syndr. Relat. Disorders, Apr. 2011, 9(2):85-89.
FDA.gov [online], "Clinical Briefing Document: Endocrinologic and Metabolic Drugs Advisory Committee Meeting," NDA 22580, Feb. 22, 2012, retrieved on Feb. 2, 2021, retrieved from Url<https://wayback.archive-it.org/7993/20170405220351/https://www.fda.gov/downloads/AdvisoryCommittees/CommitteesMeetingMaterials/Drugs/EndocrinologicandMetabolicDrugsAdvisoryCommittee/UCM292315.pdf>, 200 pages.
Flegal et al., "Prevalence of Obesity and Trends in the Distribution of Body Mass Index Among US Adults, 1999-2010," JAMA, Feb. 1, 2012, 307(5):491-497.
Fontaine et al., "Years of Life Lost Due to Obesity," JAMA, Jan. 8, 2003, 289(2):187-193.
Fothergill et al., "Persistent Metabolic Adaptation 6 Years After "The Biggest Loser" Competition," Obesity, Aug. 2016, 24(8):1612-1619.
Gadde et al., "Effects of low-dose, controlled-release, phentermine plus topiramate combination on weight and associated comorbidities in overweight and obese adults (CONQUER): a randomised, placebo-controlled, phase 3 trial," Lancet, Apr. 16, 2011, 377(9774):1341-1352.
Garvey et al., "Two-year sustained weight loss and metabolic benefits with controlled-release phentermine/topiramate in obese and overweight adults (SEQUEL): a randomized, placebo-controlled, phase 3 extension study," Am. J. Clin. Nutrition, Feb. 2012, 95(2):297-308.
Gostout et al., "Delayed Gastric Emptying as a Proposed Mechanism of Action Dui Intragastric Balloon Therapy: Results of a Prospective Controlled Study," Abstract No. O.955, Presented at Proceedings of the International Federation for the Surgery of Obesity and Metabolic Disorders 20th World Congress, Vienna, Austria, Aug. 26-29, 2015; Obes. Surgery, 2015, 25(Suppl 1):S129-S130.
Goyal et al., "Endoscopic Bariatric Therapies," Curr. Gastroenterol. Reports, Jun. 2016, 18(6):26, 8 pages.
Greenway et al., "Effect of naltrexone plus bupropion on weight loss in overweight and obese adults (COR-I): a multicentre, randomised, double-blind, placebo-controlled, phase 3 trial," Lancet, Aug. 21, 2010, 376(9741):595-605.
Halawi et al., "Effects of liraglutide on weight, satiation, and gastric functions in obesity: a randomised, placebo-controlled pilot trial," Lancet Gastroenterol. Hepatology, Sep. 25, 2017, 2(12):890-899.
Hall et al., "Models Use Leptin and Calculus to Count Calories," Cell Metabolism, Jan. 7, 2009, 9(1):3-4.
Hall, "Diet Versus Exercise in "The Biggest Loser" Weight Loss Competition," Obesity, May 2013, 21(5):957-959.
Harris, "Role of set-point theory in regulation of body weight," FASEB Journal, Dec. 1990, 4(15):3310-3318.
Hensrud et al., "Extreme obesity: a new medical crisis in the United States," Mayo Clin. Proceedings, Oct. 1, 2006, 81(10 Suppl):S5-S10.
Hervey, "Regulation of Energy Balance," Nature, May 17, 1969, 222:629-631.
Hollander et al., "Role of Orlistat in the Treatment of Obese Patients With Type 2 Diabetes: A 1-year randomized double-blind study," Diabetes Care, Aug. 1998, 21(8):1288-1294.
Ikegami et al., "Abstract 12631: Peripheral Gamma-aminobutyric Acid(gaba) Signaling in Brown Adipose Tissue Induces Metabolic Dysfunction in Obesity," Circulation, Nov. 10, 2015, 132(S3):A12631.
Irving et al., "Nutrient Transporter Expression in the Jejunum in Relation to Body Mass Index in Patients Undergoing Bariatric Surgery," Nutrients, Oct. 29, 2016, 8(11):683, 12 pages.
Jensen et al., "2013 AHA/ACC/TOS Guideline for the Management of Overweight and Obesity in Adults: A Report of the American College of Cardiology/American Heart Association Task Force on Practice Guidelines and The Obesity Society," J. Am. Coll. Cardiology, Jul. 1, 2014, 63(25 Pt B):2985-3023.
Johannsen et al., "Metabolic Slowing with Massive Weight Loss despite Preservation of Fat-Free Mass," J. Clin. Endocrinol. Metabolism, Jul. 2012, 97(7):2489-2496.
Karra et al., "The role of peptide YY in appetite regulation and obesity," J. Physiology, Jan. 2009, 587(Pt. 1):19-25.
Keesey et al., "Body Energy Homeostasis," Appetite, Nov. 2008, 51(3):442-445.
Klok et al., "The role of leptin and ghrelin in the regulation of food intake and body weight in humans: a review," Obes. Reviews, Jan. 2007, 8(1):21-34.
Kumar et al., "Efficacy Comparison of Medications Approved for Chronic Weight Management," Obesity, Apr. 2015, 23(Suppl 1):S4-S7.
Locke et al., "Genetic studies of body mass index yield new insights for obesity biology," Nature, Feb. 12, 2015, 518(7538):197-206.
Lynch et al., "Branched-chain ammo acids in metabolic signalling and insulin resistance," Nat. Rev. Endocrinology, Oct. 7, 2014, 10(12):723-736.
Nauck et al., "Efficacy and Safety Comparison of Liraglutide, Cilimepiride, and Placebo, All in Combination with Metformin, in Type 2 Diabetes: the LEAD (Liraglutide Effect and Action in Diabetes)-2 study," Diabetes Care, Jan. 2009. 32(1):84-90.
Newgard et al., "A Branched-Chain Amino Acid-Related Metabolic Signature that Differentiates Obese and Lean Humans and. Contributes to Insulin Resistance," Cell Metabolism, Apr. 8, 2009, 9(4):311-326.
Ng et al., "Global, regional, and national prevalence of overweight and obesity in children and adults during 1980-2013: a systematic analysis for the Global Burden of Disease Study 2013," Lancet, Aug. 30, 2014, 384(9945):766-781.
Olson et al., "Alloisoleucine Differentiates the Branched-chain Ammoacidemia of Zucker and Dietary Obese Rats," Obesity, May 2014, 22(5):1212-1215.

(56) References Cited

OTHER PUBLICATIONS

Papierkowski et al., "Monocirboxylic short-chain fatty acids C2-C6 in serum of obese children," Acta Paediatr. Acade. Sci. Hung., 1975, 16(3-4):277-280.

PCT International Preliminary Report on Patentability in International Appln. No. PCT/US2018/062217, dated May 26, 2020 8 pages.

PCT International Search Report and Written Opinion in International Appln. No. PCT/US2018/062217, dated Feb. 8, 2019, 10 pages.

Pi-Sunyer et al., "A Randomized, Controlled Trial of 3.0 mg of Liraglutide in Weight Management," N. Engl. J. Medicine, Jul. 2, 2015, 373(1):11-22.

Rauschert et al. "Metabolomic Biomarkers for Obesity in Humans: A Short Review," Ann. Nutr. Metabolisim, Oct. 2, 2014, 64(3-4):314-324.

Riebe et al., "Updating ACSM's Recommendations for Exercise Preparticipation Health Screening," Med. Sci. Sports Exercise, Nov. 2015, 47(11):2473-2479.

Roberts et al., "β-Aminoisobutyric Acid Induces Browning of White Fat and Hepatic β-Oxidation and Is Inversely Correlated with Cardiometabolic Risk Factors," Cell Metabolism, Jan. 7, 2014, 19(1):96-108.

Rodriguez et al., "Obesity changes the human gut mycobiome," Sci. Reports, Oct. 12, 2015, 5:14600, 15 pages.

Rosenbaum et al., "Low Dose Leptin Administration Reverses Effects of Sustained Weight-Reduction on Energy Expenditure and Circulating Concentrations of Thyroid Hormones," J. Clin. Endocrinol. Metabolism, May 2002, 87(5):2391-2394.

Rosenbaum et al., "Low-dose leptin reverses skeletal muscle, autonomic, and neuroendocrine adaptations to maintenance of reduced weight," J. Clin. Investigation, Dec. 2005, 115(12):3579-3586.

Saunders et al., "Pharmacotherapy for Obesity,'" Endocrinol. Metab. Clin. North America, Sep. 2016, 45(3)521-538.

Sjostrom et al., "Randomised placebo-controlled trial of orlistat for weight loss and prevention of weight regain in obese patients," Lancet, Jul. 18, 1998, 352(9123):167-172.

Smith et al., "Multicenter, Placebo-Controlled Trial of Lorcaserin for Weight Management," N. Engl. J. Medicine, Jul. 15, 2010, 363(3):245-256.

Speliotes et al., "Association analyses of 249,796 individuals reveal 18 new loci associated with body mass indexc" Nat. Genetics, Oct. 10, 2010, 42(11):937-948.

Van Can et al., "Effects of the once-daily GLP-1 analog liraglutide on gastric emptying, glyceithe parameters, appetite and energy metabolism in obese, non-diabetic adults," Int. J. Obesity, Jun. 2014, 38(6):784-793.

Vazquez et al., "Gastric Sensorimotor Functions and Hormone Profile in Normal Weight, Overweight, and Obese People," Gastroenterology, Dec. 2006, 131(6):1717-1724.

Wadden et al., Weight Loss With Naltrexone SR/Bupropion SR Combination Therapy as an Adjunct to Behavior Modification: The COR-BMOD Trial, Obesity, Jan. 2011, 19(1):110-120.

Watanabe et al., "Serotonin Improves High Fat Diet Induced Obesity in Mice," PLoS One, Jan. 14, 2016, 11(1):e0147143, 14 pages.

Wyatt et al., "Update on Treatment Strategies for Obesity," J. Clin. Endocrinol. Metabolism, Apr. 2013, 98(4):1299-1306.

Zigmond et al., "The Hospital Anxiety and Depression Scale," Acta Psychiatr. Scandinavica, Jun. 1983, 67(6):361-370.

EP Supplementary Partial Search Report in European Appln. No. 18881422.2, dated Jul. 5, 2021, 18 pages.

Roberts et al., "Tailoring pharmacotherapy to specific eating behaviours in obesity: Can recommendations for personalised therapy be made from the current data?," Acta Diabetologica, Apr. 19, 2017, 54(8):715-725.

Solas et al., "Precision Obesity Treatments Including Pharmacogenetic and Nutrigenetic Approaches," Trends Pharmacol. Sciences, May 25, 2016, 37(7):575-593.

* cited by examiner

| Obesity Phenotype Group | Pharmacotherapy | Exemplary Intervention |
|---|---|---|
| 1: low satiation | appetite suppressant in combination with an anticonvuslant | phentermine-topiramate |
| 2: low satiety | appetite suppressant | lorcaserin |
| 3: behavioral eating | GLP-1 agonist | liraglutide |
| 4: large fasting gastric volume | antidepressant in combination with an opioid antagonist | naltrexone-bupropion |
| 5: mixed | antidepressant in combination with an opioid antagonist | naltrexone-bupropion |
| 6: low resting energy expenditure | combination based on the combination of phenotypes | |
| | appetite suppressant in combination with physical activity | phentermine + increased physical activity |

{ obesity analyte signature

FIG. 12A

METHODS AND MATERIALS FOR ASSESSING AND TREATING OBESITY

CROSS-REFERENCE TO RELATED APPLICATIONS

This application is a National Stage application under 35 U.S.C. § 371 of International Application No. PCT/US2018/062217, having an International Filing Date of Nov. 21, 2018, which claims the benefit of U.S. Patent Application Ser. No. 62/589,915, filed on Nov. 22, 2017. The disclosure of the prior application is considered part of (and is incorporated by reference in) the disclosure of this application.

STATEMENT REGARDING FEDERAL FUNDING

This invention was made with government support under DK067071 and DK084567 awarded by the National Institutes of Health. The government has certain rights in the invention.

BACKGROUND

1. Technical Field

This document relates to methods and materials for assessing and/or treating obesity in mammals (e.g., humans). For example, this document provides methods and materials for determining an obesity analyte signature of a mammal. For example, this document provides methods and materials for determining an obesity phenotype of a mammal. For example, this document provides methods and materials for using one or more interventions (e.g., one or more pharmacological interventions) to treat obesity and/or obesity-related comorbidities in a mammal (e.g., a human) identified as being likely to respond to a particular intervention (e.g., a pharmacological intervention).

2. Background Information

Obesity prevalence continues to increase worldwide (Ng et al., 2014 *Lancet* 384:766-81) and, in the United States, 69% of adults are overweight or obese (Flegal et al., 2012 *JAMA* 307:491-497). Estimated costs to the healthcare system are more than $550 billion annually. Increased severity of obesity correlates with a higher prevalence of the associated co-morbidities. Likewise, obesity increases the risk of premature mortality (Hensrud et al., 2006 *Mayo Clinic Proceedings* 81(10 Suppl):S5-10). Obesity affects almost every organ system in the body and increases the risk of numerous diseases including type 2 diabetes mellitus, hypertension, dyslipidemia, cardiovascular disease, and cancer. It is estimated that a man in his twenties with a BMI over 45 will have a 22% reduction (13 years) in life expectancy.

SUMMARY

Despite advances in understanding aspects of obesity pathophysiology, weight loss with current treatments including diet, exercise, medications, endoscopy, and surgery is highly variable (Acosta et al., 2014 *Gut* 63:687-95). For example, some obese patients specifically respond to particular medications, and can lose as much weight and with fewer side effects than bariatric surgery. There is a need to be able to identify which intervention(s) an obese patient is likely to respond to in order to be able to select the right intervention for the right patient based on his/her pathophysiology.

This document provides methods and materials for assessing and/or treating obesity in mammals (e.g., humans). In some cases, this document provides methods and materials for identifying an obese mammal as being responsive to a pharmacological intervention (e.g., by identifying the mammal as having a pharmacotherapy responsive obesity analyte signature), and administering one or more interventions (e.g., pharmacological interventions) to treat the mammal. For example, a sample obtained from an obese mammal can be assessed to determine if the obese mammal is likely to be responsive to pharmacological intervention based, at least in part, on an obesity phenotype, which is based, at least in part, on an obesity analyte signature in the sample. As demonstrated herein, a distinct obesity analyte signature is present in each of six main obesity phenotype groups: 1) low satiation, 2) low satiety (e.g., rapid return to hunger), 3) behavioral eating (identified by questionnaire), 4) large fasting gastric volume, 5) mixed, and 6) low resting energy expenditure group; and each obesity phenotype is likely to be responsive to one or more particular interventions (e.g., pharmacological intervention, surgical intervention, weight loss device, diet intervention, behavior intervention, and/or microbiome intervention).

Having the ability to identify which intervention(s) an obese patient is likely to respond to provides a unique and unrealized opportunity to provide an individualized approach in selecting obesity treatments.

In general, one aspect of this document features a method for treating obesity in a mammal. The method includes, or consists essentially of, identifying the mammal as having an intervention responsive obesity analyte signature in a sample obtained from the mammal; and administering an intervention to the mammal. The sample can be a blood sample, a saliva sample, a urine sample, a breath sample, or a stool sample. For example, the sample can be a breath sample. For example, the method sample can be a stool sample. The mammal can be a human. In some cases, the obesity analyte signature can include 1-methylhistine, serotonin, glutamine, gamma-amino-n-butyric-acid, isocaproic, allo-isoleucine, hydroxyproline, beta-aminoisobutyric-acid, alanine, hexanoic, tyrosine, phenylalanine, ghrelin, and peptide tyrosine tyrosine (PYY). The intervention can be effective to reduce the total body weight of said mammal by at least 4%. The intervention can be effective to reduce the total body weight of said mammal by from about 3 kg to about 100 kg. The intervention can be effective to reduce the waist circumference of said mammal by from about 1 inches to about 10 inches. The identifying step also can include obtaining results from a Hospital Anxiety and Depression Scale (HADS) questionnaire and/or a Three Factor Eating questionnaire (TFEQ). In some cases, the obesity analyte signature can include a presence of serotonin, glutamine, isocaproic, allo-isoleucine, hydroxyproline, beta-aminoisobutyric-acid, alanine, hexanoic, tyrosine, and PYY, and an absence of (e.g., lacks the presence of) 1-methylhistine, gamma-amino-n-butyric-acid, phenylalanine, ghrelin; the HADS questionnaire result does not indicate an anxiety subscale; and the mammal can be responsive to intervention with phentermine-topiramate pharmacotherapy and/or lorcaserin pharmacotherapy. In some cases, the obesity analyte signature can include a presence of 1-methylhistine, allo-isoleucine, hydroxyproline, beta-aminoisobutyric-acid, alanine, and phenylalanine, and an absence of serotonin, glutamine, gamma-amino-n-butyric-acid, isocaproic, hexanoic, tyrosine, ghrelin, and PYY; the HADS questionnaire result not indicate an anxiety subscale; and the mammal can be responsive to intervention with liraglutide pharmacotherapy. In some cases, the obesity analyte signature can include a presence of serotonin, and an absence of 1-methylhistine, glutamine, gamma-amino-n-butyric-acid, isocaproic, allo-isoleucine, hydroxyproline, beta-aminoisobutyric-acid, alanine, hexanoic, tyrosine, phenylalanine, ghrelin, and PYY; the HADS questionnaire result indicates an anxiety subscale; and the mammal can be responsive to intervention with naltrexone-bupropion pharmacotherapy. In some cases, the obesity analyte signature can include a presence of 1-methylhistine, glutamine, gamma-amino-n-butyric-acid, isocaproic, allo-isoleucine, beta-aminoisobutyric-acid, alanine, hexanoic, tyrosine, phenylalanine, PYY, and an absence of serotonin, hydroxyproline, and ghrelin; the HADS questionnaire result indicates an anxiety subscale; and the mammal can be responsive to intervention with naltrexone-bupropion pharmacotherapy. In some cases, the obesity analyte signature can include a presence of 1-methylhistine, serotonin, glutamine, gamma-amino-n-butyric-acid, isocaproic, allo-isoleucine, alanine, tyrosine, ghrelin, PYY, and an absence of hydroxyproline, beta-aminoisobutyric-acid, hexanoic, and phenylalanine; the HADS questionnaire result indicates an anxiety subscale; and the mammal can be responsive to intervention with phentermine pharmacotherapy. In some cases, the obesity analyte signature can include HTR2C, GNB3, FTO, iso-caproic acid, beta-aminoisobutyricacid, butyric, allo-isoleucine, tryptophan, and glutamine. The identifying step also can include obtaining results from a HADS questionnaire. In some cases, the obesity analyte signature can include the presence of a single nucleotide polymorphism (SNP) in HTR2C, POMC, NPY, AGRP, MC4R, GNB3, SERT, and/or BDNF; the HADS questionnaire result does not indicate an anxiety subscale; and the mammal can be responsive to intervention with phentermine-topiramate pharmacotherapy and/or lorcaserin pharmacotherapy. The SNP can be rs1414334. In some cases, the obesity analyte signature can include the presence of a SNP in PYY, GLP-1, MC4R, GPBAR1, TCF7L2, ADRA2A,PCSK, and/or TMEM18; the HADS questionnaire result not indicate an anxiety subscale; and the mammal can be responsive to intervention with liraglutide pharmacotherapy. The SNP can be rs7903146. In some cases, the obesity analyte signature can include presence of a SNP in SLC6A4/SERT, and/or DRD2; the HADS questionnaire result indicates an anxiety subscale; and the mammal can be responsive to intervention with naltrexone-bupropion pharmacotherapy. The SNP can be rs4795541. In some cases, the obesity analyte signature can include the presence of a SNP in TCF7L2, UCP3, and/or ADRA2A; the HADS questionnaire result indicates an anxiety subscale; and the mammal can be responsive to intervention with naltrexone-bupropion pharmacotherapy. The SNP can be rs1626521. In some cases, the obesity analyte signature can include the presence of a SNP in FTO, LEP, LEPR, UCP1, UCP2, UCP3, ADRA2, KLF14, NPC1, LYPLAL1, ADRB2, ADRB3, and/or BBS1; the HADS questionnaire result indicates an anxiety subscale; and the mammal can be responsive to intervention with phentermine pharmacotherapy. The SNP can be rs2075577.

In another aspect, this document features a method for treating obesity in a mammal. The method includes, or consists essentially of, administering an intervention to a mammal that was identified as having an intervention responsive obesity analyte signature. The mammal can be a human. The obesity analyte signature can include 1-methylhistine, serotonin, glutamine, gamma-amino-n-butyric-acid, isocaproic, allo-isoleucine, hydroxyproline, beta-aminoisobutyric-acid, alanine, hexanoic, tyrosine, phenylalanine, ghrelin, and peptide tyrosine tyrosine (PYY). The intervention can be effective to reduce the total body weight of said mammal by at least 4%. The intervention can be effective to reduce the total body weight of said mammal by from about 3 kg to about 100 kg. The intervention can be effective to reduce the waist circumference of said mammal by from about 1 inches to about 10 inches. The identifying step also can include obtaining results from a Hospital Anxiety and Depression Scale (HADS) questionnaire. In some cases, the obesity analyte signature can include a presence of serotonin, glutamine, isocaproic, allo-isoleucine, hydroxyproline, beta-aminoisobutyric-acid, alanine, hexanoic, tyrosine, and PYY, and an absence of (e.g., lacks the presence of) 1-methylhistine, gamma-amino-n-butyric-acid, phenylalanine, ghrelin; the HADS questionnaire result does not indicate an anxiety subscale; and the mammal can be responsive to intervention with phentermine-topiramate pharmacotherapy and/or lorcaserin pharmacotherapy. In some cases, the obesity analyte signature can include a presence of 1-methylhistine, allo-isoleucine, hydroxyproline, beta-aminoisobutyric-acid, alanine, and phenylalanine, and an absence of serotonin, glutamine, gamma-amino-n-butyric-acid, isocaproic, hexanoic, tyrosine, ghrelin, and PYY; the HADS questionnaire result not indicate an anxiety subscale; and the mammal can be responsive to intervention with liraglutide pharmacotherapy. In some cases, the obesity analyte signature can include a presence of serotonin, and an absence of 1-methylhistine, glutamine, gamma-amino-n-butyric-acid, isocaproic, allo-isoleucine, hydroxyproline, beta-aminoisobutyric-acid, alanine, hexanoic, tyrosine, phenylalanine, ghrelin, and PYY; the HADS questionnaire result indicates an anxiety subscale; and the mammal can be responsive to intervention with naltrexone-bupropion pharmacotherapy. In some cases, the obesity analyte signature can include a presence of 1-methylhistine, glutamine, gamma-amino-n-butyric-acid, isocaproic, allo-isoleucine, beta-aminoisobutyric-acid, alanine, hexanoic, tyrosine, phenylalanine, PYY, and an absence of serotonin, hydroxyproline, and ghrelin; the HADS questionnaire result indicates an anxiety subscale; and the mammal can be responsive to intervention with naltrexone-bupropion pharmacotherapy. In some cases, the obesity analyte signature can include a presence of 1-methylhistine, serotonin, glutamine, gamma-amino-n-butyric-acid, isocaproic, allo-isoleucine, alanine, tyrosine, ghrelin, PYY, and an absence of hydroxyproline, beta-aminoisobutyric-acid, hexanoic, and phenylalanine; the HADS questionnaire result indicates an anxiety subscale; and the mammal can be responsive to intervention with phentermine pharmacotherapy.

In another aspect, this document features a method for identifying an obese mammal as being responsive to treatment with an intervention. The method includes, or consists essentially of, determining an obesity analyte signature in a sample obtained from a mammal, where the obesity analyte signature can include 1-methylhistine, serotonin, glutamine, gamma-amino-n-butyric-acid, isocaproic, allo-isoleucine, hydroxyproline, beta-aminoisobutyric-acid, alanine, hexanoic, tyrosine, phenylalanine, ghrelin, and PYY; and classifying the mammal as having an intervention responsive obesity analyte signature based upon the presence and absence of analytes in the obesity analyte signature. The mammal can be a human. The sample can be a blood sample, a saliva sample, a urine sample, a breath sample, or a stool sample. For example, the sample can be a breath sample. For example, the method sample can be a stool sample. The method also can include obtaining results from a HADS questionnaire. In some cases, the obesity analyte signature can include a presence of serotonin, glutamine, isocaproic, allo-isoleucine, hydroxyproline, beta-aminoisobutyric-acid, alanine, hexanoic, tyrosine, and PYY, and an absence of (e.g., lacks the presence of) 1-methylhistine, gamma-amino-n-butyric-acid, phenylalanine, ghrelin; the HADS questionnaire result does not indicate an anxiety subscale; and the mammal can be responsive to intervention with phentermine-topiramate pharmacotherapy and/or lorcaserin pharmacotherapy. In some cases, the obesity analyte signature can include a presence of 1-methylhistine, allo-isoleucine, hydroxyproline, beta-aminoisobutyric-acid, alanine, and phenylalanine, and an absence of serotonin, glutamine, gamma-amino-n-butyric-acid, isocaproic, hexanoic, tyrosine, ghrelin, and PYY; the HADS questionnaire result not indicate an anxiety subscale; and the mammal can be responsive to intervention with liraglutide pharmacotherapy. In some cases, the obesity analyte signature can include a presence of serotonin, and an absence of 1-methylhistine, glutamine, gamma-amino-n-butyric-acid, isocaproic, allo-isoleucine, hydroxyproline, beta-aminoisobutyric-acid, alanine, hexanoic, tyrosine, phenylalanine, ghrelin, and PYY; the HADS questionnaire result indicates an anxiety subscale; and the mammal can be responsive to intervention with naltrexone-bupropion pharmacotherapy. In some cases, the obesity analyte signature can include a presence of 1-methylhistine, glutamine, gamma-amino-n-butyric-acid, isocaproic, allo-isoleucine, beta-aminoisobutyric-acid, alanine, hexanoic, tyrosine, phenylalanine, PYY, and an absence of serotonin, hydroxyproline, and ghrelin; the HADS questionnaire result indicates an anxiety subscale; and the mammal can be responsive to intervention with naltrexone-bupropion pharmacotherapy. In some cases, the obesity analyte signature can include a presence of 1-methylhistine, serotonin, glutamine, gamma-amino-n-butyric-acid, isocaproic, allo-isoleucine, alanine, tyrosine, ghrelin, PYY, and an absence of hydroxyproline, beta-aminoisobutyric-acid, hexanoic, and phenylalanine; the HADS questionnaire result indicates an anxiety subscale; and the mammal can be responsive to intervention with phentermine pharmacotherapy.

In another aspect, this document features a identifying an obese mammal as being responsive to treatment with an intervention. The method includes, or consists essentially of, determining an obesity analyte signature in a sample obtained from an obese mammal mammal, where the obesity analyte signature includes HTR2C, GNB3, FTO, isocaproic acid, beta-aminoisobutyricacid, butyric, allo-isoleucine, tryptophan, and glutamine; obtaining results from a HADS questionnaire; and classifying the mammal as having a intervention responsive obesity analyte signature based upon the presence and absence of analytes in the obesity analyte signature. The mammal can be a human. The sample can be a blood sample, a saliva sample, a urine sample, a breath sample, or a stool sample. In some cases, the sample can be a breath sample. In some cases, the sample can be a stool sample. In some cases, the obesity analyte signature can include the presence of a SNP in HTR2C, POMC, NPY, AGRP, MC4R, GNB3, SERT, and/or BDNF; the HADS questionnaire result can not indicate an anxiety subscale; and the mammal can be classified as being responsive to intervention with phentermine-topiramate pharmacotherapy and/or lorcaserin pharmacotherapy. The SNP can be rs1414334. In some cases, the obesity analyte signature can include the presence of a SNP in PYY, GLP-1, MC4R, GPBAR1, TCF7L2, ADRA2A,PCSK, and/or TMEM18; the HADS questionnaire result can not indicate an anxiety subscale; and the mammal can be classified as being responsive to intervention with liraglutide pharmacotherapy. The SNP can be rs7903146. In some cases, the obesity analyte signature can include the presence of a SNP in SLC6A4/ SERT, and/or DRD2; the HADS questionnaire result can indicate an anxiety subscale; and the mammal can be classified as being responsive to intervention with naltrexone-bupropion pharmacotherapy. The SNP can be rs4795541. In some cases, the obesity analyte signature can include the presence of a SNP in TCF7L2, UCP3, and/or ADRA2A; the HADS questionnaire result can indicate an anxiety subscale; and the mammal can be classified as being responsive to intervention with naltrexone-bupropion pharmacotherapy. The SNP can be rs1626521. In some cases, the obesity analyte signature can include the presence of a SNP in FTO, LEP, LEPR, UCP1, UCP2, UCP3, ADRA2, KLF14, NPC1, LYPLAL1, ADRB2, ADRB3, and/or BBS1; the HADS questionnaire result can indicate an anxiety subscale; and the mammal can be classified as being responsive to intervention with phentermine pharmacotherapy. The SNP can be rs2075577.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 12A-12C are a flow charts showing exemplary treatment interventions for obesity groups identified based, at least in part, on a patient's obesity analyte signature.

DETAILED DESCRIPTION

Figure 1A:
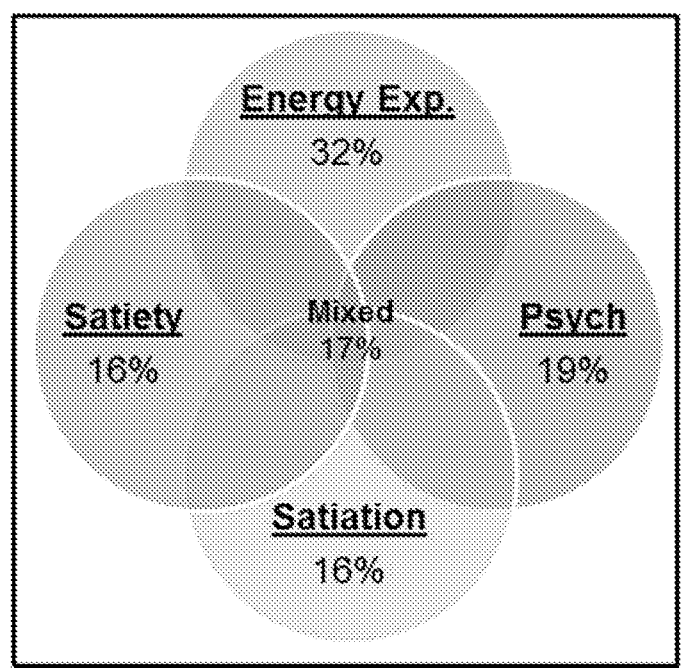
FIGS. 1A-1E shows classifications of obesity. A) 180 Caucasian participants with obesity (BMI>30 kg·m2) were sub classified into a) abnormal satiation (16%), abnormal satiety (16%), abnormal hedonic/behavior (19%), slow metabolism (32%) and mixed group (17%). The subgroups have unique characteristics as shown for food intake until reaching fullness tested in a nutrient drink test (B), gastric emptying rate, surrogate of satiety (C) and anxiety levels, surrogate of hedonic (D), and slow metabolism (E) based on the subgroups and gender (blue=females, red=males).
Figure 1B:
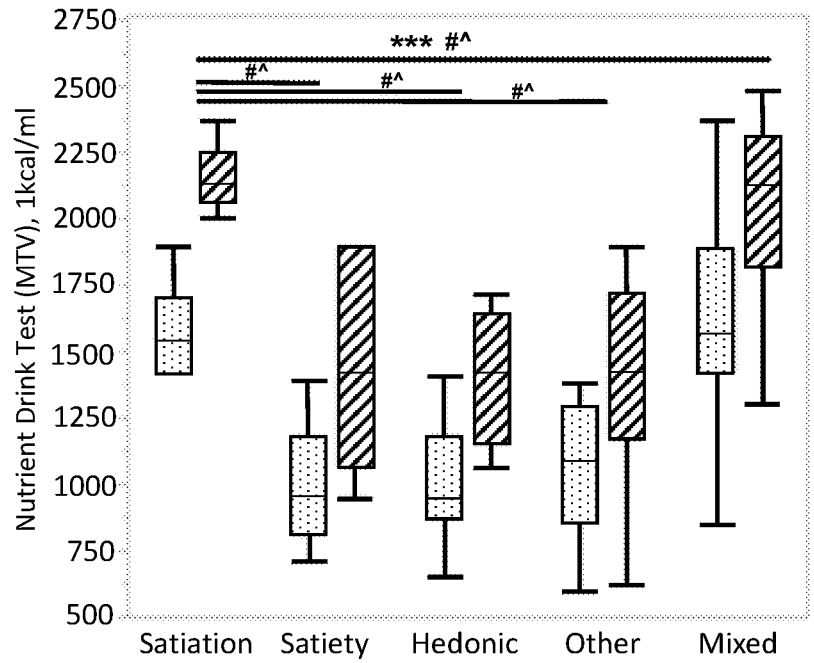
Figure 1C:
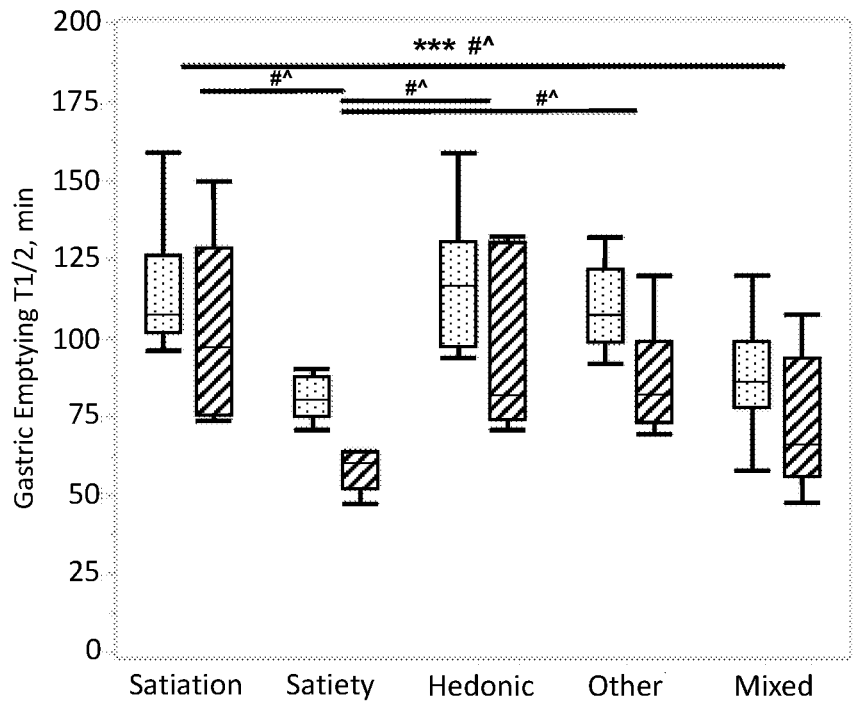
Figure 1D:
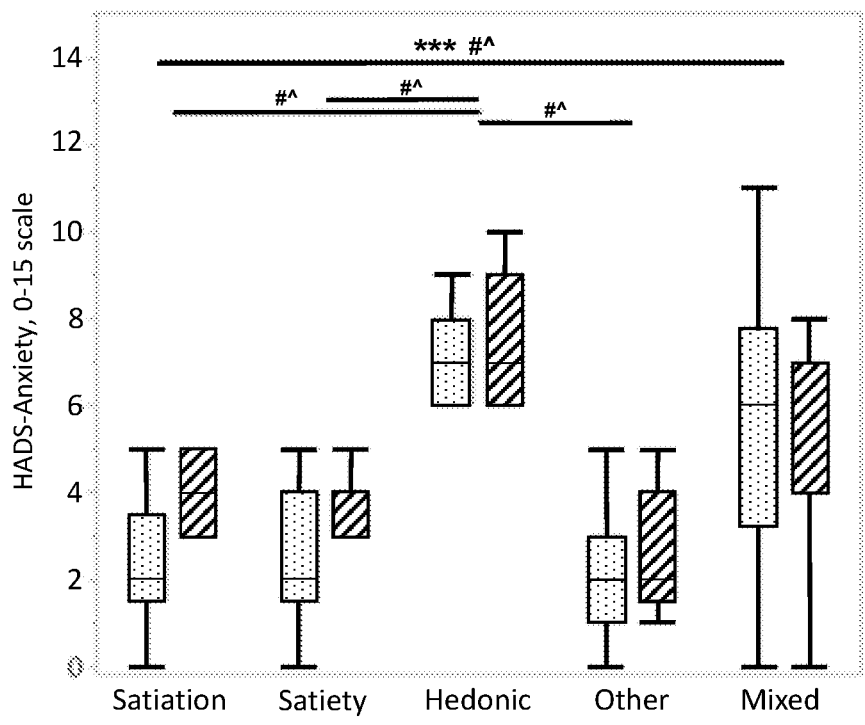
Figure 1E:
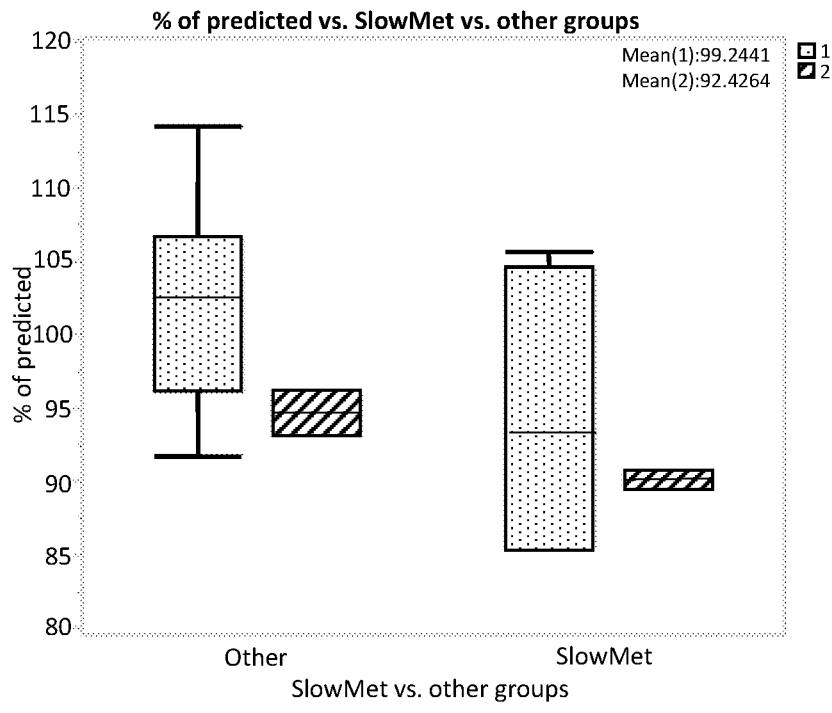

This document provides methods and materials for assessing and/or treating obesity in mammals (e.g., humans). In some cases, this document provides methods and materials for identifying an obese mammal as being responsive to a pharmacological intervention, and administering one or more pharmacological interventions to treat the mammal. For example, a sample obtained from an obese mammal can be assessed to determine if the obese mammal is likely to be responsive to intervention (e.g., pharmacological intervention, surgical intervention, weight loss device, diet intervention, behavior intervention, and/or microbiome intervention) based, at least in part, on an obesity phenotype, which is based, at least in part, on an obesity analyte signature in the sample. An obesity analyte signature can include the presence, absence, or level (e.g., concentration) of two or more (e.g., three, four, five, six, seven, eight, nine, 10, 11, 12, 13, 14, 15, 16, 17, 18, 19, 20, or more) obesity analytes (e.g., biomarkers associated with obesity). In some cases, an obesity analyte signature can include 14 obesity analytes. For example, a pharmacotherapy responsive obesity analyte signature can be based, at least in part, on the presence, absence, or level of 14 obesity analytes. In some cases, an obesity analyte signature can include 9 obesity analytes. For example, a pharmacotherapy responsive obesity analyte signature can be based, at least in part, on the presence, absence, or level of 9 obesity analytes. In some cases, the methods and materials described herein can be used to predict further weight loss response (e.g., during the course of an obesity treatment). In some cases, the methods and materials described herein can be used to prevent plateaus (e.g., during the course of an obesity treatment). In some cases, the methods and materials described herein can be used to enhance weight loss maintenance (e.g., during the course of an obesity treatment). In some cases, the methods and materials described herein can be used to treat patients unable to lose and maintain weight with diet and exercise alone.

As described herein, a distinct obesity analyte signature can be present in each of six main obesity phenotypes: Group 1) low satiation, Group 2) low satiety (e.g., rapid return to hunger), Group 3) behavioral eating (e.g., as identified by questionnaire), Group 4) large fasting gastric volume, Group 5) mixed, and Group 6) low resting energy expenditure group. Also described herein, the obesity analyte signature in sample obtained from an obese mammal (and thus the obesity phenotype) can be used to predict intervention responsiveness. In some cases, obesity phenotype groups can be simplified as: 1) high energy intake, 2) behavioral/emotional eating, and 3) low energy expenditure; or can be simplified as 1) low satiation (fullness), 2) low satiety (return to hunger), 3) behavioral/emotional eating, 4) low energy expenditure, 5) mixed, and 6) other.

When treating obesity in a mammal (e.g., a human) as described herein, the mammal can also have one or more obesity-related (e.g., weight-related) co-morbidities. Examples of weight-related co-morbidities include, without limitation, hypertension, type 2 diabetes, dyslipidemia, obstructive sleep apnea, gastroesophageal reflux disease, weight baring joint arthritis, cancer, non-alcoholic fatty liver disease, nonalcoholic steatohepatitis, depression, anxiety, and atherosclerosis (coronary artery disease and/or cerebrovascular disease). In some cases, the methods and materials described herein can be used to treat one or more obesity-related co-morbidities.

When treating obesity in a mammal (e.g., a human) as described herein, the treatment can be effective to reduce the weight, reduce the waist circumference, slow or prevent weight gain of the mammal, improve the hemoglobin A1c, and/or improve the fasting glucose. For example, treatment described herein can be effective to reduce the weight (e.g., the total body weight) of an obese mammal by at least 3% (e.g., at least 5%, at least 8%, at least 10%, at least 12%, at least 15%, at least 18%, at least 20%, at least 22%, at least 25%, at least 28%, at least 30%, at least 33%, at least 36%, at least 39%, or at least 40%). For example, treatment described herein can be effective to reduce the weight (e.g., the total body weight) of an obese mammal by from about 3% to about 40% (e.g., from about 3% to about 35%, from about 3% to about 30%, from about 3% to about 25%, from about 3% to about 20%, from about 3% to about 15%, from about 3% to about 10%, from about 3% to about 5%, from about 5% to about 40%, from about 10% to about 40%, from about 15% to about 40%, from about 20% to about 40%, from about 25% to about 40%, from about 35% to about 40%, from about 5% to about 35%, from about 10% to about 30%, from about 15% to about 25%, or from about 18% to about 22%). For example, treatment described herein can be effective to reduce the weight (e.g., the total body weight) of an obese mammal by from about 3 kg to about 100 kg (e.g., about 5 kg to about 100 kg, about 8 kg to about 100 kg, about 10 kg to about 100 kg, about 15 kg to about 100 kg, about 20 kg to about 100 kg, about 30 kg to about 100 kg, about 40 kg to about 100 kg, about 50 kg to about 100 kg, about 60 kg to about 100 kg, about 70 kg to about 100 kg, about 80 kg to about 100 kg, about 90 kg to about 100 kg, about 3 kg to about 90 kg, about 3 kg to about 80 kg, about 3 kg to about 70 kg, about 3 kg to about 60 kg, about 3 kg to about 50 kg, about 3 kg to about 40 kg, about 3 kg to about 30 kg, about 3 kg to about 20 kg, about 3 kg to about 10 kg, about 5 kg to about 90 kg, about 10 kg to about 75 kg, about 15 kg to about 50 kg, about 20 kg to about 40 kg, or about 25 kg to about 30 kg). For example, treatment described herein can be effective to reduce the waist circumference of an obese mammal by from about 1 inches to about 10 inches (e.g., about 1 inches to about 9 inches, about 1 inches to about 8 inches, about 1 inches to about 7 inches, about 1 inches to about 6 inches, about 1 inches to about 5 inches, about 1 inches to about 4 inches, about 1 inches to about 3 inches, about 1 inches to about 2 inches, about 2 inches to about 10 inches, about 3 inches to about 10 inches, about 4 inches to about 10 inches, about 5 inches to about 10 inches, about 6 inches to about 10 inches, about 7 inches to about 10 inches, about 8 inches to about 10 inches, about 9 inches to about 10 inches, about 2 inches to about 9 inches, about 3 inches to about 8 inches, about 4 inches to about 7 inches, or about 5 inches to about 7 inches). In some cases, the methods and materials described herein can be used to improve (e.g., increase or decrease) the hemoglobin A1c of an obese mammal (e.g., an obese mammal having type 2 diabetes mellitus) to from about 0.4% to about 3% (e.g., from about 0.5% to about 3%, from about 1% to about 3%, from about 1.5% to about 3%, from about 2% to about 3%, from about 2.5% to about 3%, from about 0.4% to about 2.5%, from about 0.4% to about 2%, from about 0.4% to about 1.5%, from about 0.4% to about 1%, from about 0.5% to about 2.5%, or from about 1% to about 2%) hemoglobin A1c. In some cases, the methods and materials described herein can be used to improve (e.g., increase or decrease) the fasting glucose of an obese mammal (e.g., an obese mammal having type 2 diabetes mellitus) to from about 10 mg/dl to about 200 mg/dl (e.g., from about 15 mg/dl to about 200 mg/dl, from about 25 mg/dl to about 200 mg/dl, from about 50 mg/dl to about 200 mg/dl, from about 75 mg/dl to about 200 mg/dl, from about 100 mg/dl to about 200 mg/dl, from about 125 mg/dl to about 200 mg/dl, from about 150 mg/dl to about 200 mg/dl, from about 175 mg/dl to about 200 mg/dl, from about 190 mg/dl to about 200 mg/dl, from about 10 mg/dl to about 175 mg/dl, from about 10 mg/dl to about 150 mg/dl, from about 10 mg/dl to about 125 mg/dl, from about 10 mg/dl to about 100 mg/dl, from about 10 mg/dl to about 75 mg/dl, from about 10 mg/dl to about 50 mg/dl, from about 10 mg/dl to about 25 mg/dl, or from about 10 mg/dl to about 20 mg/dl) glucose.

Any type of mammal can be assessed and/or treated as described herein. Examples of mammals that can be assessed and/or treated as described herein include, without limitation, primates (e.g., humans and monkeys), dogs, cats, horses, cows, pigs, sheep, rabbits, mice, and rats. In some cases, the mammal can a human. In some cases, a mammal can be an obese mammal. For example, obese humans can be assessed for intervention (e.g., a pharmacological intervention) responsiveness, and treated with one or more interventions as described herein. In cases where mammal is a human, the human can be of any race. For example, a human can be Caucasian or Asian.

Any appropriate method can be used to identify a mammal as being overweight (e.g., as being obese). In some cases, calculating body mass index (BMI), measuring waist and/or hip circumference, health history (e.g., weight history, weight-loss efforts, exercise habits, eating patterns, other medical conditions, medications, stress levels, and/or family health history), physical examination (e.g., measuring your height, checking vital signs such as heart rate blood pressure, listening to your heart and lungs, and examining your abdomen), percentage of body fat and distribution, percentage of visceral and organs fat, metabolic syndrome, and/or obesity related comorbidities can be used to identify mammals (e.g., humans) as being obese. For example, a BMI of greater than about 30 $kg/m^2$ can be used to identify mammals (e.g., Caucasian humans) as being obese. For example, a BMI of greater than about 27 $kg/m^2$ with a co-morbidity can be used to identify mammals (e.g., Asian humans) as being obese.

Once identified as being obese, a mammal can be assessed to determine whether or not it is likely to respond to one or more interventions (e.g., pharmacological intervention, surgical intervention, weight loss device, diet intervention, behavior intervention, and/or microbiome intervention). For example, a sample obtained from the mammal can be assessed for pharmacological intervention responsiveness. As described herein, a panel of obesity analytes in a sample obtained from an obese mammal can be used to determine an obesity analyte signature of the mammal, and can be used in to determine an obesity phenotype of the mammal.

Any appropriate sample from a mammal (e.g., a human) having obesity can be assessed as described herein. In some cases, a sample can be a biological sample. In some cases, a sample can contain obesity analytes (e.g., DNA, RNA, proteins, peptides, metabolites, hormones, and/or exogenous compounds (e.g. medications)). Examples of samples that can be assessed as described herein include, without limitation, fluid samples (e.g., blood, serum, plasma, urine, saliva, sweat, or tears), breath samples, cellular samples (e.g., buccal samples), tissue samples (e.g., adipose samples), stool samples, gastro samples, and intestinal mucosa samples. In some cases, a sample (e.g., a blood sample) can be collected while the mammal is fasting (e.g., a fasting sample such as a fasting blood sample). In some cases, a sample can be processed (e.g., to extract and/or isolate obesity analytes). For example, a serum sample can be obtained from an obese mammal and can be assessed to determine if the obese mammal is likely to be responsive to one or more interventions (e.g., pharmacological intervention, surgical intervention, weight loss device, diet intervention, behavior intervention, and/or microbiome intervention) based, at least in part, on an obesity phenotype, which is based, at least in part, on an obesity analyte signature in the sample. For example, a urine sample can be obtained from an obese mammal and can be assessed to determine if the obese mammal is likely to be responsive to pharmacological intervention based, at least in part, on an obesity phenotype, which is based, at least in part, on an obesity analyte signature in the sample.

An obesity analyte signature can include any appropriate analyte. Examples of analytes that can be included in an obesity analyte signature described herein include, without limitation, DNA, RNA, proteins, peptides, metabolites, hormones, and exogenous compounds (e.g. medications). An obesity analyte signature can be evaluated using any appropriate methods. For example, metabolomics, genomics, microbiome, proteomic, peptidomics, and behavioral questionnaires can be used to evaluate and/or identify an obesity analyte signature described herein.

Any appropriate method can be used to identify an obesity phenotype as described herein. In some cases, the obesity phenotype can be identified as described in the Examples. For example, the obesity phenotype can be identified by determining the obesity analyte signature in a sample (e.g., in a sample obtained from an obese mammal). In some cases, the obesity analyte signature can be obtained by detecting the presence, absence, or level of one or more metabolites, detecting the presence, r absence, or level one or more peptides (e.g., gastrointestinal peptides), and/or detecting the presence, absence, or level of one or more single nucleotide polymorphisms (SNPs).

A metabolite can be any metabolite that is associated with obesity. In some cases, a metabolite can be an amino- compound. In some cases, a metabolite can be a neurotransmitter. In some cases, a metabolite can be a fatty acid (e.g., a short chain fatty acid). In some cases, a metabolite can be an amino compound. In some cases, a metabolite can be a bile acid. In some cases, a metabolite can be a compound shown in Table 2. Examples of metabolites that can be used to determine the obesity analyte signature in a sample (e.g., in a sample obtained from an obese mammal) include, without limitation, 1-methylhistine, serotonin, glutamine, gamma-amino-n-butyric-acid, isocaproic, allo-isoleucine, hydroxyproline, beta-aminoisobutyric-acid, alanine, hexanoic, tyrosine, phenylalanine γ-aminobutyric acid, acetic, histidine, LCA, ghrelin, ADRA2A, cholesterol, glucose, acetylcholine, propionic, CDCA, PYY, ADRA2C, insulin, adenosine, isobutyric, 1-methylhistidine, DCA, CCK, GNB3, glucagon, aspartate, butyric, 3-methylhistidine, UDCA, GLP-1, FTO, leptin, dopamine, valeric, asparagine, HDCA, GLP-2, MC4R, adiponectin, D-serine, isovaleric, phosphoethanolamine, CA, glucagon, TCF7L2, glutamate, hexanoic, arginine, GLCA, oxyntomodulin, 5-HTTLPR, glycine, octanoic, carnosine, GCDCA, neurotensin, HTR2C, myristic, taurine, GDCA, FGF, UCP2, norepinephrine, palmitic, anserine, GUDCA, GIP, UCP3, serotonin, palmitoleic, serine, GHDCA, OXM, GPBAR1, taurine, palmitelaidic, glutamine, GCA, FGF19, NR1H4, stearic, ethanolamine, TLCA, FGF21, FGFR4, oleic, glycine, TCDCA, LDL, elaidic, aspartic acid, TDCA, insulin, GLP-1, linoleic, sarcosine, TUDCA, glucagon, CCK, a-linolenic, proline, THDCA, amylin, arachidonic, alpha-aminoadipic-acid, TCA, pancreatic polypeptide, eicosapentaenoic, DHCA, neurotensin, docosahexaenoic, alpha-amino-N-butyric-acid, THCA, ornithine, GLP-1 receptor, triglycerides, cystathionine 1, GOAT, cystine, DPP4, lysine, methionine, valine, isoleucine, leucine, homocystine, tryptophan, citrulline, glutamic acid, beta-alanine, threonine, hydroxylysine 1, acetone, and acetoacetic acid. In some cases, an obesity analyte signature can include 1-methylhistine, serotonin, glutamine, gamma-amino-n-butyric-acid, isocaproic, allo-isoleucine, hydroxyproline, beta-aminoisobutyric-acid, alanine, hexanoic, tyrosine, and phenylalanine.

A gastrointestinal peptide can be any gastrointestinal peptide that is associated with obesity. In some cases, a gastrointestinal peptide can be a peptide hormone. In some cases, a gastrointestinal peptide can be released from gastrointestinal cells in response to feeding. In some cases, a gastrointestinal peptide can be a peptide shown in Table 2. Examples of gastrointestinal peptides that can be used to determine the obesity analyte signature in a sample (e.g., in a sample obtained from an obese mammal) include, without limitation, ghrelin, peptide tyrosine tyrosine (PYY), cholecystokinin (CCK), glucagon-like peptide-1 (GLP-1), GLP-2, glucagon, oxyntomodulin, neurotensin, fibroblast growth factor (FGF), GIP, OXM, FGF19, FGF19, and pancreatic polypeptide.

A SNP can be any SNP that is associate with obesity. A SNP can be in a coding sequence (e.g., in a gene) or a non-coding sequence. For example, in cases where a SNP is in a coding sequence, the coding sequence can be any appropriate coding sequence. In some cases, a coding sequence that can include a SNP associated with obesity can be a gene shown in Table 2. Examples of coding sequences that a SNP associated with obesity can be in or near include, without limitation, ADRA2A, ADRA2C, GNB3, FTO, MC4R, TCF7L2, 5-HTTLPR, HTR2C, UCP2, UCP3, GPBAR1, NR1H4, FGFR4, PYY, GLP-1, CCK, leptin, adiponectin, neurotensin, ghrelin, GLP-1 receptor, GOAT, DPP4, POMC, NPY, AGRP, SERT, BDNF, SLC6A4, DRD2, LEP, LEPR, UCP1, KLF14, NPC1, LYPLAL1, ADRB2, ADRB3, BBS1, ACSL6, ADARB2, ADCY8, ADH1B, AJAP1, ATP2C2, ATP6V0D2, C21orf7, CAMKMT, CAP2, CASC4, CD48, CDC42SE2, CDYL, CES5AP1, CLMN, CNPY4, COL19A1, COL27A1, COL4A3, CORO1C, CPZ, CTIF, DAAM2, DCHS2, DOCKS, EGFLAM, FAM125B, FAM71E2, FRMD3, GALNTL4, GLT1D1, HHAT, KRT23, LHPP, LINC00578, LINC00620, LIPC, LOC100128714, LOC100287160, LOC100289473, LOC100293612|LINC00620, LOC100506869, LOC100507053, LOC100507053|ADH1A, LOC100507053|ADH, LOC100507443, LOC100996571|CYYR1, LOC152225, LOC255130, LPAR1, LUZP2, MCM7, MICAL3, MMS19, MYBPC1, NR2F2-AS1, NSMCE2, NTN1, O3FAR1, OAZ2, OSBP2, P4HA2, PADI1, PARD3B, PARK2, PCDH15, PIEZO2, PKIB, PRH1-PRR4, PTPRD, RALGPS1|ANGPTL2, RPS24P10, RTN4RL1, RYR2, SCN2A, SEMA3C, SEMA5A, SFMBT2, SGCG, SLC22A15, SLC2A2, SLCO1B1, SMOC2, SNCAIP, SNX18, SRRM4, SUSD1, TBC1D16, TCERG1L, TENM3, TJP3, TLL1, TMEM9B, TPM1, VTI1A, VWF, WWOX, WWTR1, ZFYVE28, ZNF3, ZNF609, and ZSCAN21. In some cases, a SNP can be a SNP shown in Table 3. Examples of SNPS that can be used to determine the obesity analyte signature in a sample (e.g., in a sample obtained from an obese mammal) include, without limitation, rs657452, rs11583200, rs2820292, rs11126666, rs11688816, rs1528435, rs7599312, rs6804842, rs2365389, rs3849570, rs16851483, rs17001654, rs11727676, rs2033529, rs9400239, rs13191362, rs1167827, rs2245368, rs2033732, rs4740619, rs6477694, rs1928295, rs10733682, rs7899106, rs17094222, rs11191560, rs7903146, rs2176598, rs12286929, rs11057405, rs10132280, rs12885454, rs3736485, rs758747, rs2650492, rs9925964, rs1000940, rs1808579, rs7243357, rs17724992, rs977747, rs1460676, rs17203016, rs13201877, rs1441264, rs7164727, rs2080454, rs9914578, rs2836754, rs492400, rs16907751, rs9374842, rs9641123, rs9540493, rs4787491, rs6465468, rs7239883, rs3101336, rs12566985, rs12401738, rs11165643, rs17024393, rs543874, rs13021737, rs10182181, rs1016287, rs2121279, rs13078960, rs1516725, rs10938397, rs13107325, rs2112347, rs205262, rs2207139, rs17405819, rs10968576, rs4256980, rs11030104, rs3817334, rs7138803, rs12016871, rs12429545, rs11847697, rs7141420, rs16951275, rs12446632, rs3888190, rs1558902, rs12940622, rs6567160, rs29941, rs2075650, rs2287019, rs3810291, rs7715256, rs2176040, rs6091540, rs1800544, Ins-Del-322, rs5443, rs1129649, rs1047776, rs9939609, rs17782313, rs7903146, rs4795541, rs3813929, rs518147, rs1414334, rs659366, -3474, rs2075577, rs15763, rs1626521, rs11554825, rs4764980, rs434434, rs351855, and rs2234888.

An obesity analyte signature described herein can include any appropriate combination of analytes. For example, when an obesity analyte signature includes 14 analytes, the analytes can include 1-methylhistine, serotonin, glutamine, gamma-amino-n-butyric-acid, isocaproic, allo-isoleucine, hydroxyproline, beta-aminoisobutyric-acid, alanine, hexanoic, tyrosine, phenylalanine, ghrelin, and PYY. For example, when an obesity analyte signature includes 9 analytes, the analytes can include HTR2C, GNB3, FTO, isocaproic, beta-aminoisobutyric-acid, butyric, allo-isoleucine, tryptophan, and glutamine.

Any appropriate method can be used to detect the presence, absence, or level of an obesity analyte within a sample. For example, mass spectrometry (e.g., triple-stage quadrupole mass spectrometry coupled with ultra-performance liquid chromatography (UPLC)), radioimmuno assays, and enzyme-linked immunosorbent assays can be used to determine the presence, absence, or level of one or more analyte in a sample.

In some cases, identifying the obesity phenotype can include obtaining results from all or part of one or more questionnaires. A questionnaire can be associated with obesity. In some cases, a questionnaire can be answered the time of the assessment. In some cases, a questionnaire can be answered prior to the time of assessment. For example, when a questionnaire is answered prior to the time of the assessment, the questionnaire results can be obtained by reviewing a patient history (e.g., a medical chart). A questionnaire can be a behavioral questionnaire (e.g., psychological welfare questionnaires, alcohol use questionnaires, eating behavior questionnaires, body image questionnaires, physical activity level questionnaire, and weight management questionnaires. Examples of questionnaires that can be used to determine the obesity phenotype of a mammal (e.g., an obese mammal) include, without limitation, The Hospital Anxiety and Depression Scale (HADS) questionnaire, The Hospital Anxiety and Depression Inventory questionnaire, The Questionnaire on Eating and Weight Patterns, The Weight Efficacy Life-Style (WEL) Questionnaire, The Multidimensional Body-Self Relations Questionnaire, The Questionnaire on Eating and Weight Patterns-Revised, The Weight Efficacy Life-Style, Physical Activity Level-item Physical Activity Stages of Change Questionnaire, The Exercise Regulations Questionnaire (BREQ-3), Barriers to Being Active Quiz, and The Three Factor Eating Questionnaire (TFEQ). For example, a questionnaire can be a HADS questionnaire. For example, a questionnaire can be a TFEQ.

In some cases, an obesity analyte signature can include the presence of serotonin, glutamine, isocaproic, allo-isoleucine, hydroxyproline, beta-aminoisobutyric-acid, alanine, hexanoic, tyrosine, and PYY. For example, an obesity phenotype Group 1 can have an obesity analyte signature that includes the presence of serotonin, glutamine, isocaproic, allo-isoleucine, hydroxyproline, beta-aminoisobutyric-acid, alanine, hexanoic, tyrosine, and PYY. For example, an obesity phenotype Group 1 can have an obesity analyte signature that has an absence of (e.g., lacks the presence of) 1-methylhistine, gamma-amino-n-butyric-acid, phenylalanine, ghrelin, and includes a HADS questionnaire result that does not indicate an anxiety subscale (HADS-A; e.g., includes a HADS-A questionnaire result).

In some cases, an obesity analyte signature can include the presence of 1-methylhistine, allo-isoleucine, hydroxyproline, beta-aminoisobutyric-acid, alanine, and phenylalanine. For example, an obesity phenotype Group 2 can have an obesity analyte signature that includes the presence of -methylhistine, allo-isoleucine, hydroxyproline, beta-aminoisobutyric-acid, alanine, and phenylalanine. For example, an obesity phenotype Group 2 can have an obesity analyte signature that has an absence of (e.g., lacks the presence of) serotonin, glutamine, gamma-amino-n-butyric-acid, isocaproic, hexanoic, tyrosine, ghrelin, PYY, and does not include a HADS questionnaire result that indicates an anxiety subscale (e.g., does not include a HADS-A questionnaire result)

In some cases, an obesity analyte signature can include the presence of serotonin, and can include a HADS-A questionnaire. For example, an obesity phenotype Group 3 can have an obesity analyte signature that includes serotonin and includes a HADS-A questionnaire result. For example, an obesity phenotype Group 3 can have an obesity analyte signature that has an absence of (e.g., lacks the presence of) 1-methylhistine, glutamine, gamma-amino-n-butyric-acid, isocaproic, allo-isoleucine, hydroxyproline, beta-aminoisobutyric-acid, alanine, hexanoic, tyrosine, phenylalanine, ghrelin, and PYY.

In some cases, an obesity analyte signature can include the presence of 1-methylhistine, glutamine, gamma-amino-n-butyric-acid, isocaproic, allo-isoleucine, beta-aminoisobutyric-acid, alanine, hexanoic, tyrosine, phenylalanine, PYY, and includes a HADS-A questionnaire result. For example, an obesity phenotype Group 4 can have an obesity analyte signature that includes 1-methylhistine, glutamine, gamma-amino-n-butyric-acid, isocaproic, allo-isoleucine, beta-aminoisobutyric-acid, alanine, hexanoic, tyrosine, phenylalanine, PYY, and includes a HADS-A questionnaire result. For example, an obesity phenotype Group 4 can have an obesity analyte signature that has an absence of (e.g., lacks the presence of) serotonin, hydroxyproline, and ghrelin.

In some cases, an obesity analyte signature can include the presence of serotonin, beta-aminoisobutyric-acid, alanine, hexanoic, phenylalanine, and includes a HADS-A questionnaire. For example, an obesity phenotype Group 5 can have an obesity analyte signature that includes the presence of serotonin, beta-aminoisobutyric-acid, alanine, hexanoic, phenylalanine, and includes a HADS-A questionnaire result. For example, an obesity phenotype Group 5 can have an obesity analyte signature that has an absence of (e.g., lacks the presence of) 1-methylhistine, glutamine, gamma-amino-n-butyric-acid, isocaproic, allo-isoleucine, and hydroxyproline.

In some cases, an obesity analyte signature can include the presence of 1-methylhistine, serotonin, glutamine, gamma-amino-n-butyric-acid, isocaproic, allo-isoleucine, alanine, tyrosine, ghrelin, PYY, and includes a HADS-A questionnaire result. For example, an obesity phenotype Group 6 can have an obesity analyte signature that includes the presence of 1-methylhistine, serotonin, glutamine, gamma-amino-n-butyric-acid, isocaproic, allo-isoleucine, alanine, tyrosine, ghrelin, PYY, and includes a HADS-A questionnaire result. For example, an obesity phenotype Group 6 can have an obesity analyte signature that has an absence of (e.g., lacks the presence of) hydroxyproline, beta-aminoisobutyric-acid, hexanoic, and phenylalanine.

In some cases, identifying the obesity phenotype also can include identifying one or more additional variables and/or one or more additional assessments. For example, identifying the obesity phenotype also can include assessing the microbiome of a mammal (e.g., an obese mammal). For example, identifying the obesity phenotype also can include assessing leptin levels. For example, identifying the obesity phenotype also can include assessing the metabolome of a mammal (e.g., an obese mammal). For example, identifying the obesity phenotype also can include assessing the genome of a mammal (e.g., an obese mammal). For example, identifying the obesity phenotype also can include assessing the proteome of a mammal (e.g., an obese mammal). For example, identifying the obesity phenotype also can include assessing the peptidome of a mammal (e.g., an obese mammal).

Figure 12B:
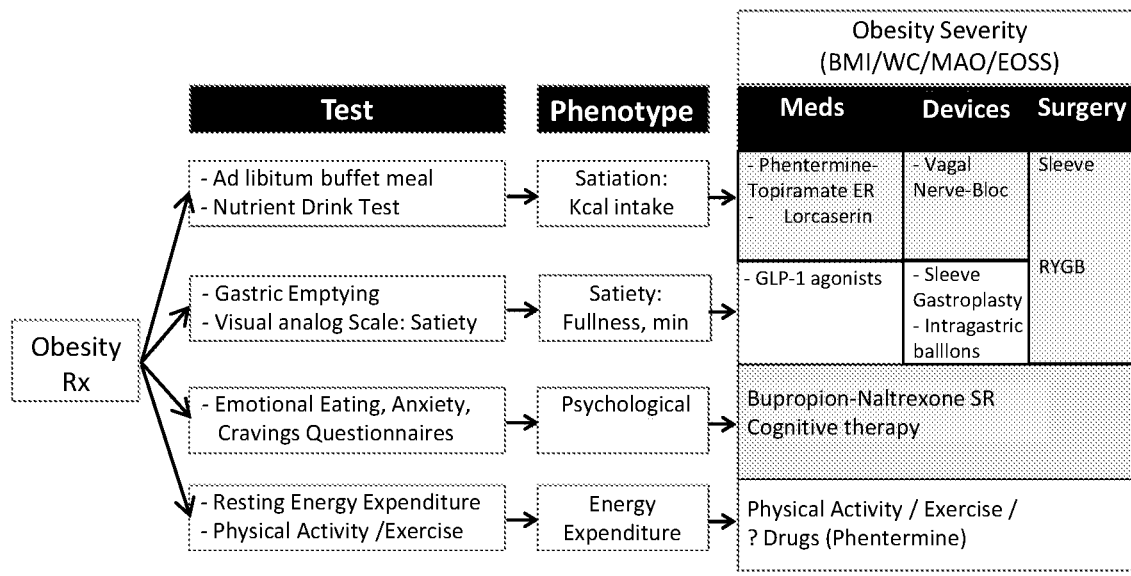
Figure 12C:
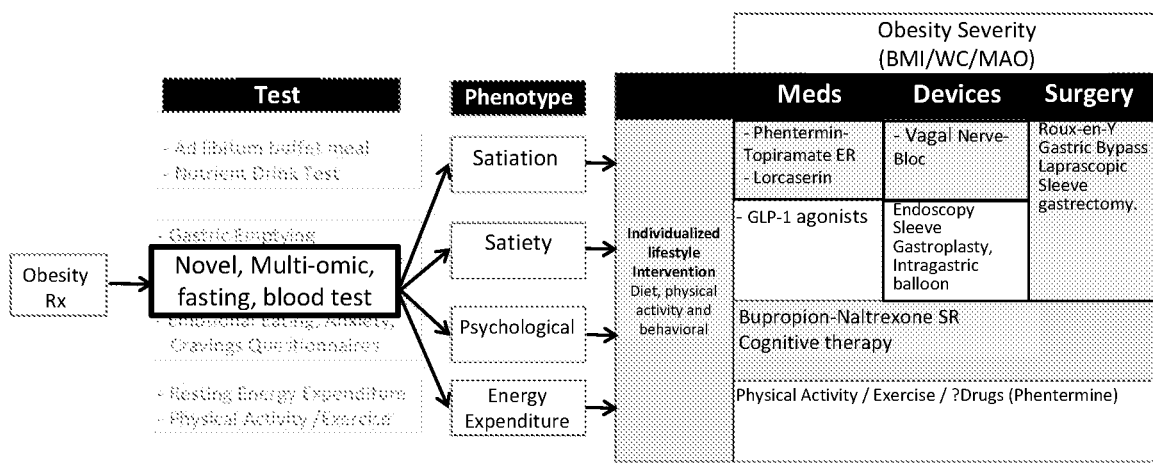

Once the obesity phenotype of the mammal has been identified, the mammal can be assessed to determine intervention (e.g., pharmacological intervention, surgical intervention, weight loss device, diet intervention, behavior intervention, and/or microbiome intervention) responsiveness, and a treatment option for the mammal can be selected. In some cases, the obesity phenotype of a mammal can be used to select a treatment options as shown in FIG. 12, and as set forth in Table 1.

TABLE 1

Treatment options.

| Obesity Phenotype Group | Pharmacotherapy | Exemplary Intervention |
|---|---|---|
| Pharmacotherapy Intervention: FDA approved medications | | |
| 1: low satiation | appetite suppressant in combination with an anticonvuslant | phentermine-topiramate |
|  | appetite suppressant | lorcaserin, desvenlafaxine |
| 2: low satiety | GLP-1 analog, GLP-1 receptor agonist, amylin analogs | liraglutide, exenatide, metformin, pramlitide |
| 3: behavioral eating | antidepressant in combination with an opioid antagonist | naltrexone-bupropion |
| 4: large fasting gastric volume | antidepressant in combination with an opioid antagonist | naltrexone-bupropion |
| 5: mixed | combination based on the combination of phenotypes | |
| 6: low resting energy expenditure | appetite suppressant in combination with physical activity | phentermine + increased physical activity |
| Pharmacotherapy Intervention: medications not-FDA approved | | |
| 1: low satiation | melanocortin receptor | MK-0493 |
|  |  | RM-493 |
|  | appetite suppressants |  |
|  | CCK analogs |  |
| 2: low satiety | GLP-1 analog - GLP-1 receptor agonists - GLP-1/glucagon coagonists | semaglutide, |
|  | PYY analogs - Y receptors agonists/antagonists | velnerperit (s-2367) obinepitide |
|  | Oxyntomodulin analogs |  |
|  | Ghrelin antagonists |  |
|  | TGR5 agonists | Conjugated bile acids |
|  | FGF-19/21 analogs |  |
|  | FXR agonists |  |
|  | GRP-119 |  |
|  | GRP-120 |  |
|  | Combinations of these meds |  |
| 3: behavioral eating | antidepressant | bupropion + zonisamide |
|  | opioid antagonist | Tesofensine |
|  | anti-anxiety | Buspirone |
|  | cannabionids antagonists | rimonabant |
| 4: large fasting gastric volume | ghrelin antagonist |  |
| 5: mixed | combination based on the combination of phenotypes |  |
| 6: low resting energy expenditure | leptin modulators | metroleptin |
|  | MetAP2 inhibitors | ZGN-1061, beloranib |
|  | B3 agonists | mirabegron |
| Weight Loss Devices | | |
| Obesity Phenotype Group | Surgical procedure and devices | Exemplary Intervention |
| 1: low satiation | vagal stimulant | V-bloc |
|  | mouth occupying devices | Retrograde gastric pacing |
|  | intra-gastric space occupying devices | Smartbyte ™ |
|  |  | gastric balloon |
|  | sleeve gastroplasty |  |
| 2: low satiety | duodenal bypass or mucosal resurfacing (example: ablation) | Endobarrier |
|  | intra-gastric space occupying devices | gastric balloon |
|  | malabsorptive procedures | transpyloric shuttle |

TABLE 1-continued

Treatment options.

| | | |
|---|---|---|
| 3: behavioral eating | gastric emptying devices | Aspire assist |
| 4: large fasting gastric volume | gastric emptying devices | Aspire assist |
| | intra-gastric space occupying devices | gastric balloon |
| | sleeve gastroplasty | |
| 5: mixed | combination based on the combination of phenotypes | |
| 6: low resting energy expenditure | | phentermine + increased physical activity |
| 1: low satiation | Gastric occupying space | Transoral endoscopic restrictive implant system |
| | Brain stimulant | deep transcranial magnetic stimulation |
| 2: low satiety | Duodenal bypass or mucosal resurfacing (example: ablation) | Fractyl - duodenal ablation |
| | Intra-gastric space occupying devices | Intragastric balloons - adjustable |
| | Malabsorptive procedures | Magnet therapy (Incision-less Anastomosis System) |
| 3: behavioral eating | | |
| 4: large fasting gastric volume | Intra-gastric space occupying devices | Intragastric balloons - adjustable |
| | Gastric plications | POSE |
| 5: mixed | combination based on the combination of phenotypes | |
| 6: low resting energy expenditure | Muscle stimulants | Pulse muscle stimulator |
| | Energy trackers | |
| | Cold inducers (stimulates BAT) | Cold vests |

Diet Intervention

| Obesity Phenotype Group | Diet | Exemplary Intervention |
|---|---|---|
| 1: low satiation | Slow eating | |
| | volumetric diet | Legumes, fruits, beans, whole grains |
| | high fat - high protein - low carb | Atkins diet |
| | | Keto diet |
| 2: low satiety | High protein - low carb - average fat | Paleo-diet |
| | | Mediterranean diet |
| 3: behavioral eating | Schedule 2-3 meals daily. No snacks | Crash diet |
| 4: large fasting gastric volume | High soluble fiber | Fiber supplements, |
| 5: mixed | | |
| 6: low resting energy expenditure | Low fat - Average protein, average carbs | 13-day Metabolism diet |

Surgical Intervention

| Obesity Phenotype Group | Surgical procedure | Exemplary Intervention |
|---|---|---|
| 1: low satiation | Restrictive procedures | Sleeve |
| | | RYGB |
| | | Lap-band |
| 2: low satiety | Malabsorptive procedures | RYGB - Sleeve plus duodenal switch |
| 3: behavioral eating | | |
| 4: large fasting gastric volume | Restrictive procedures | Sleeve |
| | | RYGB |
| 5: mixed | | |
| 6: low resting energy expenditure | Malabsorptive procedures | RYGB - duodenal switch |

Microbiome Intervention

| Obesity Phenotype Group | Microbiome status | Exemplary Intervention |
|---|---|---|
| 1: low satiation | Microbiota inflammatory inducing | Reduce microbiome LPS induction |
| 2: low satiety | Low microbiome richness | Increase richness of microbiota (probiotic mix) to increase SCFA in GI lumen |
| 3: behavioral eating | Serotonin producing bacteria | Reduced serotonin producing bacteria: restore *Bacteroides* spp |
| 4: large fasting gastric volume | Low microbiome richness | Increase primary BA microbiota |
| 5: mixed | | |
| 6: low resting energy expenditure | Low fatty acids producing bacteria | Increase fatty acid metabolism producing bacteria |

Individualized pharmacological interventions for the treatment of obesity (e.g., based on the obesity phenotypes as described herein) can include any one or more (e.g., 1, 2, 3, 4, 5, 6, or more) pharmacotherapies (e.g., individualized pharmacotherapies). A pharmacotherapy can include any appropriate pharmacotherapy. In some cases, a pharmacotherapy can be an obesity pharmacotherapy. In some cases, a pharmacotherapy can be an appetite suppressant. In some cases, a pharmacotherapy can be an anticonvulsant. In some cases, a pharmacotherapy can be a GLP-1 agonist. In some cases, a pharmacotherapy can be an antidepressant. In some cases, a pharmacotherapy can be an opioid antagonist. In some cases, a pharmacotherapy can be a controlled release pharmacotherapy. For example, a controlled release pharmacotherapy can be an extended release (ER) and/or a slow release (SR) pharmacotherapy. In some cases, a pharmacotherapy can be a lipase inhibitor. In some cases, a pharmacotherapy can be a DPP4 inhibitor. In some cases, a pharmacotherapy can be a SGLT2 inhibitor. In some cases, a pharmacotherapy can be a dietary supplement. Examples of pharmacotherapies that can be used in an individualized pharmacological intervention as described herein include, without limitation, orlistat, phentermine, topiramate, lorcaserin, naltrexone, bupropion, liraglutide, exenatide, metformin, pramlitide, Januvia, canagliflozin, dexamphetamines, prebiotics, probiotics, Ginkgo biloba, and combinations thereof. For example, combination pharmacological interventions for the treatment of obesity (e.g., based on the obesity phenotypes as described herein) can include phentermine-topiramate ER, naltrexone-bupropion SR, phentermine-lorcaserin, lorcaserin-liraglutide, and lorcaserin-januvia. A pharmacotherapy can be administered using any appropriate methods. In some cases, pharmacotherapy can be administered by continuous pump, slow release implant, intra-nasal administered, intra-oral administered, and/or topical administered. In some cases, a pharmacotherapy can be administered as described elsewhere (see, e.g., Sjostrom et al., 1998 *Lancet* 352:167-72; Hollander et al., 1998 *Diabetes Care* 21:1288-94; Davidson et al., 1999 *JAMA* 281:235-42; Gadde et al., 2011 *Lancet* 377:1341-52; Smith et al., 2010 *New Engl. J Med.* 363:245-256; Apovian et al., 2013 *Obesity* 21:935-43; Pi-Sunyer et al., 2015 *New Engl. J Med.* 373:11-22; and Acosta et al., 2015 *Clin Gastroenterol Hepatol.* 13:2312-9).

Once a mammal is identified as being responsive to one or more interventions (e.g., pharmacological intervention, surgical intervention, weight loss device, diet intervention, behavior intervention, and/or microbiome intervention) based, at least in part, on an obesity phenotype, which is based, at least in part, on an obesity analyte signature in the sample, the mammal can be administered or instructed to self-administer one or more individualized pharmacotherapies.

When a mammal is identified as having an obesity phenotype that is responsive to treatment with one or more pharmacotherapies, the mammal can be administered or instructed to self-administer one or more pharmacotherapies. For example, when a mammal is identified as having a low satiation (Group 1) phenotype, based, at least in part, on an obesity analyte signature, the mammal can be administered or instructed to self-administer phentermine-topiramate (e.g., phentermine-topiramate ER) to treat the obesity. For example, when a mammal is identified as having a low satiation (Group 1) phenotype, based, at least in part, on an obesity analyte signature, the mammal can be administered or instructed to self-administer lorcaserin to treat the obesity. For example, when a mammal is identified as having a low satiety (Group 2) phenotype, based, at least in part, on an obesity analyte signature, the mammal can be administered or instructed to self-administer liraglutide to treat the obesity. For example, when a mammal is identified as having a behavioral eating (Group 3) phenotype, based, at least in part, on an obesity analyte signature, the mammal can be administered or instructed to self-administer naltrexone-bupropion (e.g., naltrexone-bupropion SR) to treat the obesity. For example, when a mammal is identified as having a large fasting gastric volume (Group 4) phenotype, based, at least in part, on an obesity analyte signature, the mammal can be administered or instructed to self-administer naltrexone-bupropion (e.g., naltrexone-bupropion SR) to treat the obesity. For example, when a mammal is identified as having a low resting energy expenditure (Group 6) phenotype, based, at least in part, on an obesity analyte signature, the mammal can be administered or instructed to self-administer phentermine, and can be instructed to increase physical activity to treat the obesity.

In some cases, one or more pharmacotherapies described herein can be administered to an obese mammal as a combination therapy with one or more additional agents/therapies used to treat obesity. For example, a combination therapy used to treat an obese mammal (e.g., an obese human) can include administering to the mammal one or more pharmacotherapies described herein and one or more obesity treatments such as weight-loss surgeries (e.g., gastric bypass surgery, laparoscopic adjustable gastric banding (LAGB), biliopancreatic diversion with duodenal switch, and a gastric sleeve), vagal nerve blockade, endoscopic devices (e.g. intragastric balloons or endoliners, magnets), endoscopic sleeve gastroplasty, and/or gastric or duodenal ablations. For example, a combination therapy used to treat an obese mammal (e.g., an obese human) can include administering to the mammal one or more pharmacotherapies described herein and one or more obesity therapies such as exercise modifications (e.g., increased physical activity), dietary modifications (e.g., reduced-calorie diet), behavioral modifications, commercial weight loss programs, wellness programs, and/or wellness devices (e.g. dietary tracking devices and/or physical activity tracking devices). In cases where one or more pharmacotherapies described herein are used in combination with one or more additional agents/therapies used to treat obesity, the one or more additional agents/therapies used to treat obesity can be administered/performed at the same time or independently. For example, the one or more pharmacotherapies described herein can be administered first, and the one or more additional agents/therapies used to treat obesity can be administered/performed second, or vice versa.

This document provides methods and materials for identifying one or more analytes associated with obesity. In some cases, analytes associated with obesity can be used in an obesity analyte signature as described herein. For example, one or more analytes associated with obesity can be identified by using a combined logit regression model. In some cases, a combined logit regression model can include stepwise variable selection (e.g., to identify variables significantly associated with a specific obesity phenotype). For example, one or more analytes associated with obesity can be identified as described in, for example, the Examples section provided herein.

The invention will be further described in the following examples, which do not limit the scope of the invention described in the claims.

EXAMPLES

Example 1: Identification of Obesity Biomarkers

Obesity phenotypes were associated with higher BMI, distinguish obesity phenotypes, and can be used to predict responsiveness to obesity pharmacotherapy and endoscopic devices (see, e.g., Acosta et al., 2015 *Gastroenterology* 148:537-546). In this study, biomarkers specific to each obesity phenotype were identified using metabolomics.

The overall cohort demographics [median (IQR)] were age 36 (28-46) years, BMI 35 (32-38) kg/m2, 75% females, 100% Caucasians. The groups based on phenotype > or <75% ile were not statistically different for body weight, waist circumference, hip circumference, fasting glucose. The group distribution in this cohort was: abnormal satiation (16%), abnormal satiety (16%), abnormal hedonic/psych (19%), slow metabolism/energy expenditure (32%), and mixed group (17%) (FIG. 1A). FIGS. 1B-E illustrate summarize characteristics of the quantitative changes in the subgroups: the satiation group consumed 591 (60%) more calories prior to reaching fullness; the satiety group emptied half of the solid 300 kcal meal 34 min (30%) faster; the hedonic group reported 2.8 times higher levels of anxiety; the slow metabolism group has 10% decreased predicted resting energy expenditure than other groups. These average differences were in comparison to the other groups, but excluding the group with participants with a mixed or overlapping phenotype.

Gastrointestinal Traits (Phenotypes) Associated with Obesity

Gastrointestinal functions, satiation, and satiety were characterized in 509 participants across the normal weight to obesity spectrum. Obesity was associated with decreased satiation (higher caloric intake before feeling full, measure by volume to fullness [VTF] p=0.038), large fasting gastric volume (GV, p=0.03), accelerated gastric emptying (GE) $T_{1/2}$ (solids: p<0.001; liquids: p=0.011), and lower postprandial peak plasma levels of PYY (p=0.003). In addition, principal components (PC) analysis identified latent dimensions (LDs) accounting for ~81% of OW-OB variation and sub-classifies obesity in satiation (21%), gastric capacity (15%), behavioral (13%), gastric sensorimotor (11%) factors, GLP-1 levels (9%), and others (31%) (Acosta et al., 2015 *Gastroenterology* 148:537-546).

Identification of Biomarkers

An analysis of 102 patients with obesity, matched for gender, age and BMI was done. These individuals were non-diabetic and were in not medications for weight loss. Based on the profile of each patient we were able to validate the main groups in obesity in 1) low satiation, 2) rapid return to hunger, 3) behavioral eating (identified by questionnaire), 4) large fasting gastric volume, 5) mixed, and 6) low resting energy expenditure group.

Figure 2A:
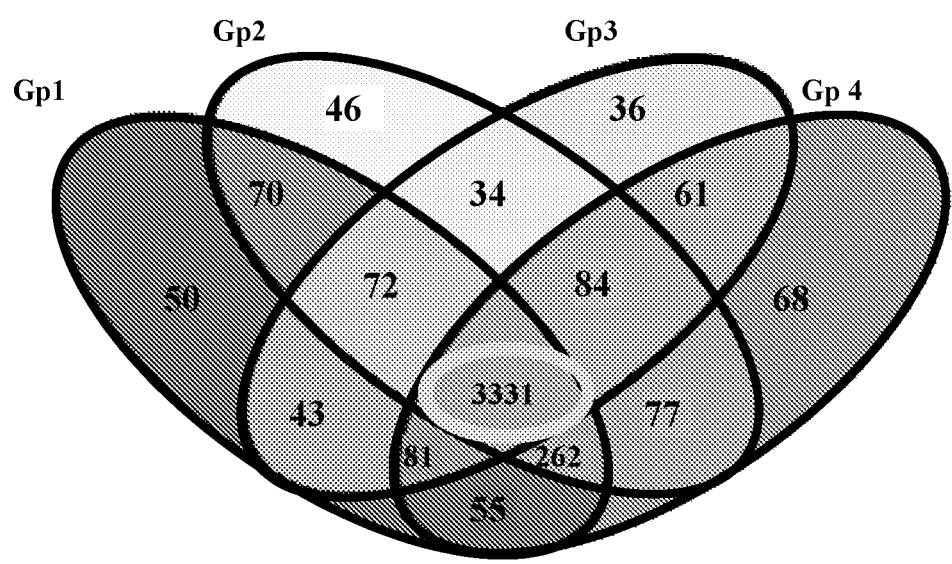
FIGS. 2A and 2B show biomarker discovery. A) Venn Diagrams of unique metabolites per obesity phenotype identified using positive-HILIC untargeted metabolomics. GP1—satiation; GP2—satiety (rapid return to hunger); Gp3—hedonic; and Gp4—energy expenditure. B) A score plot of a principal component analysis (PCA) of obesity phenotypes showing that obesity phenotype groups can be separated based on metabolic differences.
Figure 2B:
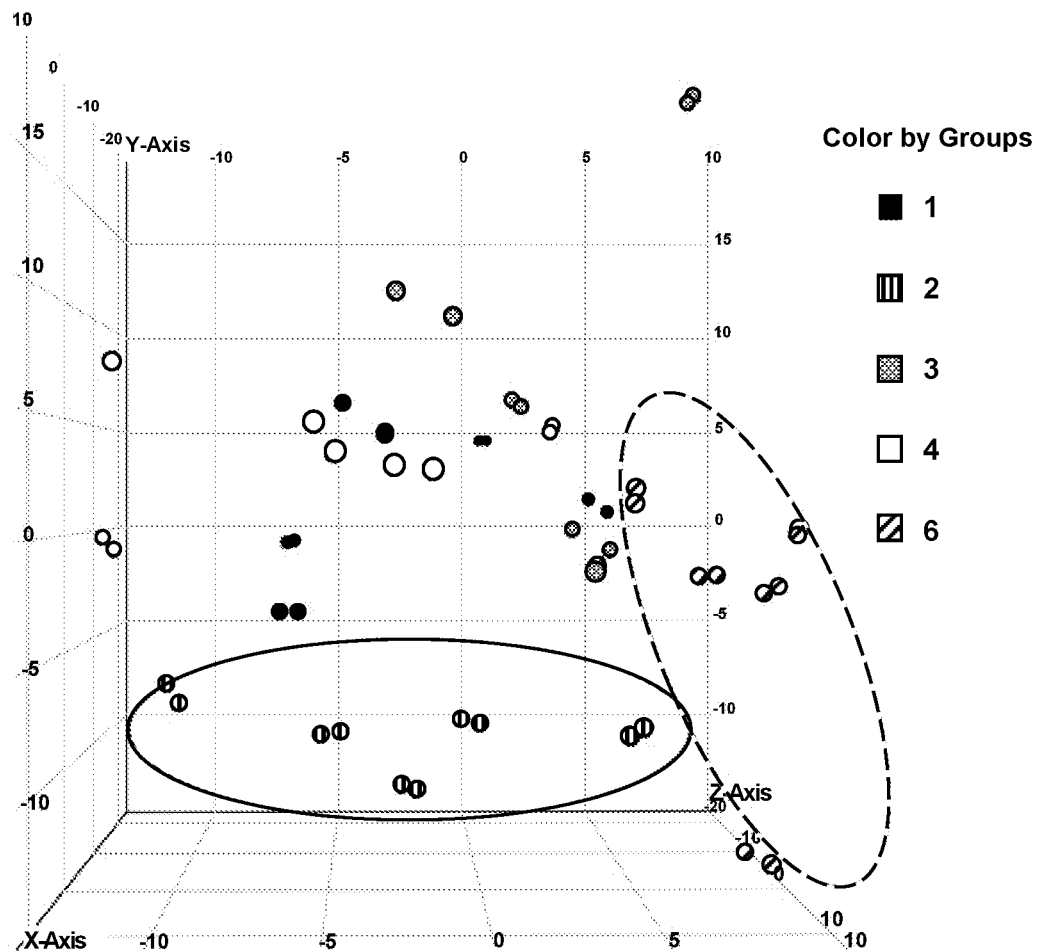

A combined logit regression model using stepwise variable selection was created to identify variables that are significantly associated with each of the phenotypic classes. Untargeted metabolomics identified unique metabolites in each group (FIG. 2A). Each of these metabolites is independent from the other groups (FIG. 2B). From these metabolites, a "VIP" (variable of importance) was identified for each group. Then, a targeted metabolomics was done with the VIP as well as neurotransmitters, amino compounds, fatty acids, and short chain fatty acids. Examples variables are as shown in Tables 2-5. For example, targeted metabolites, peptides, and SNPS analyzed are as shown in Table 2, other obesity related gene variants are as shown in in Table 3, targeted peptides are as shown in in Table 4, and targeted genes are as shown in in Table 5.

TABLE 2

Analytes Examined using SNPs, Hormones, Peptides and Targeted Metabolomics.

| Neuro transmitters | Fatty acids and Lipid | Amino Compounds | Bile acids | Peptides | SNP-containing Genes | Hormones | carbohydrates |
|---|---|---|---|---|---|---|---|
| γ-aminobutyric acid | acetic | Histidine | LCA | ghrelin | ADRA2A | cholesterol | glucose |
| Acetylcholine | propionic | Hydroxyproline | CDCA | PYY | ADRA2C | insulin | |
| Adenosine | isobutyric | 1-Methylhistidine | DCA | CCK | GNB3 | glucagon | |
| aspartate | butyric | 3-Methylhistidine | UDCA | GLP-1 | FTO | leptin | |
| Dopamine | valeric | Asparagine | HDCA | GLP-2 | MC4R | adiponectin | |
| D-serine | isovaleric | Phosphoethanolamine | CA | glucagon | TCF7L2 | | |
| Glutamate | hexanoic | Arginine | GLCA | oxyntomodulin | 5-HTTLPR | | |
| Glycine | octanoic | Carnosine | GCDCA | neurotensin | HTR2C | | |
| Histidine | myristic | Taurine | GDCA | FGF | UCP2 | | |
| Norepinephrine | palmitic | Anserine | GUDCA | GIP | UCP3 | | |
| Serotonin | palmitoleic | Serine | GHDCA | OXM | GPBAR1 | | |
| Taurine | palmitelaidic | Glutamine | GCA | FGF19 | NR1H4 | | |
| | stearic | Ethanolamine | TLCA | FGF21 | FGFR4 | | |
| | oleic | Glycine | TCDCA | LDL | PYY | | |
| | elaidic | Aspartic Acid | TDCA | insulin | GLP-1 | | |
| | linoleic | Sarcosine | TUDCA | glucagon | CCK | | |
| | a-linolenic | Proline | THDCA | amylin | Leptin | | |
| | arachidonic | alpha-Aminoadipic-acid | TCA | pancreatic polypeptide | Adiponectin | | |
| | eicosapentaenoic | beta-Aminoisobutyric-acid | DHCA | leptin | Neurotensin | | |
| | docosahexaenoic | alpha-Amino-N-butyric-acid | THCA | adiponectin | Ghrelin | | |
| | LDL | Ornithine | | | GLP-1 receptor | | |

TABLE 2-continued

Analytes Examined using SNPs, Hormones, Peptides and Targeted Metabolomics.

| Neuro transmitters | Fatty acids and Lipid | Amino Compounds | Bile acids | Peptides | SNP-containing Genes | Hormones | carbohydrates |
|---|---|---|---|---|---|---|---|
| | triglycerides | Cystathionine 1 | | | GOAT | | |
| | | Cystine | | | DPP4 | | |
| | | Lysine | | | | | |
| | | Tyrosine | | | | | |
| | | Methionine | | | | | |
| | | Valine | | | | | |
| | | Isoleucine | | | | | |
| | | Leucine | | | | | |
| | | Homocystine | | | | | |
| | | Phenylalanine | | | | | |
| | | Tryptophan | | | | | |
| | | Citrulline | | | | | |
| | | Glutamic Acid | | | | | |
| | | beta-Alanine | | | | | |
| | | Threonine | | | | | |
| | | Alanine | | | | | |
| | | Hydroxylysine 1 | | | | | |
| | | Acetone | | | | | |
| | | Acetoacetic Acid | | | | | |

TABLE 3

SNPs associated with obesity [Is this title accurate?]

| SNP | Chr. | Position (bp) | Nearest Gene |
|---|---|---|---|
| rs657452 | 1 | 49,362,434 | AGBL4 |
| rs11583200 | 1 | 50,332,407 | ELAVL4 |
| rs2820292 | 1 | 200,050,910 | NAV1 |
| rs11126666 | 2 | 26,782,315 | KCNK3 |
| rs11688816 | 2 | 62,906,552 | EHBP1 |
| rs1528435 | 2 | 181,259,207 | UBE2E3 |
| rs7599312 | 2 | 213,121,476 | ERBB4 |
| rs6804842 | 3 | 25,081,441 | RARB |
| rs2365389 | 3 | 61,211,502 | FHIT |
| rs3849570 | 3 | 81,874,802 | GBE1 |
| rs16851483 | 3 | 142,758,126 | RASA2 |
| rs17001654 | 4 | 77,348,592 | SCARB2 |
| rs11727676 | 4 | 145,878,514 | HHIP |
| rs2033529 | 6 | 40,456,631 | TDRG1 |
| rs9400239 | 6 | 109,084,356 | FOXO3 |
| rs13191362 | 6 | 162,953,340 | PARK2 |
| rs1167827 | 7 | 75,001,105 | HIP1 |
| rs2245368 | 7 | 76,446,079 | DTX2P1 |
| rs2033732 | 8 | 85,242,264 | RALYL |
| rs4740619 | 9 | 15,624,326 | C9orf93 |
| rs6477694 | 9 | 110,972,163 | EPB41L4B |
| rs1928295 | 9 | 119,418,304 | TLR4 |
| rs10733682 | 9 | 128,500,735 | LMX1B |
| rs7899106 | 10 | 87,400,884 | GRID1 |
| rs17094222 | 10 | 102,385,430 | HIF1AN |
| rs11191560 | 10 | 104,859,028 | NT5C2 |
| rs7903146 | 10 | 114,748,339 | TCF7L2 |
| rs2176598 | 11 | 43,820,854 | HSD17B12 |
| rs12286929 | 11 | 114,527,614 | CADM1 |
| rs11057405 | 12 | 121,347,850 | CLIP1 |
| rs10132280 | 14 | 24,998,019 | STXBP6 |
| rs12885454 | 14 | 28,806,589 | PRKD1 |
| rs3736485 | 15 | 49,535,902 | DMXL2 |
| rs758747 | 16 | 3,567,359 | NLRC3 |
| rs2650492 | 16 | 28,240,912 | SBK1 |
| rs9925964 | 16 | 31,037,396 | KAT8 |
| rs1000940 | 17 | 5,223,976 | RABEP1 |
| rs1808579 | 18 | 19,358,886 | C18orf8 |
| rs7243357 | 18 | 55,034,299 | GRP |
| rs17724992 | 19 | 18,315,825 | PGPEP1 |
| rs977747 | 1 | 47,457,264 | TAL1 |
| rs1460676 | 2 | 164,275,935 | FIGN |
| rs17203016 | 2 | 207,963,763 | CREB1 |
| rs13201877 | 6 | 137,717,234 | IFNGR1 |
| rs1441264 | 13 | 78,478,920 | MIR548A2 |
| rs7164727 | 15 | 70,881,044 | LOC100287559 |
| rs2080454 | 16 | 47,620,091 | CBLN1 |
| rs9914578 | 17 | 1,951,886 | SMG6 |
| rs2836754 | 21 | 39,213,610 | ETS2 |
| rs492400 | 2 | 219,057,996 | USP37 |
| rs16907751 | 8 | 81,538,012 | ZBTB10 |
| rs9374842 | 6 | 120,227,364 | LOC285762 |
| rs9641123 | 7 | 93,035,668 | CALCR |
| rs9540493 | 13 | 65,103,705 | MIR548X2 |
| rs4787491 | 16 | 29,922,838 | INO80E |
| rs6465468 | 7 | 95,007,450 | ASB4 |
| rs7239883 | 18 | 38,401,669 | LOC284260 |
| rs3101336 | 1 | 72,523,773 | NEGR1 |
| rs12566985 | 1 | 74,774,781 | FPGT |
| rs12401738 | 1 | 78,219,349 | FUBP1 |
| rs11165643 | 1 | 96,696,685 | PTBP2 |
| rs17024393 | 1 | 109,956,211 | GNAT2 |
| rs543874 | 1 | 176,156,103 | SEC16B |
| rs13021737 | 2 | 622,348 | TMEM18 |
| rs10182181 | 2 | 25,003,800 | ADCY3 |
| rs1016287 | 2 | 59,159,129 | LINC01122 |
| rs2121279 | 2 | 142,759,755 | LRP1B |
| rs13078960 | 3 | 85,890,280 | CADM2 |
| rs1516725 | 3 | 187,306,698 | ETV5 |
| rs10938397 | 4 | 44,877,284 | GNPDA2 |
| rs13107325 | 4 | 103,407,732 | SLC39A8 |
| rs2112347 | 5 | 75,050,998 | POC5 |
| rs205262 | 6 | 34,671,142 | C6orf106 |
| rs2207139 | 6 | 50,953,449 | TFAP2B |
| rs17405819 | 8 | 76,969,139 | HNF4G |
| rs10968576 | 9 | 28,404,339 | LINGO2 |
| rs4256980 | 11 | 8,630,515 | TRIM66 |
| rs11030104 | 11 | 27,641,093 | BDNF |
| rs3817334 | 11 | 47,607,569 | MTCH2 |
| rs7138803 | 12 | 48,533,735 | BCDIN3D |
| rs12016871 | 13 | 26,915,782 | MTIF3 |
| rs12429545 | 13 | 53,000,207 | OLFM4 |
| rs11847697 | 14 | 29,584,863 | PRKD1 |
| rs7141420 | 14 | 78,969,207 | NRXN3 |
| rs16951275 | 15 | 65,864,222 | MAP2K5 |
| rs12446632 | 16 | 19,842,890 | GPRC5B |
| rs3888190 | 16 | 28,796,987 | ATP2A1 |
| rs1558902 | 16 | 52,361,075 | FTO |
| rs12940622 | 17 | 76,230,166 | RPTOR |
| rs6567160 | 18 | 55,980,115 | MC4R |

TABLE 3-continued

SNPs associated with obesity [Is this title accurate?]

| SNP | Chr. | Position (bp) | Gene |
|---|---|---|---|
| rs29941 | 19 | 39,001,372 | KCTD15 |
| rs2075650 | 19 | 50,087,459 | TOMM40 |
| rs2287019 | 19 | 50,894,012 | QPCTL |
| rs3810291 | 19 | 52,260,843 | ZC3H4 |
| rs7715256 | 5 | 153,518,086 | GALNT10 |
| rs2176040 | 2 | 226,801,046 | LOC646736 |
| rs6091540 | 20 | 50,521,269 | ZFP64 |

| SNP | Chr. | Position (bp) | Genes |
|---|---|---|---|
| rs1800544 | | | ADRA2A |
| Ins-Del-322 | | | ADRA2C |
| rs5443 | | | GNB3 |
| rs1129649 | | | GNB3 |
| rs1047776 | | | GNB3 |
| rs9939609 | | | FTO |
| rs17782313 | | | MC4R |
| rs7903146 | | | TCF7L2 |
| rs4795541 | | | 5-HTTLPR |
| rs3813929 | | | HTR2C |
| rs518147 | | | HTR2C |
| rs1414334 | | | HTR2C |
| rs659366 | | | UCP2 |
| −3474, | | | UCP2 |
| rs2075577 | | | UCP3 |
| rs15763 | | | UCP3 |
| rs1626521 | | | UCP3 |
| rs11554825 | | | GPBAR1 |
| rs4764980 | | | NR1H4 |
| rs434434 | | | FGFR4 |
| rs351855 | | | FGFR4 |

| RSID | Gene_Symbol |
|---|---|
| exm2261885 | . |
| exm2264702 | . |
| kgp10003923 | . |
| kgp10360658 | . |
| kgp10374580 | . |
| kgp1093561 | . |
| kgp11089754 | . |
| kgp11154375 | . |
| kgp11564777 | . |
| kgp11808957 | . |
| kgp11836456 | . |
| kgp11902597 | . |

| SNP | Chr. | Position (bp) | Nearest Genes |
|---|---|---|---|
| kgp12031075 | | | . |
| kgp12088423 | | | . |
| kgp1283935 | | | . |
| kgp1287405 | | | . |
| kgp129784 | | | . |
| kgp1371036 | | | . |
| kgp1419661 | | | . |
| kgp1612367 | | | . |
| kgp16387096 | | | . |
| kgp16914214 | | | . |
| kgp2241756 | | | . |
| kgp2251945 | | | . |
| kgp238191 | | | . |
| kgp2727759 | | | . |
| kgp2735253 | | | . |
| kgp2925720 | | | . |
| kgp3186084 | | | . |
| kgp3371090 | | | . |
| kgp3712407 | | | . |
| kgp3846165 | | | . |
| kgp3847753 | | | . |
| kgp429141 | | | . |
| kgp4433253 | | | . |
| kgp447667 | | | . |
| kgp4725781 | | | . |
| kgp5201059 | | | . |
| kgp5201171 | | | . |
| kgp5269120 | | | . |
| kgp5471252 | | | . |
| kgp5829795 | | | . |
| kgp599811 | | | . |
| kgp6037240 | | | . |
| kgp6508014 | | | . |
| kgp6615769 | | | . |
| kgp6816777 | | | . |
| kgp7069937 | | | . |
| kgp7157564 | | | . |
| kgp7328604 | | | . |
| kgp7496475 | | | . |
| kgp7707096 | | | . |
| kgp7798504 | | | . |
| kgp8018963 | | | . |
| kgp8206543 | | | . |
| kgp8818851 | | | . |
| kgp8860587 | | | . |
| kgp9190754 | | | . |
| kgp9456377 | | | . |
| kgp9526272 | | | . |
| kgp9629679 | | | . |
| rs10489944 | | | . |
| rs10504589 | | | . |
| rs10808295 | | | . |
| rs11060968 | | | . |
| rs11225943 | | | . |
| rs11720464 | | | . |
| rs12354667 | | | . |
| rs12427263 | | | . |
| rs13130205 | | | . |
| rs1372851 | | | . |
| rs1493716 | | | . |
| rs1541616 | | | . |
| rs1674070 | | | . |
| rs1873367 | | | . |
| rs1889757 | | | . |
| rs2470000 | | | . |
| rs2470029 | | | . |
| rs2647979 | | | . |
| rs2720400 | | | . |
| rs2851820 | | | . |
| rs2851836 | | | . |
| rs288756 | | | . |
| rs348337 | | | . |
| rs4707490 | | | . |
| rs6005420 | | | . |
| rs6008618 | | | . |
| rs6472339 | | | . |
| rs6776731 | | | . |
| rs6828992 | | | . |
| rs6888630 | | | . |
| rs6957234 | | | . |
| rs7082638 | | | . |
| rs7297442 | | | . |
| rs7658020 | | | . |
| rs7803317 | | | . |
| rs8141901 | | | . |
| rs849309 | | | . |
| rs9511655 | | | . |
| rs9810198 | | | . |
| rs9860734 | | | . |
| exm2264762 | | | . |
| exm2271737 | | | . |
| exm2272553 | | | . |
| kgp10285805 | | | . |
| kgp10360658 | | | . |
| kgp10548537 | | | . |
| kgp10901790 | | | . |
| kgp11044637 | | | . |
| kgp11343144 | | | . |
| kgp11430653 | | | . |
| kgp11530429 | | | . |
| kgp11836456 | | | . |
| kgp11960081 | | | . |
| kgp11974172 | | | . |
| kgp12031075 | | | . |
| kgp12088423 | | | . |
| kgp12289889 | | | . |
| kgp127695 | | | . |

TABLE 3-continued

SNPs associated with obesity [Is this title accurate?]

| SNP | Gene |
|---|---|
| kgp1278486 | . |
| kgp1586406 | . |
| kgp16387096 | . |
| kgp1727603 | . |
| kgp1887803 | . |
| kgp1939387 | . |
| kgp2241672 | . |
| kgp22776953 | . |
| kgp227938 | . |
| kgp2369570 | . |
| kgp3371090 | . |
| kgp3406296 | . |
| kgp3660486 | . |
| kgp3662728 | . |
| kgp3712407 | . |
| kgp374568 | . |
| kgp3846165 | . |
| kgp4074864 | . |
| kgp429141 | . |
| kgp447667 | . |
| kgp4534617 | . |
| kgp4799975 | . |
| kgp4944907 | . |
| kgp5201171 | . |
| kgp5329941 | . |
| kgp5471252 | . |
| kgp563498 | . |
| kgp5671927 | . |
| kgp5780899 | . |
| kgp5829795 | . |
| kgp6037240 | . |
| kgp6688816 | . |
| kgp6827318 | . |
| kgp7048855 | . |
| kgp7069937 | . |
| kgp7235499 | . |
| kgp7945681 | . |
| kgp8628976 | . |
| kgp8860587 | . |
| kgp9190754 | . |
| kgp9231149 | . |
| kgp9578092 | . |
| kgp965777 | . |
| rs10150519 | . |
| rs10161070 | . |
| rs10451103 | . |
| rs10742039 | . |
| rs10877143 | . |
| rs11720464 | . |
| rs12506204 | . |
| rs12593784 | . |
| rs12937299 | . |
| rs13338004 | . |
| rs1372851 | . |
| rs1493716 | . |
| rs1512840 | . |
| rs1541616 | . |
| rs16822391 | . |
| rs17076260 | . |
| rs17453871 | . |
| rs1873367 | . |
| rs201607 | . |
| rs202558 | . |
| rs2169564 | . |
| rs2647979 | . |
| rs2720400 | . |
| rs2761413 | . |
| rs2957787 | . |
| rs3762535 | . |
| rs4313958 | . |
| rs4461665 | . |
| rs4543516 | . |
| rs4707490 | . |
| rs4964150 | . |
| rs6008618 | . |
| rs6448182 | . |
| rs6585563 | . |
| rs6828992 | . |
| rs6957234 | . |
| rs7297442 | . |
| rs7658020 | . |
| rs768969 | . |
| rs7846145 | . |
| rs7981554 | . |
| rs8002390 | . |
| rs8141901 | . |
| rs935201 | . |
| rs9378848 | . |
| rs9810198 | . |
| rs9860734 | . |
| rs9864846 | . |
| kgp2297621 | ACSL6 |
| rs440970 | ACSL6 |
| kgp10461170 | ADARB2 |
| kgp7332119 | ADARB2 |
| rs12415114 | ADARB2 |
| kgp9064589 | ADCY8 |
| rs13133908 | ADH1B |
| kgp12414761 | ADH1B |
| rs13133908 | ADH1B |
| rs2075633 | ADH1B |
| rs7518469 | AJAP1 |
| rs429790 | ATP2C2 |
| kgp3288649 | ATP6V0D2 |
| rs2832231 | C21orf7 |
| kgp10136381 | CAMKMT |
| kgp3161157 | CAMKMT |
| kgp3203202 | CAMKMT |
| kgp3968222 | CAMKMT |
| kgp4140267 | CAMKMT |
| rs13406580 | CAMKMT |
| rs1551882 | CAMKMT |
| rs17032193 | CAMKMT |
| rs7593926 | CAMKMT |
| kgp4005992 | CAP2 |
| kgp7298922 | CASC4 |
| kgp1789974 | CD48 |
| kgp5511006 | CD48 |
| kgp1789974 | CD48 |
| kgp5511006 | CD48 |
| kgp7256435 | CDC42SE2 |
| rs4706020 | CDC42SE2 |
| rs3812178 | CDYL |
| rs3812179 | CDYL |
| kgp3731792 | CES5AP1 |
| kgp6395031 | CLMN |
| kgp6395031 | CLMN |
| kgp4873414 | CNPY4 |
| rs3806043 | COL19A1 |
| kgp3071123 | COL27A1 |
| kgp6064462 | COL27A1 |
| kgp6796371 | COL27A1 |
| rs1249745 | COL27A1 |
| kgp5314602 | COL4A3 |
| kgp11506369 | CORO1C |
| kgp6473219 | CORO1C |
| kgp10992142 | CPZ |
| rs8087866 | CTIF |
| kgp7710562 | DAAM2 |
| exm430196 | DCHS2 |
| exm430197 | DCHS2 |
| kgp49288 | DCHS2 |
| kgp766527 | DCHS2 |
| rs4696584 | DCHS2 |
| kgp3890072 | DOCK8 |
| rs1980876 | DOCK8 |
| exm451231 | EGFLAM |
| rs6897179 | EGFLAM |
| kgp10622968 | FAM125B |
| kgp5732367 | FAM71E2 |
| kgp10294313 | FRMD3 |
| kgp2344514 | FRMD3 |
| kgp7900743 | FRMD3 |
| kgp3392580 | GALNTL4 |
| kgp4456104 | GLT1D1 |
| kgp5287249 | HHAT |

TABLE 3-continued

SNPs associated with obesity [Is this title accurate?]

| | |
|---|---|
| exm1319778 | KRT23 |
| rs8037 | KRT23 |
| rs9257 | KRT23 |
| kgp10012744 | LHPP |
| kgp1057196 | LINC00578 |
| kgp8853148 | LINC00578 |
| rs6799682 | LINC00578 |
| rs7632844 | LINC00578 |
| kgp11567842 | LINC00620 |
| rs12495328 | LINC00620 |
| kgp4159029 | LIPC |
| kgp1640513 | LOC100128714 |
| kgp4598936 | LOC100128714 |
| kgp5262759 | LOC100128714 |
| rs11635697 | LOC100128714 |
| rs12593847 | LOC100128714 |
| rs8023270 | LOC100128714 |
| kgp1743339 | LOC100287160 |
| kgp7667092 | LOC100289473 |
| rs6135960 | LOC100289473 |
| rs6135960 | LOC100289473 |
| kgp5351206 | LOC100293612\|LINC00620 |
| kgp10995216 | LOC100506869 |
| kgp22804264 | LOC100506869 |
| rs4760137 | LOC100506869 |
| rs1566141 | LOC100507053 |
| kgp10134243 | LOC100507053 |
| rs10008281 | LOC100507053 |
| rs1229966 | LOC100507053 |
| rs1566141 | LOC100507053 |
| rs2051428 | LOC100507053 |
| rs3819197 | LOC100507053\|ADH1A |
| rs3819197 | LOC100507053\|ADH1A |
| rs9995799 | LOC100507053\|ADH6 |
| kgp1289034 | LOC100507443 |
| rs9981988 | LOC100996571\|CYYR1 |
| kgp258053 | LOC152225 |
| kgp6272649 | LOC152225 |
| kgp2759189 | LOC255130 |
| kgp2759189 | LOC255130 |
| rs10980642 | LPAR1 |
| kgp5423754 | LUZP2 |
| kgp8988372 | LUZP2 |
| kgp9462081 | MCM7 |
| rs2261360 | MCM7 |
| kgp8065051 | MICAL3 |
| kgp4439669 | MMS19 |
| kgp18459 | MYBPC1 |
| kgp1800707 | NR2F2-AS1 |
| rs7831515 | NSMCE2 |
| rs16958048 | NTN1 |
| kgp7166603 | OAZ2 |
| kgp7077044 | O3FAR1 |
| kgp2414524 | OSBP2 |
| kgp2580452 | OSBP2 |
| kgp7020841 | OSBP2 |
| rs4820897 | OSBP2 |
| kgp7020841 | OSBP2 |
| kgp7082195 | P4HA2 |
| rs6667138 | PADI1 |
| rs6667138 | PADI1 |
| kgp7908292 | PARD3B |
| rs7558785 | PARD3B |
| kgp11077304 | PARK2 |
| exm-rs2795918 | PCDH15 |
| kgp1058322 | PCDH15 |
| kgp11029138 | PCDH15 |
| kgp11410092 | PCDH15 |
| kgp2961930 | PCDH15 |
| kgp5544438 | PCDH15 |
| kgp9631691 | PCDH15 |
| rs4082042 | PCDH15 |
| kgp9916431 | PKIB |
| rs13218313 | PKIB |
| kgp4769029 | PRH1-PRR4 |
| kgp9716281 | PTPRD |
| rs7045790 | RALGPS1\|ANGPTL2 |
| rs17081778 | RPS24P10 |
| kgp10074267 | RTN4RL1 |
| kgp11049623 | RYR2 |
| kgp8225782 | SCN2A |
| rs2075703 | SCN2A |
| rs6744911 | SCN2A |
| rs12706974 | SEMA3C |
| rs1358340 | SEMA3C |
| kgp7788385 | SEMA5A |
| rs3822799 | SEMA5A |
| kgp3608544 | SFMBT2 |
| rs1887757 | SGCG |
| rs9580573 | SGCG |
| kgp390881 | SLC22A15 |
| kgp2776219 | SLC2A2 |
| exm988933 | SLCO1B1 |
| rs2306283 | SLCO1B1 |
| rs4149040 | SLCO1B1 |
| exm988933 | SLCO1B1 |
| rs2306283 | SLCO1B1 |
| rs4149040 | SLCO1B1 |
| kgp8338369 | SMOC2 |
| kgp12080543 | SNCAIP |
| kgp4607090 | SNCAIP |
| rs4895350 | SNCAIP |
| kgp1043980 | SNX18 |
| kgp2071353 | SRRM4 |
| kgp7567091 | SUSD1 |
| kgp7567091 | SUSD1 |
| kgp12526521 | TBC1D16 |
| kgp5557307 | TCERG1L |
| rs13340295 | TENM3 |
| kgp3414710 | TJP3 |
| kgp10345778 | TLL1 |
| rs4690833 | TLL1 |
| rs2568085 | TMEM9B |
| rs1071646 | TPM1 |
| rs6738 | TPM1 |
| rs1071646 | TPM1 |
| rs6738 | TPM1 |
| rs1408817 | VTI1A |
| rs216905 | VWF |
| kgp2039705 | WWOX |
| rs6804325 | WWTR1 |
| exm382632 | ZFYVE28 |
| rs12532238 | ZNF3 |
| rs6592 | ZNF3 |
| kgp6175568 | ZNF609 |
| rs11558476 | ZSCAN21 |

TABLE 4

Gastrointestinal peptides associated with obesity.

| Hormone | Source | Normal function |
|---|---|---|
| Cholecystokinin (CCK) | Duodenum | Increase satiation |
| Ghrelin | Gastric fundus | Stimulate appetite |
| Glucagon-like peptide 1 (GLP-1) | Distal small intestine and colon | Increase satiety |
| Peptide YY (PYY) | Distal small intestine and colon | Increase satiety |

* Low calorie diet can alter peptide concentrations.

TABLE 5

Genes associated with obesity.

| Primary Endpoints | Quantitative Trait | Genotype potentially affecting organ or mechanisms associated with trait |
|---|---|---|
| Satiety | Postprandial GLP-1 and PYY | TCF7L2, GNB3, MC4R |
| Satiation | VTF, MTV (kcal) | MC4R, GNB3, HTR2C, UCP3 |
| Gastric Emptying | GE (solids) | TCF7L2, ADRA2A, UCP3 |
| Appetite | Fasting Ghrelin | MC4R, FTO, GNB3 |

* Gene variants were selected based on association with BMI and mechanism of action.

Table 6 summarizes the variables that were significantly associated with each of the phenotypic groups vs the rest of the groups.

TABLE 6

SNPs present in each obesity group

| Obesity Phenotype Group | Gene | Exemplary SNP |
|---|---|---|
| 1: low satiation | HTR2C, POMC, NPY, AGRP, MC4R, GNB3, SERT, BDNF | rs1414334 |
| 2: low satiety | PYY, GLP-1, MC4R, GPBAR1, TCF7L2, ADRA2A, PCSK, TMEM18 | rs7903146 |
| 3: behavioral eating | SLC6A4/SERT, DRD2 | rs4795541 |
| 4: large fasting gastric volume | TCF7L2, UCP3, ADRA2A, | rs1626521 |
| 5: mixed | | |
| 6: low resting energy expenditure | FTO, LEP, LEPR, UCP1, UCP2, UCP3, ADRA2, KLF14, NPC1, LYPLAL1, ADRB2, ADRB3, BBS1 | rs2075577 |

Combinations of compounds (amino-compounds, neurotransmitters fatty acids, metabolic peptides, and metabolic gene) were identified as significantly associated with each of the obesity phenotypic groups. The variables that were significantly associated with each of the phenotypic groups included the following:

Questionnaire results:
hospital anxiety and depression scale-anxiety subscale (HADS-A),
Metabolites:
1-methylhistine
seratonin
glutamine
gamma-amino-n-butyric-acid
isocaproic
allo-isoleucine
hydroxyproline
beta-aminoisobutyric-acid
alanine
hexanoic
tyrosine
phenylalanine
Gastrointestinal Peptides:
fasting ghrelin
fasting PYY Algorithm
The following formulas were used to identify the obesity phenotype of a patient based upon the signature of the 14 compounds identified as being significantly associated with each of the obesity phenotypic groups. The formulas predicted the phenotypes with a $r2$ of 0.90 and a probability Chi-square of less than 0.0001.

Lin[1]
(−1552.38148595936)
+40.797700201235 *:Name("HADS-A")
+1.32549623006262 *:Glutamine
+−0.111622239757052 *:Alanine
+−616.954862561479 *:Name("gamma-Amino-N-butyric-acid")
+−89.402967640225 *:Name("beta-Aminoisobutyric-acid")
+−1.73891527871898 *:Tyrosine
+6.24138513457712 *:Phenylalanine
+2148.66822848398 *:isocaproic
+−20.6187102527618 *:hexanoic
+56.3110714341266 *:Name("Log(Hydroxyproline)")
+82.3818646650792 *:Name("Log(1-Methylhistine)")
+−26.8826686365131 *:Name("Log(seratonin)")
+0.245926705626903 *:Name("PYY_-15")
+1.89180999803712 *:Name("Ghrelin_-15")
+75.8755521857061 *:Name("allo-Isoleucine")

Lin [2]
(−2031.26556804871)
+56.9736558824775 *:Name("HADS-A")
+−0.0118072070103887 *:Glutamine
+−0.0995668418558728 *:Alanine
+1609.83650774629 *:Name("gamma-Amino-N-butyric-acid")
+123.106026249695 *:Name("beta-Aminoisobutyric-acid")
+13.0377088181536 *:Tyrosine
+−2.42979784589652 *:Phenylalanine
+3057.74326808551 *:isocaproic
+63.6119366218627 *:hexanoic
+99.2853520251878 *:Name("Log(Hydroxyproline)")
+0.166314503531418 *:Name("Log(1-Methylhistine)")
+6.21451740476229 *:Name("Log(seratonin)")
+−0.696742681406157 *:Name("PYY_-15")
+2.30188885859994 *:Name("Ghrelin_-15")
+220.083419205279 *:Name("allo-Isoleucine")

Lin [3]
(−735.067323742327)
+84.6709055694921 *:Name("HADS-A")
+0.739638607406857 *:Glutamine
+0.0161670919675227 *:Alanine
+1.70702352345921 *:Name("gamma-Amino-N-butyric-acid")
+4.08385430756663 *:Name("beta-Aminoisobutyric-acid")
+4.83658065569896 *:Tyrosine
+−7.4973831454893 *:Phenylalanine
+1467.49860590747 *:isocaproic
+51.4109043756237 *:hexanoic
+−56.3364437814115 *:Name("Log(Hydroxyproline)")
+45.3693267895892 *:Name("Log(1-Methylhistine)")
+24.1167481430051 *:Name("Log(seratonin)")
+−1.56458536889981 *:Name("PYY_-15")
+2.15880622406247 *:Name("Ghrelin_-15")
+72.4632042822316 *:Name("allo-Isoleucine")

Lin[4]
(−38.8679541168302)
+1.54112014174663 *:Name("HADS-A")
+0.00119976598048842 *:Glutamine
+0.056518755537321 *:Alanine +34.9734228686154 *:Name("gamma-Amino-N-butyric-acid")
+2.64367056830481 *:Name("beta-Aminoisobutyric-acid")
+0.0996495148185086 *:Tyrosine
+−0.14869421223421 *:Phenylalanine
+8.69300091428836 *:isocaproic
+1.77363291550863 *:hexanoic
+−1.58953123143685 *:Name("Log(Hydroxyproline)")
+0.127307799711255 *:Name("Log(1-Methylhistine)")
+−3.33170879355105 *:Name("Log(seratonin)")
+0.0387731073018872 *:Name("PYY_-15")
+0.0662851699121999 *:Name("Ghrelin_-15")
+−1.4086102207227 *:Name("allo-Isoleucine")

$1/(1+\text{Exp}(-(\text{``Lin[1]''}))+\text{Exp}((\text{``Lin[2]''})-(\text{``Lin[1]''}))+\text{Exp}((\text{``Lin[3]''})-(\text{``Lin[1]''}))+\text{Exp}((\text{``Lin[4]''})-(\text{``Lin[1]''})))$ Prob[1]

$1/(1+\text{Exp}((\text{``Lin[1]''})-(\text{``Lin[2]''}))+\text{Exp}(-(\text{``Lin[2]''}))+\text{Exp}((\text{``Lin[3]''})-(\text{``Lin[2]''}))+\text{Exp}((\text{``Lin[4]''})-(\text{``Lin[2]''})))$ Prob[2]

$1/(1+\text{Exp}((\text{``Lin[1]''})-(\text{``Lin[3]''}))+\text{Exp}((\text{``Lin[2]''})-(\text{``Lin[3]''}))+\text{Exp}(-(\text{``Lin[3]''}))+\text{Exp}((\text{``Lin[4]''})-(\text{``Lin[3]''})))$ Prob[3]

$1/(1+\text{Exp}((\text{``Lin[1]''})-(\text{``Lin[4]''}))+\text{Exp}((\text{``Lin[2]''})-(\text{``Lin[4]''}))+\text{Exp}((\text{``Lin[3]''})-(\text{``Lin[4]''}))+\text{Exp}(-(\text{``Lin[4]''})))$ Prob[4]

$1/(1+\text{Exp}((\text{``Lin[1]''}))+\text{Exp}((\text{``Lin[2]''}))+\text{Exp}((\text{``Lin[3]''}))+\text{Exp}((\text{``Lin[4]''})))$ Prob[6]

Table 7 summarizes variables (14 analytes and a questionnaire) that were significantly associated with each of the phenotypic groups with the ROC of the group vs the rest of the groups.

TABLE 7

Compounds present in each obesity group

| Source | Group 1 | Group 2 | Group 3 | Group 4 | Group 5 | Group 6 |
|---|---|---|---|---|---|---|
| 1-Methylhistine | | + | | + | | + |
| seratonin | + | | + | | + | + |
| Glutamine | + | | | + | | + |
| gamma-Amino-N-butyric-acid | | | | + | | + |
| isocaproic | + | | | + | | + |
| allo-Isoleucine | + | + | | + | | |
| Hydroxyproline | + | + | | | | |
| beta-Amino-isobutyric-acid | + | + | | + | | |
| Alanine | + | + | | + | + | + |
| hexanoic | + | | | + | + | |
| Tyrosine | + | | | + | | + |
| Phenylalanine | | + | | + | + | |
| Ghrelin | | | | | | + |
| PYY | + | | | + | | + |
| HADS-A | | | + | + | + | + |
| p value of whole model test | 0.006 | <0.001 | <0.001 | <0.001 | 0.01 | <0.001 |
| ROC value (group vs rest) | 0.90 | 0.86 | 0.91 | 0.89 | 0.86 | 0.96 |

One multinomial logistic model contained 14 compounds and one questionnaire, and the obesity phenotypes were predicted with more than 97% sensitivity and specificity (group 1=1, group 2=1, group 3=1, group 4=0.97 and group 6=0.96). When a mixed group is added to the equation, the obesity phenotypes can be predicted with more than 91% sensitivity and specificity (group 1=0.95, group 2=0.92, group 3=1, group 4=0.96, group 5=0.96 and group 6=0.97).

When group 4 and mixed are removed from the equation, the obesity phenotypes can be predicted with 100% sensitivity and specificity.

Another multinomial logistic model contained 1 behavioral assessment, 3 germline variants, and 6 fasting targeted metabolomics. The variables can be as shown in Table 8 plus questionnaire(s) (e.g., HADS and/or TEFQ21).

TABLE 8

Variables (9 analytes and a questionnaire) that were significantly associated with each of the phenotypic groups with the ROC of the group vs the rest of the groups.

| SNP | Gene | Name | Panel | Peptide |
|---|---|---|---|---|
| rs9939609.n | FTO | cystathionine1 | amino compound | fasting pyy |
| rs1626521.n | UCP3 | glycine | amino compound | fasting ghrelin |
| rs3813929.n | 5-HT2CR | valine | amino compound | |
| rs5443.n | GNB3 | serotonin | neurotransmitter | |
| rs1800544.n | ADRA2a | glutamic acid | amino compound | |
| rs2234888.n | ADRA2c | tryptophan | amino compound | |
| rs17782313 | MC4R | histidine | amino compound | |
| | | methylhistidine1 | amino compound | |
| | | methionine | amino compound | |
| | | isocaproic | amino compound | |
| | | hydroxylysine2 | amino compound | |
| | | ethanolamine | amino compound | |
| | | hydroxyproline | amino compound | |
| | | gamma-amino-n-butyric acid | neurotransmitter | |
| | | threonine | amino compound | |
| | | alpha-aminoadipic acid | amino compound | |
| | | sarcosine | amino compound | |
| | | arginine | amino compound | |
| | | histidine | neurotransmitter | |
| | | proline | amino compound | |

Obesity Phenotypes Biomarker

Figure 3:
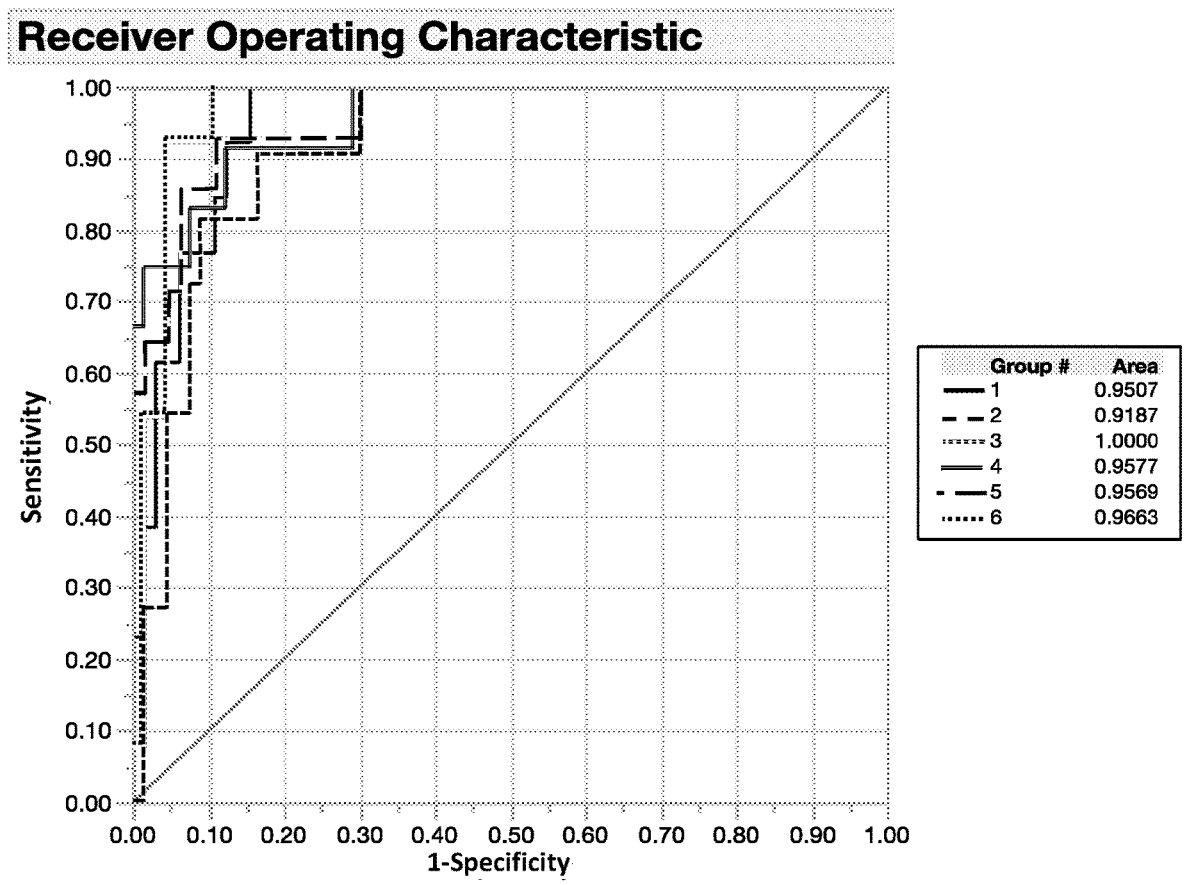
FIG. 3 is a receiver operating characteristic (ROC) curve showing the sensitivity and specificity of determining an obesity phenotype based on metabolic signature.
Figure 5:
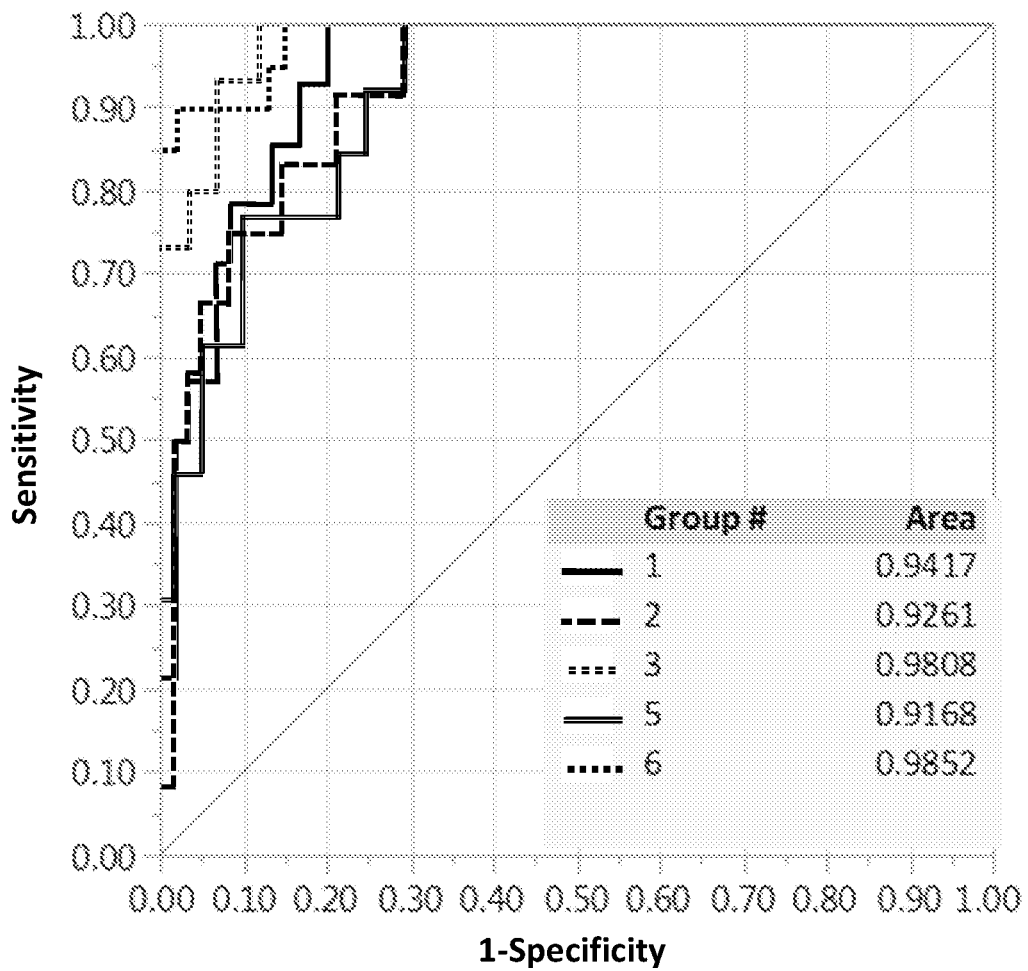
FIG. 5 is a ROC curve showing the sensitivity and specificity of determining an obesity phenotype based on metabolic signature.

Simple-blood test biomarkers were identified that can classify obese patients into their related phenotypes. To achieve this, 25 individuals with unique obesity phenotypes were selected from the cohort of 180 participants and an untargeted metabolomics study was performed using their fasting blood samples. Thus, average of 3331 unique metabolites that are associated with each obesity-related phenotype were observed and this is illustrated through the VennDiagrams of Unique Metabolites per group using Positive-HILIC Untargeted Metabolomics (FIG. 2A). These data supported the application of a targeted metabolomics approach, hypothesis-driven, to identify and quantify associated metabolites. A two-stage design was used to develop the composition of the blood test; the training and validation cohorts consisted of 102 and 78 obese patients, respectively. Based on the profile of each patient, we were able to validate the main groups in obesity cohorts, that is 1) abnormal satiation, 2) rapid return to hunger, 3) behavioral eating; 4) abnormal energy expenditure; 5) a "mixed" group. Using a multinomial logistic regression was used to develop a classification model using elastic net shrinkage for variable selection. Discrimination was evaluated using concordance index (c-index). Receiving operating characteristic curves (ROC) for the models were constructed and area under the curve (AUC) estimated. The variables were applied to a prediction model or algorithm diagnostic (patent submitted) to identify the phenotypes. The model predicted the phenotypes with an ROC of 0.91 (AUC) for the training cohort and 0.71 for the validation cohort (FIG. 3 and FIG. 5). The accuracy of the model was 86% in the whole cohort. When the model was applied to the two previously completed placebo-controlled, randomized trials, the weight loss after 2 weeks of phentermine-topiramate ER was 58% higher in the predicted group (n=3, 2.4±0.4 kg) compared to the other groups (n=9, 1.4±0.2 kg), and after 4 weeks of exenatide, weight loss was 65% higher in the predicted group (n=6, 1.5±0.6 kg) compared to the other groups (n=4, 0.9±0.7 kg).

In summary, using this actionable classification decreases obesity heterogeneity, and facilitate our understanding of human obesity. Furthermore, we have developed and validated a novel, first-of-its-kind, simple, fasting, blood-based biomarker for obesity phenotypes.

Sensitivity and Specificity of Biomarkers

To confirm the sensitivity and specificity of the biomarkers significantly associated with each of the obesity phenotypic groups, a receiver operating characteristic (ROC) analysis was done.

FIG. 3 shows the sub-classification prediction accuracy of this combined model and an ROC analysis showed that this model has >0.90 area under the curve (AUC) for all six classes.

Figure 4:
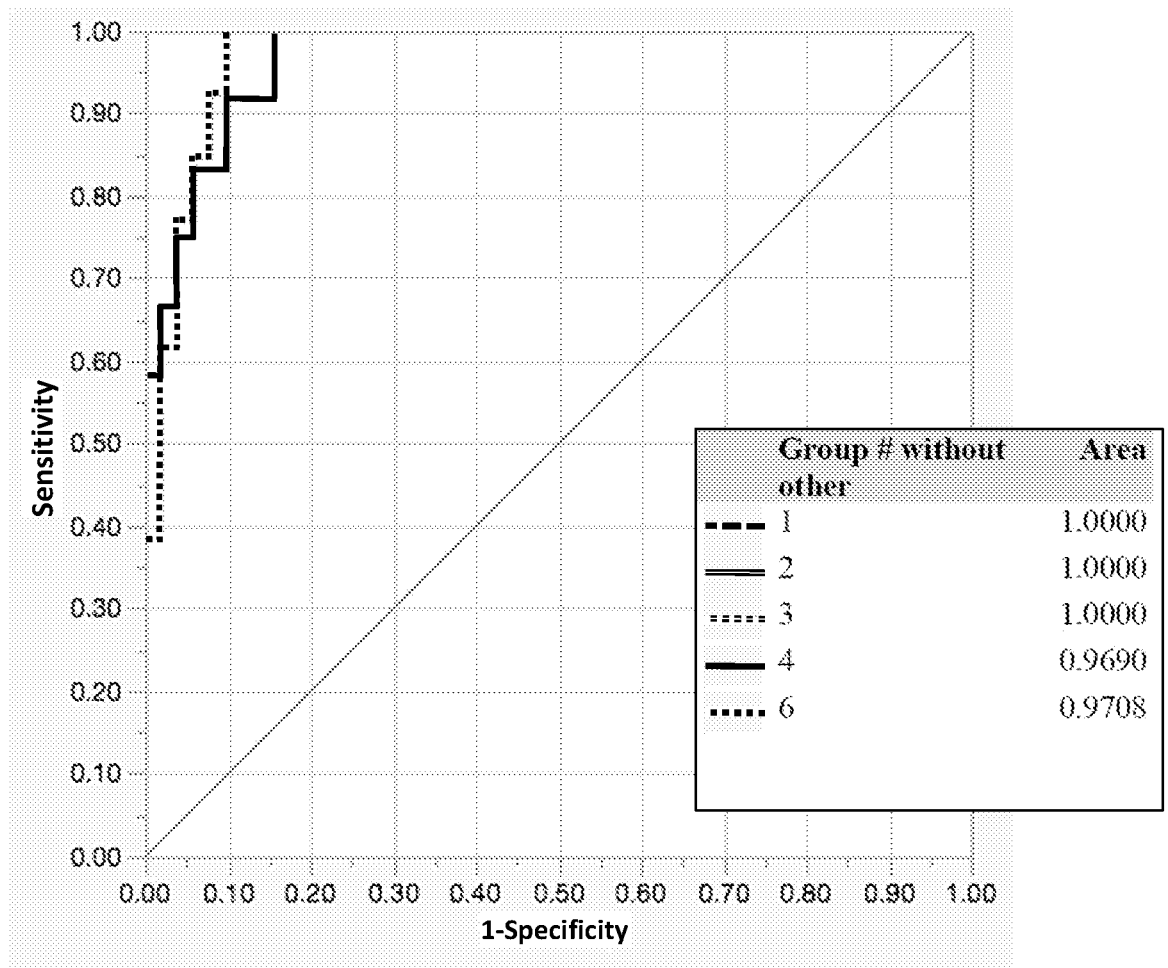
FIG. 4 is a ROC curve using Bayesian covariate predictors for low satiation, behavioral eating, and low resting energy expenditure.

Next, binary classification models were derived that can predict whether a patient belongs to one group over the others. Bayesian covariate predictors were derived for low satiation, behavioral eating, and low resting energy expenditure. These models yielded an ROC AUC of 1 (FIG. 4). These data suggested that the serum metabolite levels hold all the information needed to predict obesity subclasses.

Validation of Biomarkers

To further validate the ability to phenotype obesity based on variables significantly associated with each of the phenotypic groups, the formula was applied to 60 new participants with obesity, and a ROC analysis was done.

FIG. 5 shows that the formula predicted the sub-groups with over 90% sensitivity and specificity.

Summary

These results demonstrate that serum biomarkers can be used to classify obesity patients into obesity phenotype groups.

Example 2: Obesity Phenotypes and Intervention Responsiveness

Obesity is a chronic, relapsing, multifactorial, heterogeneous disease. The heterogeneity within obesity is most evident when assessing treatment response to obesity interventions, which are generally selected based on BMI. These standard approaches fail to address the heterogeneity of obesity. As described in Example 1, obesity phenotypes were associated with higher BMI, distinguish obesity phenotypes. This Example shows that obesity phenotypes respond differently to specific interventions (e.g., pharmacological interventions). Obesity-related phenotypes were evaluated to facilitate the understanding of obesity pathophysiology, and identify sub-groups within the complex and heterogeneous obese population. A novel classification based on identifying actionable traits in the brain-gut axis in humans (see, e.g., Acosta et al., 2015 Gastroenterology 148:537-546 e534; and Camilleri et al., 2016 Gastrointest Endosc. 83:48-56) was applied to understand, in a more homogenous, phenotype-defined population, the unique or specific characteristics within each sub-group of obesity.

The specific characteristics of 180 participants with obesity (defined as BMI>30 kg/m$^2$) were grouped based on their predominant obesity-related phenotype, based on a multiple step process (in addition to gender) to generate a homogeneous populations based on the 75$^{th}$ percentile within the obese group for each well-validated variable: a) satiation [studied by nutrient drink test (maximal tolerated volume, 1 kcal/ml)], b) satiety [studied by gastric emptying ($T_{1/2}$, min)], c) hedonic (hospital anxiety and depression score [HADS] questionnaire), d) other (none of the above) and e) mixed (two or more criteria met).

The overall cohort demographics were as described in Example 1. Then, with the intention to validate further the applicability of the obesity phenotypes, the fact that each sub-group may have unique abnormalities compared to the other groups when tested with previously validated or reported findings in common obesity was interrogated.

Abnormal Satiation Group

Figure 6:
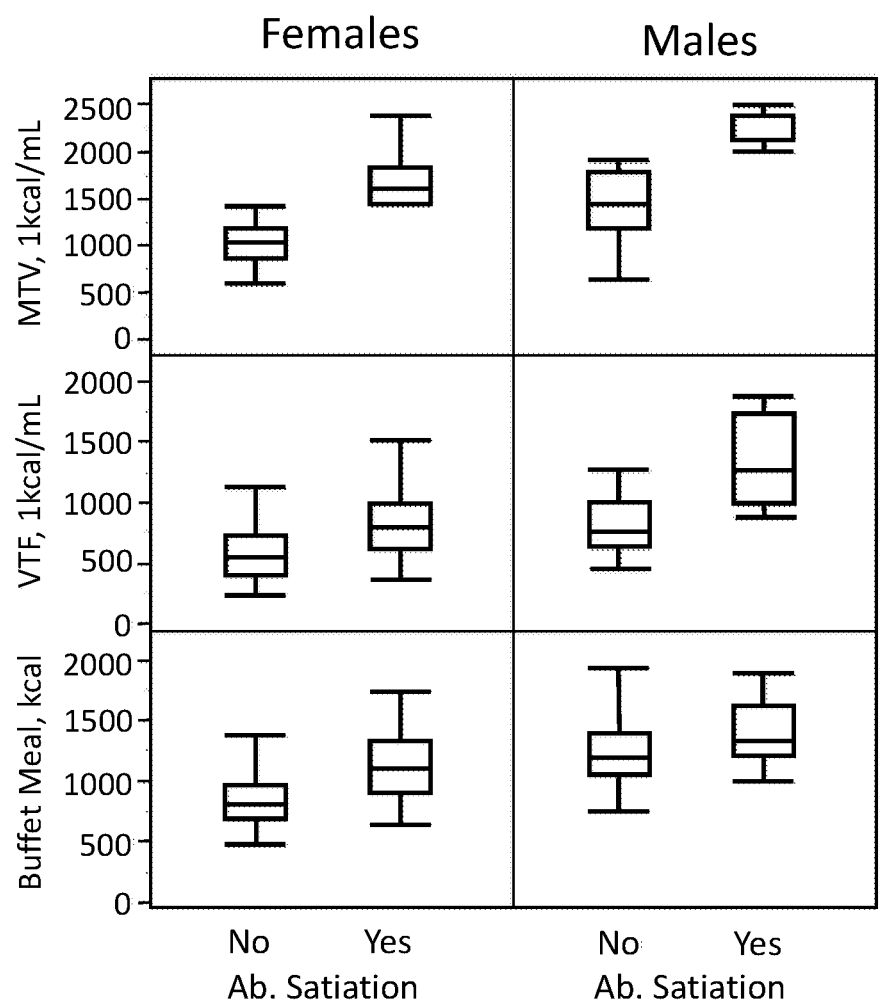
FIG. 6 shows food intake meal paradigms measuring 'maximal' fullness (MTV), 'usual' fullness (VTF) in a nutrient drink test and 'usual' fullness to mixed meal (solids) in an ad libitum buffet meal.

Individuals with obesity typically consume more calories prior to reach 'usual' fullness—for every 5 kg/m$^2$ of BMI increase, participants consumed 50 calories more (see, e.g., Acosta et al., 2015 Gastroenterology 148:537-546). Here, participants with obesity and abnormal satiation were compared to the other groups with the same validated two food intake (meal) paradigms test to measure satiation (FIG. 6A). During a nutrient drink test, females with abnormal satiation consumed 235 calories more prior to reach 'usual' fullness (p<0.001) and 600 calories more prior to reach 'maximal' fullness (p<0.001); males with abnormal satiation consumed 514 calories more prior to reach 'usual' fullness (p<0.001) and 752 calories more prior to reach 'maximal' fullness (p<0.001) compared to individuals with obesity and normal satiation. During the ad libitum buffet meal, females with abnormal satiation consumed 287 calories more prior to reach fullness (p<0.001) and males consumed 159 calories more prior to reach fullness (p=0.03) compared to individuals with obesity and normal satiation. Within obesity the sub-group with abnormal—or lack of—satiation consumed significant more calories in one meal, suggesting a deficiency in the stop signals and a hungry brain phenotype.

Abnormal Satiety Group

Figure 7A:
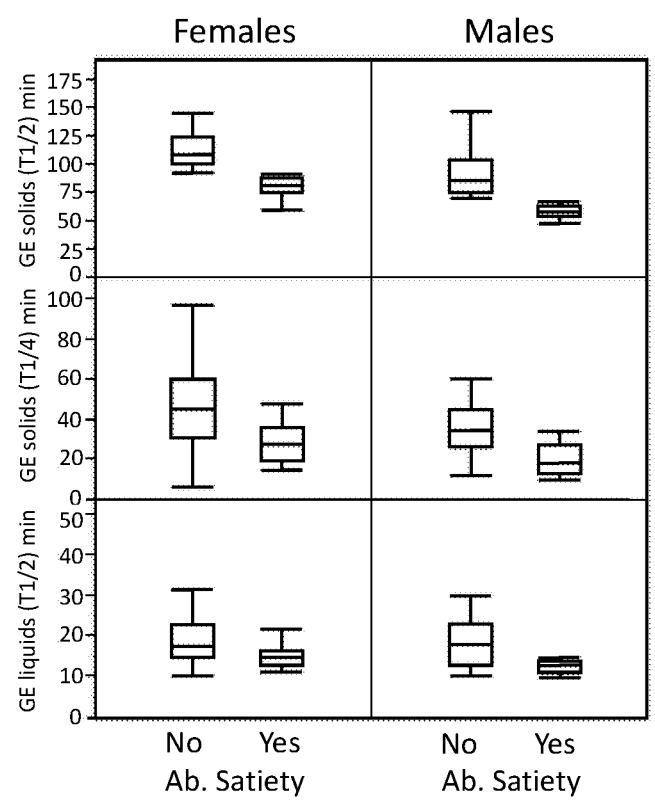
FIGS. 7A-7D shows abnormal satiety deeper phenotypes. A) Gastric emptying (GE) of solid T1/2 and T1/4, GE of liquids T1/5 for females and males. B) Fasting and postprandial gastric volume for females and males. C) Postprandial PYY3-36 and GLP-1 at 90 minutes. D) correlation of Postprandial PYY3-36 at 90 minutes and food intake by a nutrient drink test.
Figure 7B:
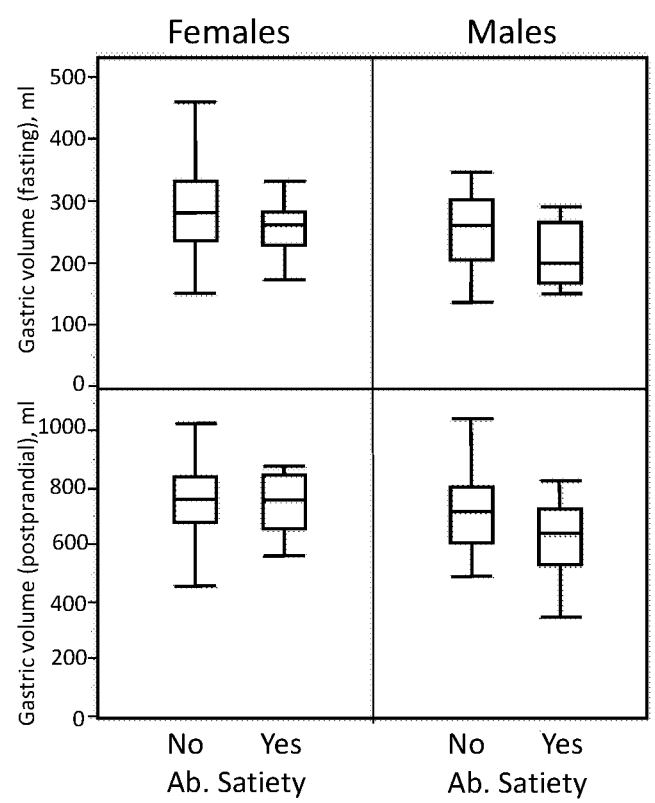
Figure 7C:
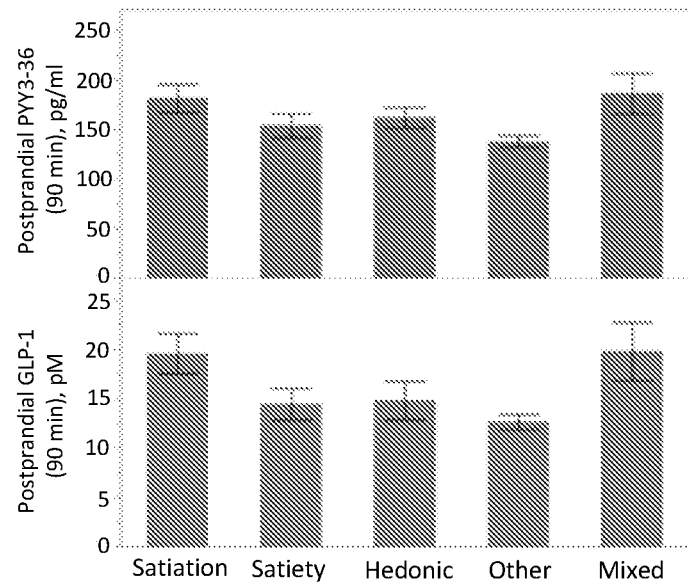
Figure 7D:
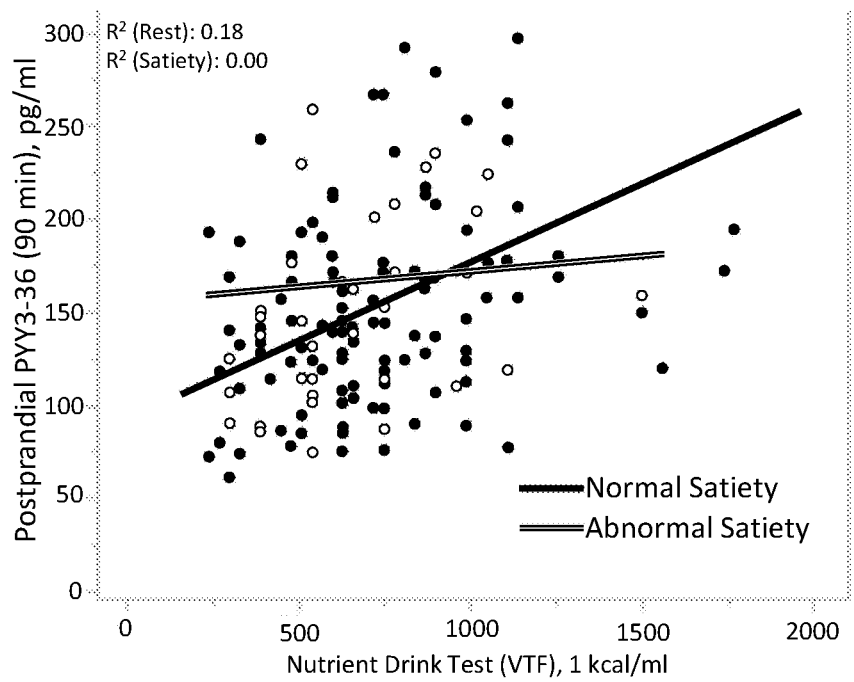

Accelerated gastric emptying was chosen as a surrogate for abnormal satiety based on the main fact that is an objective, reproducible test, whiles other tests, such as visual analog scores are subjective sensations of satiety. In female participants with obesity and abnormal satiety, their gastric emptying (GE) was 40% GE solids $T^{1/4}$ (p<0.001), 30% GE solids $T^{1/2}$ (p<0.001) and 22% GE liquids $T^{1/5}$ (p=0.01) faster compared to normal satiety. In male participants with obesity and abnormal satiety, their gastric emptying was 44% GE solids $T^{1/4}$(p=0.005), 38% GE solids $T^{1/2}$ (p<0.001) and 33% GE liquids $T^{1/2}$ (p=0.05) faster compared to normal satiety (FIG. 7A). The gastric volume fasting and postprandial is smaller in participants with abnormal satiety compared to those with normal satiety when measured by SPECT (FIG. 7B). Additionally, individuals with abnormal satiety have lower levels of gastrointestinal satiety hormones, GLP-1 (p=0.005) and PYY3-36 (p=0.01) at 90 minutes after a meal. Individuals with abnormal satiation have gastrointestinal satiety hormones similar to historical controls with normal weight (see, e.g., Acosta et al., 2015 Gastroenterology 148:537-546); and individuals in the 'other' group also have very low levels of these hormones, despite of having normal gastric emptying. However, the correlation of food intake when reach 'usual' fullness in the nutrient drink test to the secretion of PYY3-36 is linear (r=0.42, p<0.001) and significant in individuals with normal satiety and this correlation disappear in individuals with normal satiety, suggesting an inadequate response of the PYY3-36 secreting enteroendocrine (EE) cells to the meal challenge. Enteroendocrine (EE) cells are real-time nutrient, bile and microbiota sensors that regulate food intake, brain-gut communication, gastrointestinal motility, and glucose metabolism. EE cell function can be studied indirectly by measuring plasma levels of hormones such as GLP-1 or PYY, and less frequently EE cells are studied as part of whole intestinal tissue. These results suggested a hungry gut phenotype.

Hedonic Group

Figure 8A:
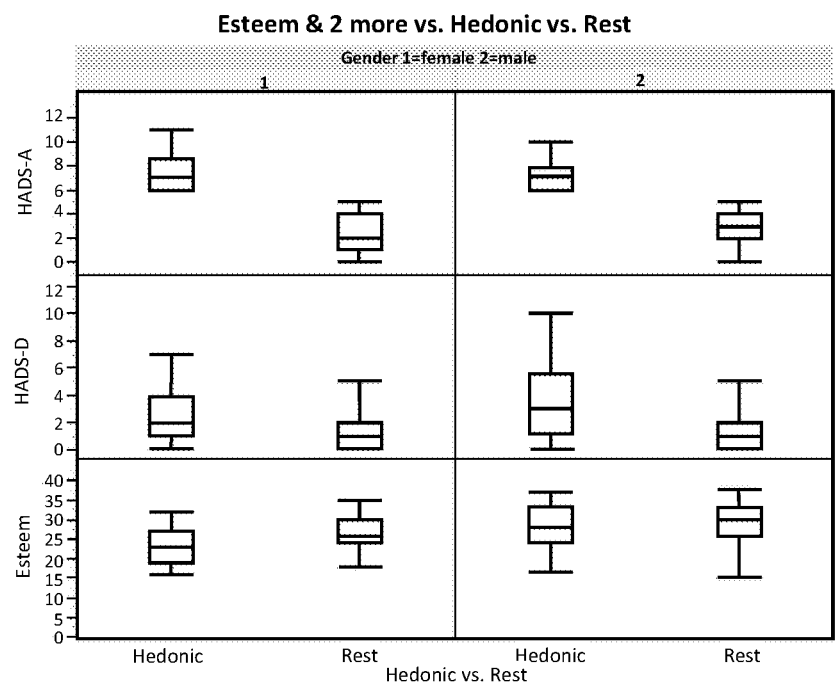
FIGS. 8A-8B show hedonic group deeper phenotypes. A) Anxiety, depression and self-esteem levels and B) fasting serum tryptophan levels in patients with hedonic obesity compared to normal.
Figure 8B:
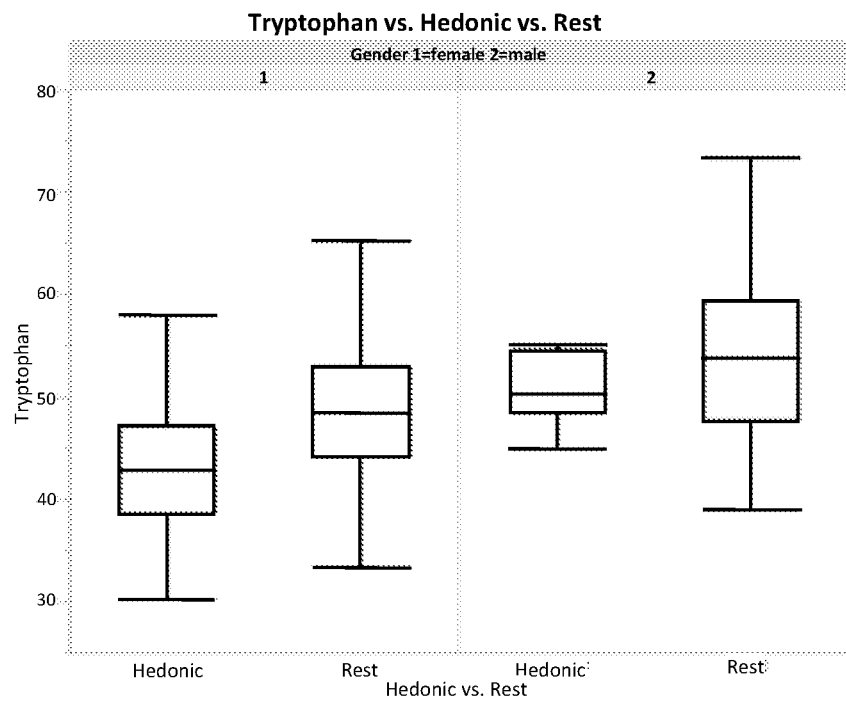

There is a sub-group within participants with obesity which have a very strong psychological component that may predispose them to obesity, labeled here as a 'hedonic' sub-group. Likely this group is acquiring most of their calories from emotional eating, cravings and reward-seeking behaviors while having appropriate sensations of satiation and satiety. Individuals in the hedonic group have higher levels of anxiety ($p<0.001$) and depression ($p<0.001$); and lower levels of self-esteem ($p=0.002$) when compared to other individuals with obesity. The hedonic group has a lower level of serum fasting tryptophan compared to the other groups ($p=0.004$, FIG. 8). Tryptophan is a precursor of serotonin and melatonin, which has been associated with depression, cravings and obesity.

Slow Metabolism Group

Figure 9A:
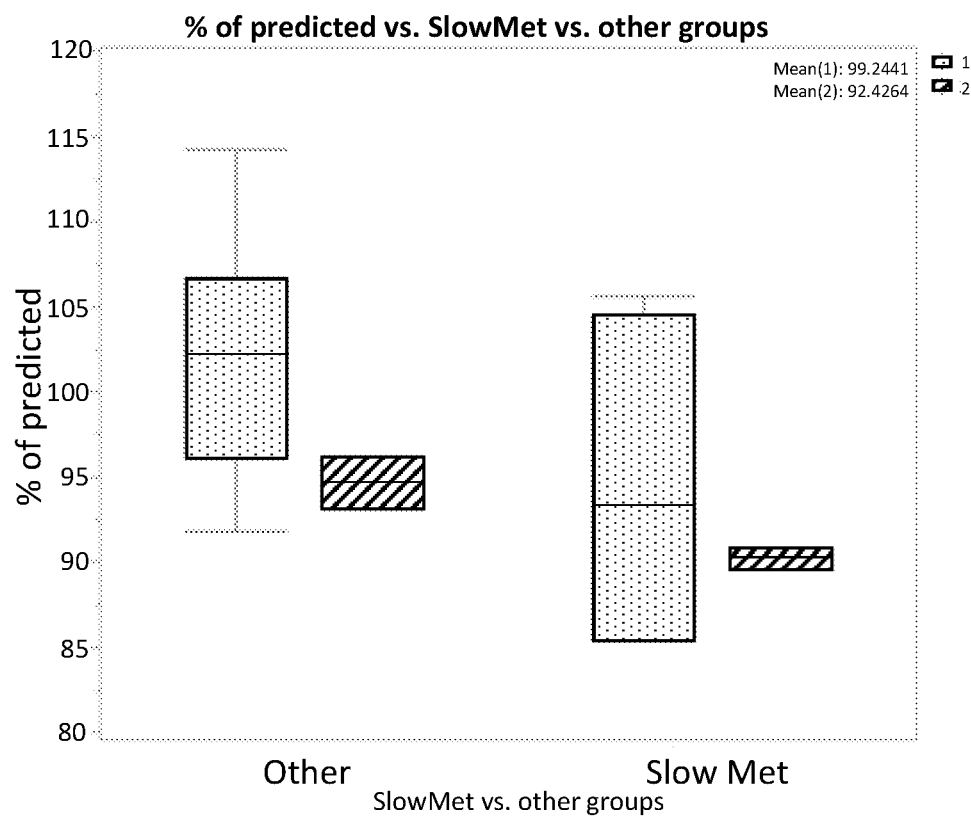
FIGS. 9A-9D show slow metabolism deeper phenotypes. A) Predicted resting energy expenditure in patients with normal metabolism (other) compared to slow metabolism by gender (data in percentage). B) Resting energy expenditure in patients with normal metabolism (other) compared to slow metabolism (data in kcal/day). C) Body composition in different obesity-related phenotypes measured by DEXA. Top row is calculated BMI, med-row is total body fat and lower row is total lean mass. D) Levels of metabolites in patients with slow metabolism compared to normal metabolism (other or rest). Metabolites describes are Alanine, isocaproic acid, phosphoetahnolamine, phenylalanine, tyrosine, alpha-amino-N-butyric acid, sarcasine, and 1-methylhistidine.
Figure 9B:
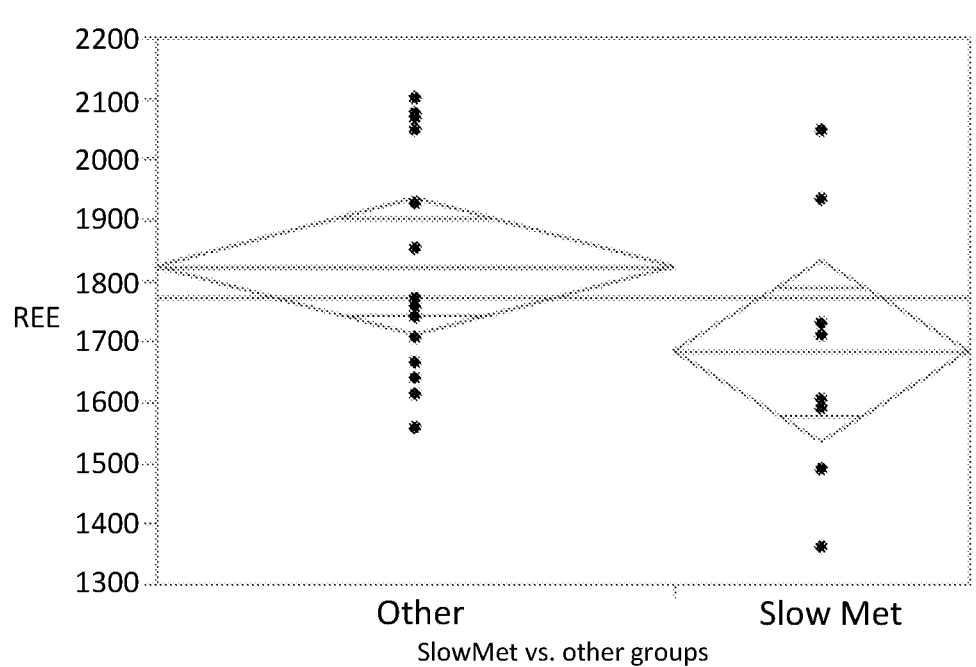
Figure 9C:
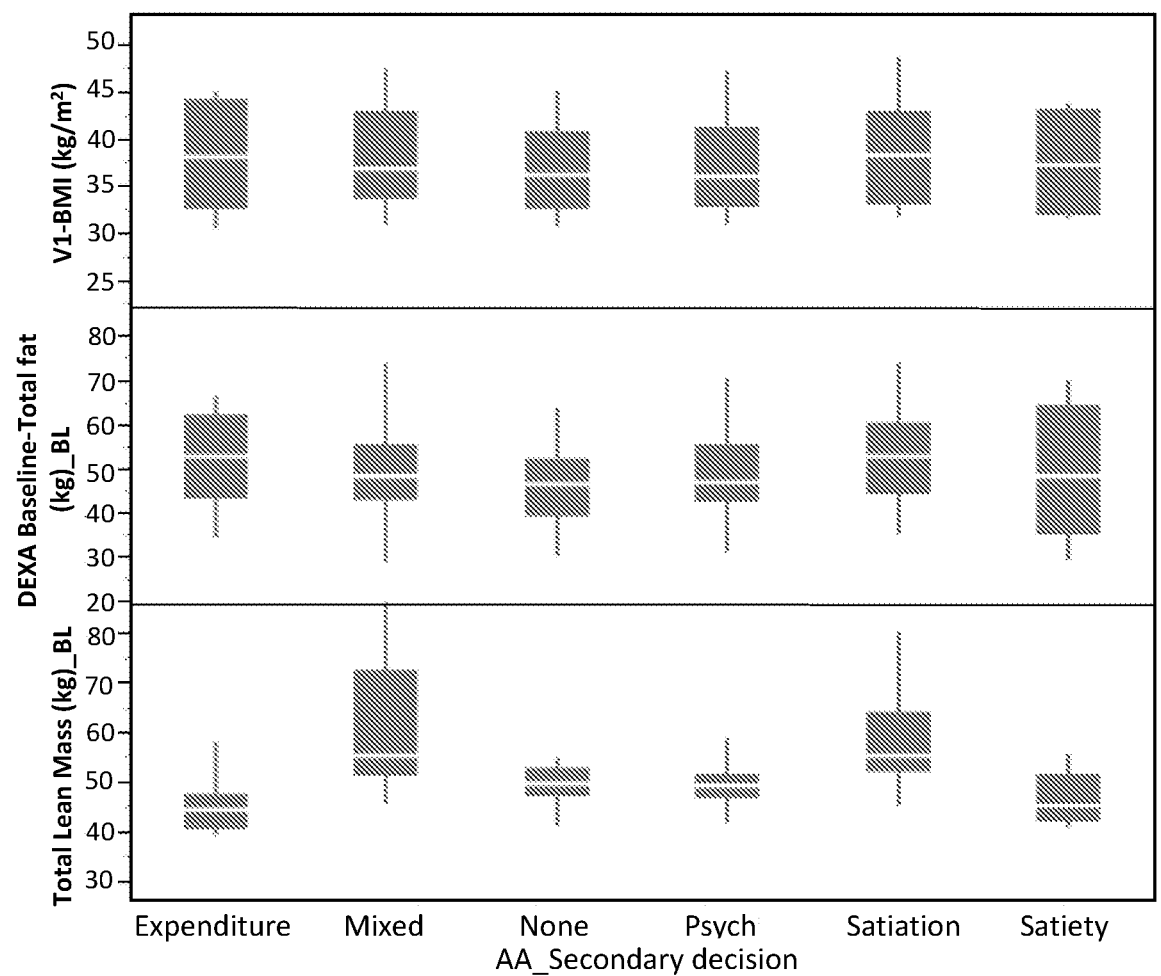
Figure 9D:
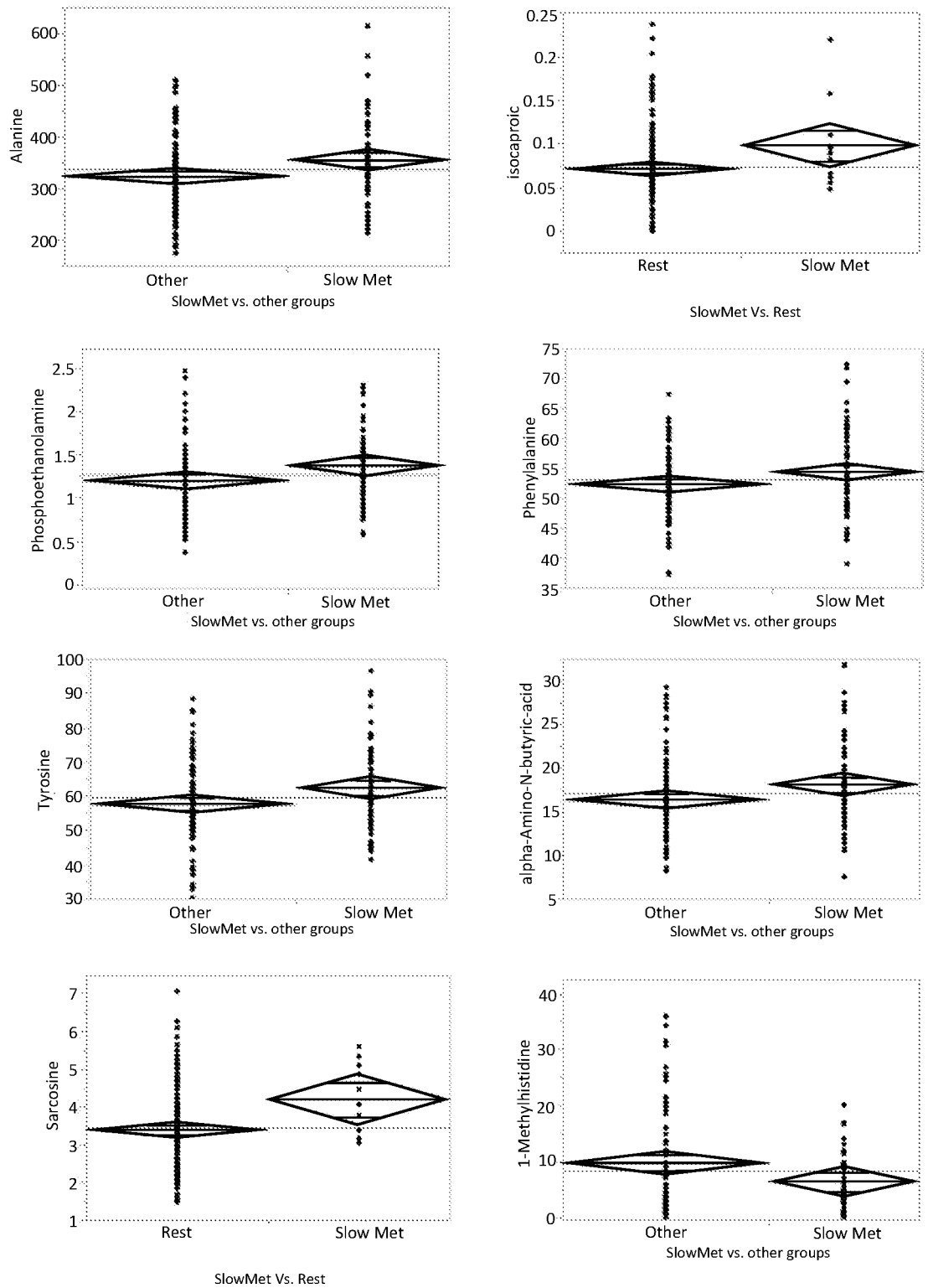
Figure 10:
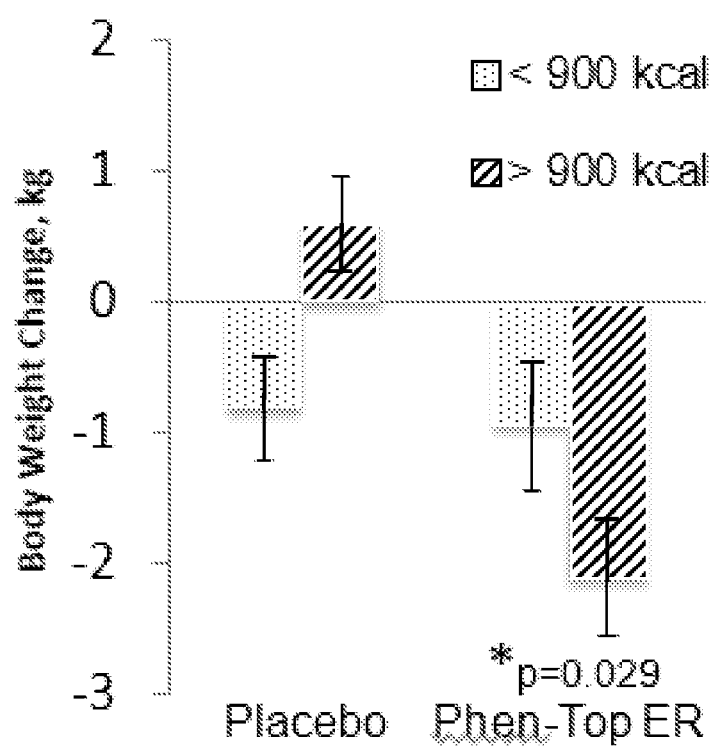
FIG. 10 is a bar graph showing body weight change in response to treatment with placebo or a combination of phentermine and topiramate (PhenTop) and kcal intake at prior ad-libitum meal (satiation test).

A sub-cohort of our population who completed indirect calorimetry testing was studied and individuals in the slow metabolism group have significant lower resting energy expenditure (90% of predicted) compared to the other groups of obesity (100% of predicted, $p=0.032$) were identified (FIG. 9A). The slow metabolism group have significant lower measured resting energy expenditure (kcal/day) that other groups ($p<0.05$) (FIG. 9B). Individuals with slow metabolism have lower systolic blood pressure ($p=0.019$), higher heart rate ($p=0.05$) higher self-steem ($p=0.004$). When body composition was measured using a dexa scan, there was not difference in calculated BMI or measured total fat mass among the obesity groups, however, individuals with slow metabolism had lower muscle (lean) mass compared to the other obesity groups (ANOVA $p<0.05$), FIG. 9C). Metabolites in patients with slow metabolism compared to normal metabolism (other or rest) were significant different ($p<0.05$): higher than other groups: alanine, iso-caproic acid, phosphoetahnolamine, phenylalanine, tyrosine, alpha-amino-N-butyric acid, sarcasine, and lower than other groups: 1-methylhistidine (FIG. 9D).

Obesity Phenotypes Biomarker

The applicability of obesity-related phenotypes as actionable biomarkers was tested in three pilot, proof of concept studies (see, e.g., Acosta et al., 2015 *Gastroenterology* 148:537-546; Acosta et al., 2015 *Physiol Rep* 3; and Halawi et al., 2017 *Lancet Gastroenterol Hepatol* 2:890-899). First, in a single-center, randomized, parallel-group, double-blind, placebo-controlled, 14-day study, the effects of Phentermine-topiramate-ER (PhenTop) (7.5/46 mg, orally, daily) on gastric emptying (GE) and volume, satiation, satiety, and fasting and postprandial GI hormones was evaluated in 24 obese adults. Patients with an abnormal baseline satiation test had greater mean weight loss to PhenTop ER compared to those with normal satiation ($p=0.03$). In a second placebo-controlled trial, the effect of exenatide was studied, 5 µg SQ, twice daily for 30 days, on GE, satiety, satiation and weight loss in 20 obese participants with obesity and abnormal satiety. The average weight loss was 1.3 kg for exenatide and 0.5 kg for the placebo group ($p=0.06$), suggesting that patients with abnormal satiety may be good candidates for weight loss with a GLP-1 receptor agonist). Subsequently, in a prospective, NIH-funded, randomized, placebo controlled clinical trial to study the effects of liraglutide 3 mg, SQ, over 16 weeks on obesity phenotypes and weight in 40 obese patients. Compared to placebo, liraglutide delayed GE of solids at 5 ($p<0.0001$) and 16 ($p=0.025$) weeks, caused significant weight loss and increased satiation. At 5 and 16 weeks, GE $T_{1/2}$ correlated with change in weight loss on liraglutide (all $p<0.02$). These results demonstrate that obesity-related phenotypes can predict response to obesity pharmacotherapy.

Phentermine-Topiramate and Obesity Phenotypes

The effects of phentermine-topiramate-ER (PhenTop) (7.5/46 mg, orally, daily) was evaluated on GE, GV, satiation, satiety, and fasting and postprandial gut hormones as described elsewhere (see, e.g., Acosta et al., 2015 *Gastroenterology* 148:537-546). PhenTop was associated with reduced food intake at buffet meal (mean Δ260 kcal, $p=0.032$) and delayed GE solids (mean ΔGE4h 6%, $p=0.03$; and ΔGE T½ 19 min, $p=0.057$). There were no significant differences in GV, satiation, GE of liquids and GI hormones. Patients on PhenTop had greater mean weight loss of 1.4 kg than placebo ($p=0.03$). Weight loss on PhenTop was significantly associated with kcal intake at a prior satiety test. These results demonstrate that PhenTop reduces food intake and delays GE of solids, indicating that patients having an obesity phenotype of Group 1 (low satiation), are likely responsive to treatment with PhenTop.

Exenatide and Obesity Phenotypes

Figure 11:
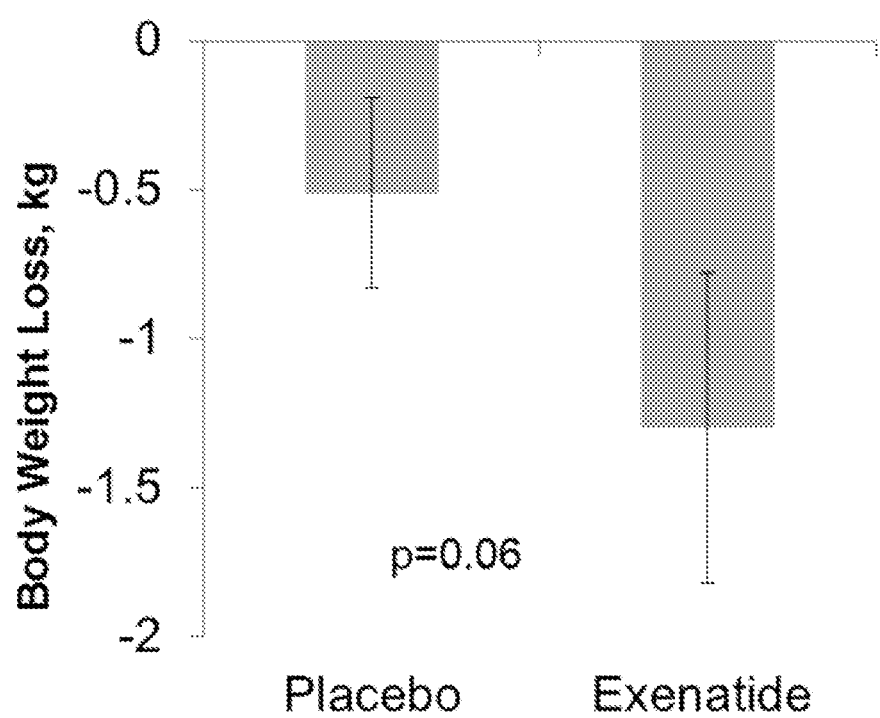
FIG. 11 is a bar graph showing body weight change in response to treatment with placebo or exenatide in patients with a particular obesity phenotype.

The effects of exenatide (5 µg, SQ, twice daily for 30 days) was evaluated on GE, satiety, and weight loss as described elsewhere (see, e.g., Acosta et al., 2015 *Physiological Rep.* 3(11)). Exenatide, a glucagon-like peptide-1 (GLP-1) agonist, had a very significant effect on GE of solids ($p<0.001$) and reduced calorie intake at a buffet meal by an average 130 kcal compared to placebo. The average weight loss was 1.3 kg for exenatide and 0.5 kg for the placebo group (FIG. 11). These results demonstrate that exenatide reduces food intake and delays GE of solids, indicating that a prior accelerated gastric emptying test predicts weight loss with exenatide; see, also, Acosta et al., 2015 *Physiological Rep.* 3(11)).

Surgery and Obesity Phenotypes

The best responders to the intragastric balloon therapy were identified as described elsewhere (see, e.g., Abu Dayyeh et al., "Baseline Gastric Emptying and its Change in Response to Diverse Endoscopic Bariatric TherapiesGastric Emptying Predict Weight Change Response to Endoscopic Bariatric Therapies in a Large Cohort," IFSO annual meeting, 2015) as individuals with an accelerated gastric emptying ($p<0.001$) and the greater delay in gastric emptying after intragastric balloon placement ($p<0.001$).

Liraglutide and Obesity Phenotypes

A prospective, randomized clinical trial with liraglutide, a long-acting GLP-1 receptor agonist, was completed. The effects of liraglutide and placebo were compared over 16 weeks on gastric motor functions, satiation, satiety and weight in obese patients. The study was a randomized, double-blind, placebo-controlled trial of subcutaneous liraglutide, 3 mg, with standardized nutritional and behavioral counseling. Forty adult, otherwise healthy local residents with BMI≥30 kg/m² were randomized. Liraglutide or placebo was escalated by 0.6 mg/day each week for 5 weeks and continued until week 16. At baseline and after 16 weeks' treatment, weight, gastric emptying of solids (GES, primary endpoint), large fasting gastric volumes, satiation, and satiety were measured. GES was also measured at 5 weeks. Statistical analysis compared treatment effects using ANCOVA (with baseline measurement as covariate). Effect of liraglutide on GES $T_{1/2}$ at 5 and 16 weeks in the liraglutide group was analyzed by paired t-test. Seventeen participants were analyzed in the liraglutide group (n=19 randomized) and 18 in the placebo group (n=21 randomized).

Compared to placebo, liraglutide retarded GES at 5 (p<0.0001) and 16 (p=0.025) weeks, caused significant weight loss and increased satiation. In 16 weeks, the total body weight loss for the liraglutide group was 6.1±2.8 kg (SD) compared to 2.2±5 kg control group (p=0.0096). There was tachyphylaxis to GES effects of liraglutide from 5 to 16 weeks' treatment. At 5 and 16 weeks, GES $T_{1/2}$ correlated with Δ weight loss on liraglutide (all p<0.02). Nausea was the most common adverse event in the liraglutide group (63.2%) compared to placebo (9.5%). Liraglutide, 3.0 mg, significantly delays GES after 5 and 16 weeks' treatment; effects on weight loss are associated with absolute value of GES $T_{1/2}$ on liraglutide.

These results demonstrate that liraglutide significant weight loss and increased satiation, indicating that a prior low satiety test predicts weight loss with liraglutide.

Individualized Therapy

The identification of obesity-related phenotypes based on an 'actionable' classification and potential applicability for management of obesity could have a significant impact on the obesity epidemic.

FIG. 12 shows exemplary individualized obesity interventions based upon obesity phenotypes.

The algorithm described in Example 1 was applied to 29 new patients with obesity (Table 9). Data from (intervention) pharmacotherapy and controls were acquired retrospectively. Groups were matched for age, gender and BMI. Results were compared the outcome to 66 patients previously treated by obesity experts.

TABLE 9

Obesity Patient Characteristics.

| Demographics | Cases | Historical Controls | P value |
|---|---|---|---|
| N | 55 | 175 | |
| Age | 46 ± 1.8 | 50 ± 1 | 0.03 |
| Gender (F) | 67% | 73% | |
| Race (W) | 93% | 89% | |
| Weight (kg) | 115 ± 3 | 116 ± 1.8 | |
| BMI | 39.8 ± 1 | 41.6 ± 0.6 | |
| Co-morbidities % (DM/HTN/DJD/OSA/HLD)* | 47/41/45/49/36 | 43/33/35/36/30 | |
| MEDS % | 24 | 22 | |
| Phentermine | 25 | 23 | |
| Phen-Top ER | 6 | 10 | |
| Lorcaserin | 19 | 25 | |
| Liraglutide 3 mg | 12 | 4 | |
| Bupropion-Naltrexone SR | 4 | 6 | |
| Other | | | |

Ns: not statistical significant difference

Figure 13:
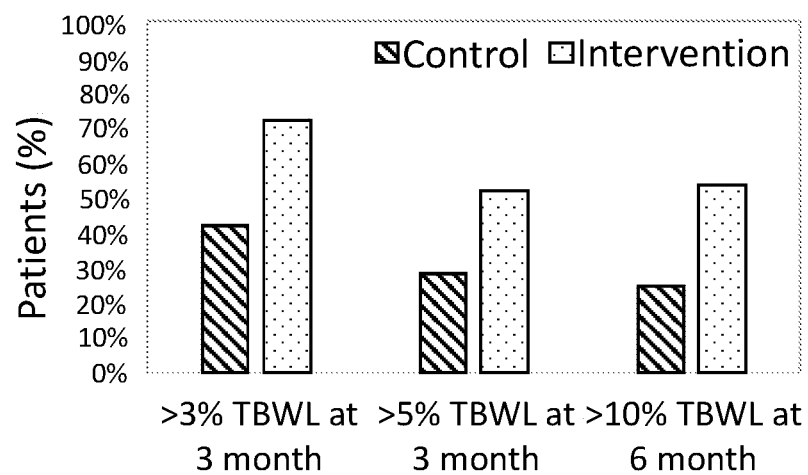
FIG. 13 is a bar graph showing total body weight loss (TBWL) in response to individualized intervention based on pre-selecting the specific individual patient's obesity analyte signature.
Figure 14:
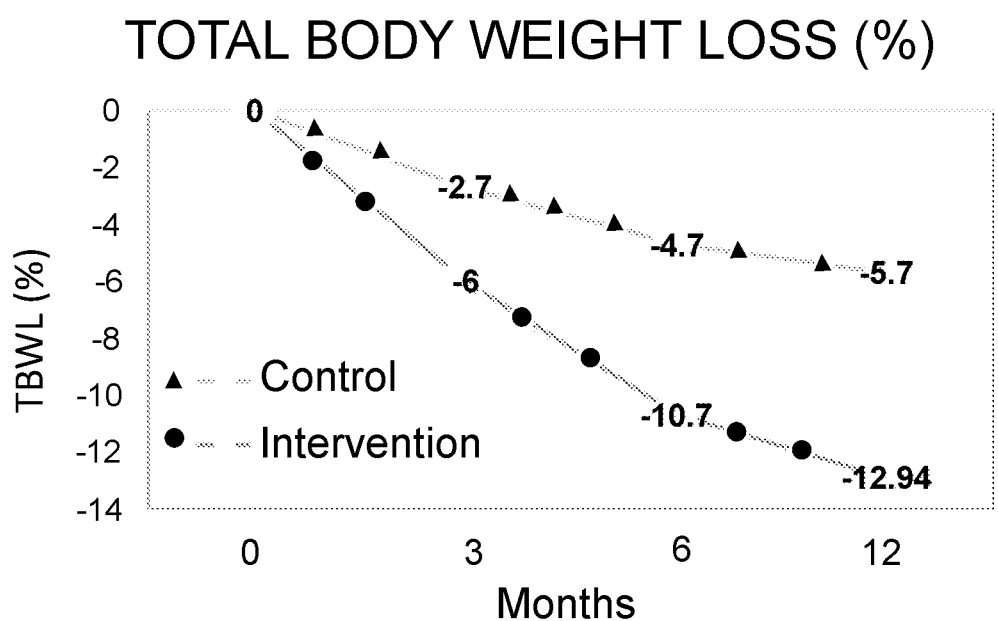
FIG. 14 is a line graph showing TBWL in response to individualized intervention over time.

The algorithm predicted the obesity group and intervention responsiveness of the new participants with over 90% sensitivity and specificity (FIG. 13, FIG. 14, and Table 10). The controls were seen in the weight management clinic by a physician expert of obesity and offered standard of care for obesity management and pharmacotherapy. The current standard of care suggests that pharmacotherapy needs to be selected based on patient-physician preference, mainly driven by side effects and other comorbidities. The cases were seen in the weight management clinic by a physician expert of obesity and offered obesity-phenotype guided pharmacotherapy for obesity management. The phenotypes seen were abnormal satiation (25%), abnormal satiety (20%), abnormal behavior (20%) and other (35%).

TABLE 10

Total body weight in response to individualized intervention.

| Total Body Weight Loss, % | Controls | Cases | P value |
|---|---|---|---|
| 3 months (# patients) | 2.7 ± 0.5 (66) | 6.1 ± 0.8 (29) | 0.0008 |
| 6 months (# patients) | 4.7 ± 0.7 (57) | 10.7 ± 1.2 (22) | 0.0001 |
| 9-12 months (# patients) | 5.7 ± 1.2 (36) | 12.9 ± 1.9 (15) | 0.0025 |

The intervention group had 74% responders (defined as those who loss more than 3% in the first month) compared to 33% in the control group. The control group number of responders was similar to the published in the current obesity literature. The significant improvement of responders resulted in a total body weight loss of 12.9 kg in the intervention group compared to 5.8 kg in the control group at 9 months.

The algorithm was also applied to 12 patients with obesity, who saw their weight loss plateau during the treatment for obesity with an intragastric balloon. These individuals saw weight loss plateau during month 3 and 6 of treatment with the balloon. At month 6, the algorithm was applied to the intervention group compared to the controls.

Summary

It was found that obesity can be sub-grouped in: abnormal satiation (16%), abnormal satiety (16%), hedonic (19%), slow metabolism (32%) and mixed group (17%). Deeper characterization within each subgroup identifies specific disturbances of function. Thus, in the group with abnormal satiation measured by two different feeding paradigms (ad libitum buffet meal and nutrient drink test), compared to lean controls and other groups of obesity; this is summarized as "hungry brain phenotype". In the group with abnormal satiety, there is a suboptimal response of the gut to food intake, manifested as accelerated gastric emptying and decrease in peak postprandial levels of satiety hormones suggesting a "hungry gut phenotype". In the hedonic group, there are increased levels of anxiety, depression, and cravings with low levels of serum tryptophan compared to the other groups. The slow metabolism group has decreased resting energy expenditure compared to other groups. Since identifying the obesity subgroups by deep phenotyping is limited to few academic centers, a fasting blood multi-omic test was developed and validated that predict the obesity subgroups (ROC>90% AUC). This blood test provides segmentation of diverse sub-phenotypes of obesity, has the potential to select patients for individualized treatment from the sea of obesity heterogeneity, facilitates our understanding of human obesity, and may lead to future treatment based on actionable biomarkers.

These results demonstrate that obesity phenotype groups can be used to predict treatment response, and can be used to guide individualized treatment strategies (e.g., pharmacotherapy and/or bariatric endoscopy). The obesity phenotype guided intervention doubled the weight loss in patients with obesity.

Example 3: Obesity Phenotypes and Patient Sub Populations

To validate further the applicability of the obesity phenotypes, the fact that each sub-group may have unique abnormalities compared to the other groups when tested with previously validated or reported findings in common obesity was interrogated.

The model described above was run independently for female and male sub-populations of patients. Characteristics of a complete population is as denoted in Table 11.

TABLE 11

Whole Cohort (181 patients).

| Trait | Mean + SD | >2 SD | # pts | Median | >90% | #pts w/ trait | % pts | >75% | #pts w/ trait | % pts |
|---|---|---|---|---|---|---|---|---|---|---|
| HADS-A | 3.4 + 2.5 | 9 | 17 | 3 | 7 | 29 | 16% | 6 | 46 | 25% |
| HADS-D | 1.54 + 1.74 | 5 | 20 | 1 | 4 | 25 | 14% | 3 | 24 | 13% |
| VTF | 706 + 296 | 1337 | 9 | 630 | 1080 | 21 | 12% | 900 | 44 | 24% |
| MTV | 1286 + 417 | 2142 | 13 | 1272 | 1896 | 24 | 13% | 1539 | 46 | 25% |
| VAS - Full | 70 + 14 | −40 | 2 | 72 | 48 | 18 | 10% | 61 | 44 | 24% |
| SGE T1/2 | 99.5 + 25.8 | −47 | 5 | 98 | 70.8 | 17 | 9% | 81 | 43 | 24% |
| Buffett | 917 + 295 | 1604 | 16 | 916 | 1357 | 23 | 13% | 1184 | 44 | 24% |

Unique analytes were identified when this cohort was separated into female and male sub-populations as shown in Table 12 and Table 13.

TABLE 12

Female sub-population (134 patients).

| Trait | Mean + SD | >2 SD | # pts | Median | >90% | #pts w/ trait | % pts | >75% | #pts w/ trait | % pts |
|---|---|---|---|---|---|---|---|---|---|---|
| HADS-A | 4 | 9 | | 3 | 7 | 20 | 15% | 6 | 34 | 25% |
| HADS-D | 2 | 5 | | 1 | 4 | 13 | 10% | 2 | 30 | 22% |
| VTF | 632 | 1123 | | 600 | 990 | 14 | 10% | 750 | 40 | 30% |
| MTV | 1174 | 1879 | | 1185 | 1618 | 13 | 10% | 1422 | 35 | 26% |
| VAS - Full | 70 | 39 | | 72 | 49 | 14 | 10% | 61 | 34 | 25% |
| SGE T1/2 | 105 | 56 | | 102 | 77 | 14 | 10% | 90 | 32 | 24% |
| Buffett | 896 | 1394 | | 848 | 1279 | 13 | 10% | 1028 | 34 | 25% |

TABLE 13

Male sub-population (47 patients).

| Trait | Mean + SD | >2 SD | # pts | Median | >90% | #pts w/ trait | % pts | >75% | #pts w/ trait | % pts |
|---|---|---|---|---|---|---|---|---|---|---|
| HADS-A | 4 | 9 | | 4 | 7 | 8 | 17% | 6 | 12 | 26% |
| HADS-D | 2 | 7 | | 2 | 5 | 6 | 13% | 3 | 17 | 36% |
| VTF | 959 | 1659 | | 900 | 1524 | 4 | 9% | 1125 | 11 | 23% |
| MTV | 1626 | 2517 | | 1659 | 2180 | 4 | 9% | 1951 | 11 | 23% |
| VAS - Full | 69 | 41 | | 72 | 47 | 4 | 9% | 63 | 11 | 23% |
| SGE T1/2 | 83 | 34 | | 78 | 56 | 6 | 13% | 68 | 11 | 23% |
| Buffett | 1248 | 1893 | | 1222 | 1693 | 4 | 9% | 1469 | 11 | 23% |

When analytes were identified in female and male sub-populations, the concentration of metabolites differed. See the concentrations as shown in Table 14.

TABLE 14

Concentrations of analytes in targeted metabolites.

| analyte | highest standard concentration | lower limit of quantification (LOQ) | Coefficient of variation (CV) |
|---|---|---|---|
| Histidine | 930 | 0.155 | 1.2% |
| Hydroxyproline | 930 | 0.155 | 1.5% |
| 1-Methylhistidine | 930 | 0.155 | 0.5% |
| 3-Methylhistidine | 930 | 0.155 | 0.8% |
| Asparagine | 1000 | 0.167 | 0.7% |
| Phosphoethanolamine | 1000 | 0.167 | 0.4% |
| Arginine | 930 | 0.155 | 0.5% |
| Carnosine | 930 | 0.155 | 2.0% |
| Taurine | 930 | 0.155 | 1.5% |
| Anserine | 930 | 0.155 | 2.2% |
| Serine | 930 | 0.155 | 0.7% |
| Glutamine | 4000 | 0.667 | 0.2% |
| Ethanolamine | 930 | 0.155 | 2.0% |
| Glycine | 930 | 0.155 | 1.6% |
| Aspartic Acid | 930 | 0.155 | 0.7% |
| Sarcosine | 930 | 0.155 | 0.4% |
| Citrulline | 930 | 0.155 | 1.6% |
| Glutamic Acid | 930 | 0.155 | 0.6% |
| beta-Alanine | 930 | 0.155 | 0.5% |
| Threonine | 930 | 0.155 | 1.0% |
| Alanine | 930 | 0.155 | 0.5% |
| gamma-Amino-N-butyric-acid | 930 | 0.155 | 1.3% |
| alpha-Aminoadipic-acid | 930 | 0.155 | 0.0% |
| beta-Aminoisobutyric-acid | 930 | 0.155 | 0.4% |

TABLE 14-continued

Concentrations of analytes in targeted metabolites.

| analyte | highest standard concentration | lower limit of quantification (LOQ) | Coefficient of variation (CV) |
|---|---|---|---|
| Proline | 930 | 0.155 | 1.0% |
| Hydroxylysine 1 | 930 | 0.155 | 0.6% |
| Hydroxylysine 2 | 930 | 0.155 | 0.3% |
| alpha-Amino-N-butyric-acid | 930 | 0.155 | 0.0% |
| Ornithine | 930 | 0.155 | 0.9% |
| Cystathionine 1 | 930 | 0.155 | 1.0% |
| Cystathionine 2 | 930 | 0.155 | 0.6% |
| Lysine | 930 | 0.155 | 0.2% |
| Cystine | 930 | 0.155 | 1.7% |
| Tyrosine | 930 | 0.155 | 0.4% |
| Methionine | 930 | 0.155 | 1.2% |
| Valine | 930 | 0.155 | 1.7% |
| Isoleucine | 930 | 0.155 | 2.3% |
| allo-Isoleucine | 930 | 0.155 | 0.9% |
| Homocystine | 930 | 0.155 | 1.0% |
| Leucine | 930 | 0.155 | 0.5% |
| Phenylalanine | 930 | 0.155 | 1.6% |
| Tryptophan | 930 | 0.155 | 1.1% |
| Acetylcholine | 1600 | 0.10 | 5.6% |
| Adenosine | 1600 | 0.10 | 0.5% |
| Norepinephrine | 1600 | 0.10 | 1.0% |
| Dopamine | 1600 | 0.10 | 0.7% |
| Serotonin | 1600 | 0.10 | 1.0% |
| acetic acid | 6651 | 5.5 | 25% |
| propionic acid | 4955 | 1.03 | 7% |
| isobutyric acid | 4792 | 1.00 | 2% |
| butyric acid | 5379 | 1.12 | 4% |
| isovaleric acid | 4030 | 0.84 | 15% |
| valeric acid | 5393 | 1.12 | 5% |
| isocaproic acid | 3532 | 0.74 | 12% |
| caproic acid | 2901 | 0.60 | 8% |

Unique targets identified in a sub-population can serve to find a unique treatment: for example TCF7L/2 genetic variant can be used to identify a group with abnormal satiety; or a simple test such as gastric emptying can be used to define abnormal satiety.

The model described above is also run independently for additional sub-populations of patients. For example, the model can be run on patients of specific ages (e.g., youth such as people from birth to about 18, adults such as people 18 or older), and specific life stages (e.g., perimenopausal women, menopausal women, post-menopausal women, and andropausal men).

Sub-populations of patients demonstrated analyte differences between obesity groups that were not seen in a full population of patients.

Example 4: Selecting Treatment(s) for Obesity Therapy

When an individual is treated with any weight loss intervention, his/her phenotype can assist in selecting a treatment.

Study Design

In a 12 week, randomized, double-blinded, active controlled trial, with 9 month open-label extension of 200 participants with obesity; the weight loss response rate to obesity-phenotype-guided pharmacotherapy (intervention) vs. non-phenotype guided (randomly selected) pharmacotherapy (control) in patients with obesity is compared. All 200 participants are phenotyped and the medication selection is randomly and double blinded (to physician, study team, and participant) to the FDA-approved medicine suggested by the phenotype or to another FDA-approved medicine not suggested by the phenotype.

All participants receive a standard intense lifestyle intervention, which consists of 2 visits with registered dietitian. The phenotypic studies include (all performed in same day in the following order): fasting blood collection, resting energy expenditure, gastric emptying with meal for breakfast, behavioral questionnaires, and buffet meal test for lunch. Blood is collected for assessment of metabolomic biomarkers, gastrointestinal hormones, DNA (blood and buccal swab), and pharmacogenomics. Stool samples are collected for microbiome and bile acid. Participants return to the CRTU to pick up medication based on the randomization and discuss the pharmacogenomics results. All participants are contacted at 4 and seen at 12 weeks (current standard in practice). A stool sample and a fasting blood sample are collected at the 12-week visit. At the 12-week visit, participants will be unblinded to their "obesity-related phenotype" and they could contact their physician to continue a FDA-approved medication as part of clinical care. Study team will prospectively follow the patients' weight, waist circumference and use of obesity medications every 3 months for 1 year.

Randomization and Allocation

A computer generated randomization is based on guiding pharmacotherapy based on the phenotype or randomly as current standard of care. Allocations are concealed.

Participants

A study cohort includes 200 patients with obesity (BMI>30 kg/m$^2$). Participants that agree to pharmacotherapy treatment are invited to participate in the phenotypic assessment of their obesity that will guide (or not) the pharmacotherapy.

Inclusion Criteria
 a) Adults with obesity (BMI>30 Kg/m$^2$); these are otherwise healthy individuals with no unstable psychiatric disease and controlled comorbidities or other diseases.
 b) Age: 18-75 years.
 c) Gender: Men or women. Women of childbearing potential have negative pregnancy tests within 48 hours of enrolment and before each radiation exposure.

Exclusion Criteria
 a) Abdominal bariatric surgery
 b) Positive history of chronic gastrointestinal diseases, or systemic disease that could affect gastrointestinal motility, or use of medications that may alter gastrointestinal motility, appetite or absorption, e.g., orlistat, within the last 6 months.
 c) Significant untreated psychiatric dysfunction based upon screening with the Hospital Anxiety and Depression Inventory (HAD), and the Questionnaire on Eating and Weight Patterns (binge eating disorders and bulimia). If such a dysfunction is identified by an anxiety or depression score>11 or difficulties with substance or eating disorders, the participant will be excluded and given a referral letter to his/her primary care doctor for further appraisal and follow-up.
 d) Hypersensitivity to any of the study medications.
 e) No contraindications to all FDA-approved medications Anthropometrics and Phenotype Studies Anthropometrics Measurements: are taken of hip-waist ratio, height, weight, blood pressure, pulse at baseline, randomization day and week 12.

Phenotype studies at baseline: After an 8-hour fasting period, and the following validated quantitative traits (phenotypes) are measured at baseline:

a) The DEXA scan (dual energy x-ray absorptiometry) measures body composition.
b) Resting energy expenditure: is assessed by indirect calorimetry with a ventilated hood.
c) Gastric emptying (GE) of solids by scintigraphy: The primary endpoint is gastric half-emptying time (GE $t_{1/2}$) as described elsewhere (see, e.g., Acosta et al., 2015 *Gastroenterology* 148:537-546; Vazquez et al., 2006 *Gastroenterology* 131:1717-24; and Camilleri et al., 2012 *Neurogastroenterology and Motility* 24:1076).
d) Appetite (hunger level) by visual analog score fasting and after standard meal for GE and prior to the Satiation test as described elsewhere (see, e.g., Acosta et al., 2015 *Gastroenterology* 148:537-546).
e) Satiation is measured by ad-libitum buffet meal to measure total caloric intake and macronutrient distribution in the chosen food. Satiation is reported in calories consumed at fullness (satiation) as described elsewhere (see, e.g., Acosta et al., 2015 *Gastroenterology* 148:537-546).
f) Satiety by visual analog score postprandial after standard meal for GE and after to the Ad-libitum meal test for every 30 minutes for 2 hours as described elsewhere (see, e.g., Acosta et al., 2015 *Gastroenterology* 148:537-546). Satiety is measured in length of time of fullness.
g) Self-administered questionnaires assessing affect, physical activity levels, attitudes, body image, and eating behavior; details of each questionnaire are provided below.
h) Sample collection, handling and storage: Samples are collected after an overnight fast (of at least 8 hours) in the morning. Plasma was preserved following standard guidelines and protein degradation inhibitors, kalikrein and DPP-IV inhibitors are added to preserve the samples. Samples are stored at −80° C.
   a. Plasma gastrointestinal hormones (Total and active Ghrelin, GLP-1, CCK, PYY and bile acids) by radioimmunoassay, measured fasting, and 15, 45, and 90 minutes postprandial, with the primary endpoint being the peak postprandial level (test should be done simultaneously to GE).
   b. Targeted Metabolomics: Targeted metabolomics of salient classes of compounds in plasma samples are performed using mass spectrometry. Amino acids plus amino metabolites are quantified in plasma by derivatizing with 6-aminoquinolyl-N-hydroxysuccinimidyl carbamate according to Waters MassTrak kit. A 10-point calibration standard curve is used for quantification of unknowns using a triple-stage quadrupole mass spectrometer (Thermo Scientific TSQ Quantum Ultra) coupled with an ultra-performance liquid chromatography (UPLC) system (Waters Acquity UPLC). Data acquisition is performed using multiple-reaction monitoring (MRM). Concentrations of 42 analytes in each sample are calculated against their respective calibration curves with a measurement precision of <5%. Essential nonesterified fatty acid (NEFA) concentrations, such as myristic, palmitic, palmetoleic palmitoelaidic, stearic, oleic, elaidic, linoleic, linolenic and arachidonic, are measured against a six-point standard curve by LC/MS/MS, underivatized after extraction from plasma via negative electrospray ionization (ESI) and multiple reaction monitoring conditions. This technique was developed to replace the GC/MS method where NEFAs required methylation before analysis. This technique reduces the uncertainty as to whether the methylation step increases FFA concentrations by inadvertently hydrolyzing other lipid classes. Intra CV is <3% for all analytes.
   c. Blood DNA.
   d. Buccal Swab DNA for OneOme pharmacogenomics testing.
      i. Pharmacogenomics: Patients who have met the inclusion and exclusion criteria provide a one-time buccal scraping. 72 variants in 22 pharmacogenes, with seven cytochrome P450 enzymes (CYP1A2, CYP2B6, CYP2C9, CYP2C19, CYP2D6, CYP3A4, and CYP3A5) covering approximately 90 percent of human drug oxidation and nearly 50 percent of commonly used medications, and 15 genes related to drug action or metabolism (COMT, DPYD, DRD2, F2, F5, GRIK4, HTR2A, HTR2C, IL28B, NUDT15, OPRM1, SLCO1B1, TPMT, UGT1A1, and VKORC1) are assessed. Results for the patient are placed into the patient EHR to be utilized for clinical treatment decisions. Through chart review, including the patient's current medication list as stated in the EHR, previously reported medication inefficacy and intolerance is documented. This data is entered into a database.
   i) Stool is collected and stored to study microbiome, short chain fatty acids, and bile acids.

Studies at 12-Week Visit:
j) Stool and fasting blood sample are collected and stored. Stool is used to measure microbiome, short chain fatty acids and bile acids (as above). Fasting blood will be used to GI hormones and metabolomics (as above).

Questionnaires to Assess GI Symptoms and Behavioral Disorders

Participants complete a series of questionnaires: Weight management Questionnaire (Mayo Clinic®), the and the Hospital Anxiety and Depression Inventory [HAD (see, e.g., Zigmond et al., 1983 *Acta Psychiatrica Scandinavica* 67:361-70)] to appraise the contribution of affective disorder.

Behavioural Questionnaires
a. AUDIT-C Alcoholism Screening Test—This score is used in screening by the study physician/nurse coordinator.
b. Eating Disorders Questionnaire—The Questionnaire on Eating and Weight Patterns-Revised, is a valid measure of screening for eating disorders which has been used in several national multi-site field trials. Respondents are classified as binge eating disorder, purging bulimia nervosa, non-purging bulimia nervosa, or anorexia nervosa.
c. Body Image Satisfaction—The Multidimensional Body-Self Relations Questionnaire provides a standardized attitudinal assessment of body image, normed from a national body-image survey. Items are rated on a 5-point scale, ranging from 1=Definitely Disagree to 5=Definitely Agree. A sub-scale, *the Body Areas Satisfaction Scale*, is used to measure feelings of satisfaction with discrete aspects of physical appearance (e.g., face, weight, hair). Cronbach's a values range from 0.70 to 0.89.
d. Eating Behaviors—The Weight Efficacy Life-Style Questionnaire [WEL] is a 20-item eating self-efficacy scale consisting of a total score and five situational factors: negative emotions, availability, social pressure, physical discomfort, and positive activities. Subjects are asked to rate their confidence about being able to successfully resist the urge to eat using a 10-point scale ranging from 0=not confident to 9=very confident.

e. Physical Activity Level—The four-item Physical Activity Stages of Change Questionnaire will be utilized to assess the physical activity level of participants.

Standard of Care:

All participants receive standard of care which consists of 1) Intense lifestyle intervention, behavioral evaluation and treatment, and a medication as part of the regular clinic management for obesity.

Intense Lifestyle Intervention and Behavioral Treatment

All the participants will meet the multidisciplinary team which consists of an Obesity Expert physician a registered dietitian nutritionist as standard of care in our clinical practice. These appointments will be schedule in the clinic and will not be covered by the current protocol. All participants are guided to 1) Nutrition: Reduce dietary intake below that required for energy balance by consuming 1200-1500 calories per day for women and 1500-1800 calories per day for men; 2) Physical Activity: reach the goal of 10,000 steps or more per day; 3) Exercise: reach the goal of 150 minutes or more of cardiovascular exercise/week; 4) Limit consumption of liquid calories (i.e. sodas, juices, alcohol, etc.).

Pharmacotherapy for Obesity

Pharmacotherapy for the treatment of obesity can be considered if a patient has a body mass index (BMI)≥30 kg/m$^2$ or BMI>27 kg/m$^2$ with a comorbidity such as hypertension, type 2 diabetes, dyslipidemia and obstructive sleep apnea. Medical therapy should be initiated with dose escalation based on efficacy and tolerability to the recommended dose. An assessment of efficacy and safety at 4 weeks is done. In both groups, medications are assessed for drug interactions and potential side effects as standard of care.

Medication selection: Once the phenotype tests are completed the results are filled in an algorithm to assist on the decision of the medication selection as described elsewhere (see, e.g., Acosta et al., 2015 *Gastroenterology* 148:537-546; Camilleri et al., 2016 *Gastrointest. Endosc.* 83:48-56; and Acosta et al., 2015 *Physiological Rep.* 3(11)). An example is below:

Control Group: Pharmacotherapy for Obesity

Standard of care pharmacotherapy for obesity recommends the following doses and regimen for weight loss:

Phentermine: 15-37.5 mg oral daily

Phentermine-Topiramate Extended Release (Qsymia®) at dose of 7.5/46 mg oral daily Oral naltrexone extended-release/bupropion extended-release (NBSR; Contrave®) at dose of 32/360 mg oral daily (divided in 2 tables in morning and 2 tablets in evening)

Liraglutide (Saxenda®) at dose of 3 mg subcutaneous daily

Intervention Group: By Obesity Phenotype Guided Pharmacotherapy

Participants in the intervention group will have 4 tests to assess 1) satiation, 2) satiety/return to hunger, 3) behavioral, or 4) energy expenditure. As described in FIG. 12 pharmacotherapy will by guide based on the phenotype. In case of a mixed pattern or multiple abnormal phenotypes, the most prominent phenotype is tackled.

Algorithm diagnostic:
1. satiation: Phentermine-Topiramate Extended Release (Qsymia®) at dose of 7.5/46 mg oral daily
2. Satiety/return to hunger: Liraglutide 3 mg SQ daily
3. Behavioral/Psychological: Oral naltrexone extended-release/bupropion extended-release (NBSR; Contrave®) at dose of 32/360 mg oral daily (divided in 2 tables in morning and 2 tablets in evening); or
4. Energy expenditure: Phentermine 15 mg daily plus increase physical activity.

Statistical Analyses

Primary endpoint: Total Body Weight Loss, kg (defined as weight changed from baseline to 12 weeks) in the obesity phenotype-guided pharmacotherapy (intervention) vs. the randomly assigned pharmacotherapy (control) group.

The secondary end points will be percentage of responders (defined as number of participants who loss 5% or more of total body weight) compared to baseline in the obesity phenotype guided pharmacotherapy (intervention) group vs. standard of care at 4 and 12 weeks; percentage of responders with at least 10 and 15% at 12 weeks, and 10% at 6 months

| TEST | Abnormal result | Example 1 | Example 2 | Example 3 | Example 4 |
| --- | --- | --- | --- | --- | --- |
| Satiation (Ad libitum Buffet Meal) | >1139 kcal | 1400 kcal | 1000 kcal | 1100 kcal | 1050 kcal |
| Satiety (Gastric emptying) | SGE T$^{1/2}$ <85 min or GE 1 hr >35% | 102 min | 80 min | 105 min | 110 min |
| Behavioral Traits (Questionnaires) | HADS A&D >6 points | 5 | 4 | 9 | 3 |
| Energy Expenditure (Resting EE) | <85% predicted | 92% | 93% | 95% | 82% |
| Phenotype | — | Ab Satiation | Ab Satiety | Ab Psych | Ab E.E. |

Once the decision is made on the "phenotype-guided" medication, pharmacy will assess whether patient is randomized to "intervention" or "control". Based on the randomization, patient picks up the prescription for 3 months. During the 3-month visit, participants are offered a prescription to continue the medication (if randomized to the intervention group) or to switch to the phenotype guided medication (if randomized to the control group). Patients who continue obesity pharmacotherapy are contact every three months for one year to monitor their weight and comorbidities.

and 12 months; percentage of responders at 5%, 10% and 15%; percentage of responders within each obesity-phenotype group at 4 and 12 weeks; and side effects of medications. In the open-label extension, the total body weight loss is assessed at 24 and 52 weeks in both groups.

Statistical Analyses: A randomized, double-blinded, active controlled trial of 200 participants with obesity to compare effects of intervention compared to controls in weight loss. The analysis involves an ANCOVA models, with the response being actual weight change; the covariates to be considered include gender, and BMI (at baseline) at baseline.

Sample size assessment and power calculation: The detectable effect size in weight loss between groups of interest (intervention vs. control) is given in Table 15. Using a SD for the overall weight change (pre-post) of 2.8 kg, the differences between groups that could be detected with approximately 80% power (2-sided a level of 0.05) for main effects are estimated. Thus, the sample size needed is 87 participants per group. In order to account for dropout, 100 participants per group are randomized.

TABLE 15

| Mean difference (Δ) of total body weight loss in controls group (mean average 6.1 kg) vs. intervention group. | Intervention (# of participants) | Control (# of participants) |
| --- | --- | --- |
| Mean difference of 10% [6.7 vs. 6.1 kg] | 343 | 343 |
| Mean difference of 20% [7.3 vs. 6.1 kg] | 87 | 87 |
| Mean difference of 30% [7.9 vs. 6.1 kg] | 39 | 39 |

As each 50 patients complete the 12-week treatment phase, an interim analysis is conducted by the study statistician for the purpose of ensuring (based on the observed coefficient of variation in the primary responses such as the proportion of weight difference of 20%) that the study still has sufficient power based on the sample size proposed in the study.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating obesity in a mammal in need thereof, wherein said method comprises:
    (a) determining an obesity analyte signature unique to a body mass index (BMI) of >30 kg/m$^2$ or a BMI>27 kg/m$^2$ with an obesity-related comorbidity in a sample obtained from said mammal, wherein said obesity analyte signature comprises a behavioral assessment and a plurality of analytes selected from the group consisting of metabolites, gastrointestinal peptides, single nucleotide polymorphisms and any combination of distinct analytes thereof; and
    (b) administering an intervention to said mammal based on said obesity analyte signature determined in step (a), wherein said obesity analyte signature is obtained from a regression model of one or more variables comprising:
        (i) serotonin, glutamine, isocaproic acid, allo-isoleucine, hydroxyproline, beta-aminoisobutyric-acid, alanine, hexanoic acid, tyrosine, and PYY, and excluding 1-methylhistine, gamma-amino-n-butyric-acid, phenylalanine, and ghrelin, and said behavioral assessment does not indicate anxiety on a behavioral questionnaire, and wherein said intervention is a pharmacotherapy selected from the group consisting of an appetite suppressant, an appetite suppressant in combination with an anticonvulsant a melanocortin receptor agonist, CCK analogs and any combination of distinct pharmacotherapies thereof; or
        (ii) 1-methylhistine, allo-isoleucine, hydroxyproline, beta-aminoisobutyric-acid, alanine, and phenylalanine, and excluding serotonin, glutamine, gamma-amino-n-butyric-acid, isocaproic acid, hexanoic acid, tyrosine, ghrelin, and PYY, and said behavioral assessment does not indicate anxiety on a behavioral questionnaire, and wherein said intervention is a pharmacotherapy selected from the group consisting of a GLP-1 analog, GLP-1 receptor agonist, amylin analogs, PYY analogs, Y receptor agonists or antagonists, oxyntomodulin analogs, ghrelin antagonists, TGR5 agonists, FGF-19/21analogs, FXR agonists, GRP-119, GRP-120 and any combination of distinct pharmacotherapies thereof; or
        (iii) serotonin, and excluding 1-methylhistine, glutamine, gamma-amino-n-butyric-acid, isocaproic acid, allo-isoleucine, hydroxyproline, beta-aminoisobutyric-acid, alanine, hexanoic acid, tyrosine, phenylalanine, ghrelin, and PYY, and said behavioral assessment does indicate anxiety on a behavioral questionnaire, and wherein said intervention is a pharmacotherapy selected from the group consisting of an anti-depressant, an opioid antagonist, an anti-anxiety agent, a cannabinoid antagonist and any combination of distinct pharmacotherapies thereof; or
        (iv) 1-methylhistine, glutamine, gamma-amino-n-butyric-acid, isocaproic acid, allo-isoleucine, beta-aminoisobutyric-acid, alanine, hexanoic acid, tyrosine, phenylalanine, and PYY, and excluding serotonin, hydroxyproline, and ghrelin, and said behavioral assessment does indicate anxiety on a behavioral questionnaire, and wherein said intervention is a pharmacotherapy selected from the group consisting of an anti-depressant, an opioid antagonist, an anti-anxiety agent, a cannabinoid antagonist and any combination of distinct pharmacotherapies thereof; or
        (v) 1-methylhistine, serotonin, glutamine, gamma-amino-n-butyric-acid, isocaproic acid, allo-isoleucine, alanine, tyrosine, ghrelin, and PYY, and excluding hydroxyproline, beta-aminoisobutyric-acid, hexanoic acid, and phenylalanine, and said behavioral assessment does indicate anxiety on a behavioral questionnaire, and wherein said intervention is a pharmacotherapy selected from the group consisting of an appetite suppressant, leptin modulators, MetAP2 inhibitors, B3 agonists and any combination of distinct pharmacotherapies thereof.

2. The method of claim 1, wherein said sample is selected from the group consisting of a blood sample, a saliva sample, a urine sample, a breath sample, and a stool sample.

3. The method of claim 2, wherein said sample is a breath sample.

4. The method of claim 2, wherein said sample is a stool sample.

5. A method for treating obesity in a mammal in need thereof, wherein said method comprises administering an intervention to a mammal identified as having an obesity analyte signature unique to a body mass index (BMI) of >30 kg/m$^2$ or a BMI>27 kg/m$^2$ with an obesity-related comorbidity in a sample obtained from said mammal, wherein said obesity analyte signature comprises a behavioral assessment and a plurality of analytes selected from the group consisting of metabolites, gastrointestinal peptides, single nucleotide polymorphisms and any combination thereof, wherein said obesity analyte signature is obtained from a regression model of one or more variables comprising:

(i) serotonin, glutamine, isocaproic acid, allo-isoleucine, hydroxyproline, beta-aminoisobutyric-acid, alanine, hexanoic acid, tyrosine, and PYY, and excluding 1-methylhistine, gamma-amino-n-butyric-acid, phenylalanine, and ghrelin, and said behavioral assessment does not indicate anxiety on a behavioral questionnaire, and wherein said intervention is a pharmacotherapy selected from the group consisting of an appetite suppressant, an appetite suppressant in combination with an anticonvulsant a melanocortin receptor agonist, CCK analogs and any combination of distinct pharmacotherapies thereof; or (ii) 1-methylhistine, allo-isoleucine, hydroxyproline, beta-aminoisobutyric-acid, alanine, and phenylalanine, and excluding serotonin, glutamine, gamma-amino-n-butyric-acid, isocaproic acid, hexanoic acid, tyrosine, ghrelin, and PYY, and said behavioral assessment does not indicate anxiety on a behavioral questionnaire, and wherein said intervention is a pharmacotherapy selected from the group consisting of a GLP-1 analog, GLP-1 receptor agonist, amylin analogs, PYY analogs, Y receptor agonists or antagonists, oxyntomodulin analogs, ghrelin antagonists, TGR5 agonists, FGF-19/21analogs, FXR agonists, GRP-119, GRP-120 and any combination of distinct pharmacotherapies thereof; or (iii) serotonin, and excluding 1-methylhistine, glutamine, gamma-amino-n-butyric-acid, isocaproic acid, allo-isoleucine, hydroxyproline, beta-aminoisobutyric-acid, alanine, hexanoic acid, tyrosine, phenylalanine, ghrelin, and PYY, and said behavioral assessment does indicate anxiety on a behavioral questionnaire, and wherein said intervention is a pharmacotherapy selected from the group consisting of an anti-depressant, an opioid antagonist, an anti-anxiety agent, a cannabinoid antagonist and any combination of distinct pharmacotherapies thereof; or (iv) 1-methylhistine, glutamine, gamma-amino-n-butyric-acid, isocaproic acid, allo-isoleucine, beta-aminoisobutyric-acid, alanine, hexanoic acid, tyrosine, phenylalanine, and PYY, and excluding serotonin, hydroxyproline, and ghrelin, and said behavioral assessment does indicate anxiety on a behavioral questionnaire, and wherein said intervention is a pharmacotherapy selected from the group consisting of an anti-depressant, an opioid antagonist, an anti-anxiety agent, a cannabinoid antagonist and any combination of distinct pharmacotherapies thereof; or (v) 1-methylhistine, serotonin, glutamine, gamma-amino-n-butyric-acid, isocaproic acid, allo-isoleucine, alanine, tyrosine, ghrelin, and PYY, and excluding hydroxyproline, beta-aminoisobutyric-acid, hexanoic acid, and phenylalanine, and said behavioral assessment does indicate anxiety on a behavioral questionnaire, and wherein said intervention is a pharmacotherapy selected from the group consisting of an appetite suppressant, leptin modulators, MetAP2 inhibitors, B3 agonists and any combination of distinct pharmacotherapies thereof.

6. The method of claim 1, wherein said mammal is a human.

7. The method of claim 1, wherein said intervention is effective to reduce the total body weight of said mammal by at least 4%.

8. The method of claim 1, wherein said intervention is effective to reduce the total body weight of said mammal by from about 3 kg to about 100 kg.

9. The method of claim 1, wherein said intervention is effective to reduce the waist circumference of said mammal by from about 1 inches to about 10 inches.

10. The method of claim 1, wherein said behavioral questionnaire is a Hospital Anxiety and Depression Scale (HADS) questionnaire.

11. The method of claim 10, wherein said obesity analyte signature is obtained from a regression model of one or more variables comprising serotonin, glutamine, isocaproic acid, allo-isoleucine, hydroxyproline, beta-aminoisobutyric-acid, alanine, hexanoic acid, tyrosine, and PYY, and excluding of 1-methylhistine, gamma-amino-n-butyric-acid, phenylalanine, and ghrelin; wherein said HADS questionnaire result does not indicate anxiety; and wherein said pharmacotherapy is an appetite suppressant selected from the group consisting of phentermine-topiramate pharmacotherapy, desvenlafaxine and lorcaserin pharmacotherapy.

12. The method of claim 10, wherein said obesity analyte signature is obtained from a regression model of one or more variables comprising 1-methylhistine, allo-isoleucine, hydroxyproline, beta-aminoisobutyric-acid, alanine, and phenylalanine, and excluding serotonin, glutamine, gamma-amino-n-butyric-acid, isocaproic acid, hexanoic acid, tyrosine, ghrelin, and PYY; wherein said HADS questionnaire result does not indicate anxiety; and wherein said pharmacotherapy is a GLP-1 receptor agonist.

13. The method of claim 10, wherein said obesity analyte signature is obtained from a regression model of one or more variables comprising serotonin, and excluding 1-methylhistine, glutamine, gamma-amino-n-butyric-acid, isocaproic acid, allo-isoleucine, hydroxyproline, beta-aminoisobutyric-acid, alanine, hexanoic acid, tyrosine, phenylalanine, ghrelin, and PYY; wherein said HADS questionnaire result indicates anxiety; and wherein said pharmacotherapy is naltrexone-bupropion pharmacotherapy.

14. The method of claim 10, wherein said obesity analyte signature is obtained from a regression model of one or more variables comprising 1-methylhistine, glutamine, gamma-amino-n-butyric-acid, isocaproic acid, allo-isoleucine, beta-aminoisobutyric-acid, alanine, hexanoic acid, tyrosine, phenylalanine, and PYY, and excluding serotonin, hydroxyproline, and ghrelin; wherein said HADS questionnaire result indicates anxiety; and wherein said pharmacotherapy is naltrexone-bupropion pharmacotherapy.

15. The method of claim 10, wherein said obesity analyte signature is obtained from a regression model of one or more variables comprising 1-methylhistine, serotonin, glutamine, gamma-amino-n-butyric-acid, isocaproic acid, allo-isoleucine, alanine, tyrosine, ghrelin, and PYY, and excluding hydroxyproline, beta-aminoisobutyric-acid, hexanoic acid, and phenylalanine; wherein said HADS questionnaire result indicates anxiety; and wherein said pharmacotherapy is phentermine pharmacotherapy.

16. The method of claim 12, wherein said GLP-1 receptor agonist comprises liraglutide.

* * * * *